(12) United States Patent
Mabondzo et al.

(10) Patent No.: US 11,472,807 B2
(45) Date of Patent: Oct. 18, 2022

(54) PURINE DERIVATIVES FOR USE AS MEDICAMENT AND FOR USE IN TREATING NEURODEGENERATIVE OR NEURO-INFLAMMATORY DISORDERS

(71) Applicants: COMMISSARIAT À L'ENERGIE ATOMIQUE ET AUX ENERGIES ALTERNATIVES, Paris (FR); PERHA PHARMACEUTICALS, Roscoff (FR)

(72) Inventors: Aloïse Mabondzo, Paris (FR); Charlotte Leuxe, Paris (FR); Anne-Cécile Guyot, Paris (FR); Nassima Oumata, Roscoff (FR); Laurent Meijer, Roscoff (FR)

(73) Assignees: COMMISSARIAT À L'ENERGIE ATOMIQUE ET AUX ENERGIES ALTERNATIVES, Paris (FR); PERHA PHARMACEUTICALS, Roscoff (FR)

( * ) Notice: Subject to any disclaimer, the term of this patent is extended or adjusted under 35 U.S.C. 154(b) by 0 days.

(21) Appl. No.: 16/604,330

(22) PCT Filed: Apr. 9, 2018

(86) PCT No.: PCT/EP2018/059059
§ 371 (c)(1),
(2) Date: Oct. 10, 2019

(87) PCT Pub. No.: WO2018/189122
PCT Pub. Date: Oct. 18, 2018

(65) Prior Publication Data
US 2020/0354364 A1 Nov. 12, 2020

(30) Foreign Application Priority Data
Apr. 10, 2017 (EP) .................. 17305429

(51) Int. Cl.
*C07D 473/34* (2006.01)
*A61P 25/28* (2006.01)
*C07D 473/30* (2006.01)

(52) U.S. Cl.
CPC ........... *C07D 473/34* (2013.01); *A61P 25/28* (2018.01); *C07D 473/30* (2013.01)

(58) Field of Classification Search
CPC .... C07D 473/30; C07D 473/34; A61K 31/52; A61K 31/522; A61P 25/00
See application file for complete search history.

(56) References Cited

U.S. PATENT DOCUMENTS

| 8,569,296 B2 * | 10/2013 | Liang | C07D 519/00 514/234.2 |
| 2003/0187261 A1* | 10/2003 | Havlicek | C07D 473/16 544/276 |
| 2016/0046631 A1* | 2/2016 | Bendels | A61P 1/00 514/210.21 |

FOREIGN PATENT DOCUMENTS

| EP | 2 664 619 A1 | 11/2013 |
| WO | 01/49688 A1 | 7/2001 |
| WO | 2004/016612 A2 | 2/2004 |
| WO | 2010/005558 A2 | 1/2010 |

OTHER PUBLICATIONS

Damasio, Alzheimer's Disease and related dementias, Cecil Textbook of Medicine, 20th Edition, vol. 2, pp. 1992-1996, 1996.*
Layzer, Degenerative diseases of the nervous system, Cecil Textbook of Medicine, 20th Edition, vol. 2, pp. 2050-2057, 1996.*
Tang et al., Crystal Structure of Pyridoxal Kinase in Complex with Roscovitine and Derivatives, The Journal of Biological Chemistry, vol. 280, No. 35, pp. 31220-31229 (2005).*
Oct. 12, 2017 Extended European Search Report issued in European Patent Application No. 17305429.
Jul. 6, 2018 Written Opinion issued in PCT Patent Application No. PCT/EP2018/059059.
L. Harmse et al. "Structure-activity relationships and inhibitory effects of various purine derivatives on the in vitro growth of Plasmodium falciparum." Biochemical Pharmacology. Elsevier Science Inc., vol. 62, Jan. 2001, pp. 341-348.

* cited by examiner

*Primary Examiner* — Deepak R Rao
(74) *Attorney, Agent, or Firm* — Oliff PLC

(57) ABSTRACT

Compound of formula (I)

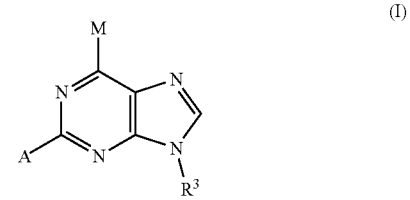

and its addition salts with pharmaceutically acceptable acids, and methods in which an effective amount of the compound or any pharmaceutically acceptable salt thereof is administered (as a medicament) to an individual in need thereof.

14 Claims, 21 Drawing Sheets

PURINE DERIVATIVES FOR USE AS MEDICAMENT AND FOR USE IN TREATING NEURODEGENERATIVE OR NEURO-INFLAMMATORY DISORDERS

FIELD OF THE INVENTION

The present invention relates to purine derivatives for use as medicament.

In particular, the present invention aims at providing purine derivatives for use in preventing and/or treating neurodegenerative disorders, e.g. Alzheimer's disease, Parkinson's disease, Huntington's disease amyotrophic lateral sclerosis and Down's syndrome, as well as disorders associated with neuro-inflammation, e.g. central nervous system (CNS) inflammatory disorders, inflammatory disorders associated with an autoimmune disease, joint inflammation disorders, inflammatory bowel diseases, viral-induced neuro-inflammatory disorders, traumatic brain injuries and inflammatory skin or epithelial disorders.

TECHNICAL BACKGROUND OF THE INVENTION

In the special issue of the 2013's Pharmaceuticals journal entitled "Purine and its derivatives", Pr. Hosmane wrote the following introduction:

"The purine ring system (imidazo[4,5-d]pyrimidine) is among the most ubiquitous of all the heterocyclic compounds. Although purine itself has never been found in nature, substituted purines like adenine and guanine or their respective nucleoside/nucleotide derivatives are the most common class of nitrogen heterocycles which play crucial roles in a wide variety of functions of living species. As nucleotides (AMP, GMP), they are the building blocks of nucleic acids (RNA/DNA). They serve as energy cofactors (ATP, GTP), as part of coenzymes (NAD/FAD) in oxidation-reduction reactions, as important second messengers in many intracellular signal transduction processes (cAMP/cGMP, or as direct neurotransmitters by binding to purinergic receptors (adenosine receptors). Therefore, it is not surprising that the analogues of purines have found utility both as chemotherapeutics (antiviral, antibiotic, and anti-cancer agents) and pharmacodynamic entities (regulation of myocardial oxygen consumption and cardiac blood flow). They can also act as substrates or inhibitors of enzymes of purine metabolism (ADA, Guanase, HGPRTase, PNPase, etc) in order to exert their chemotherapeutic property".

For years, a great deal of attention has been attached by chemists and pharmacologists to provide improved method for producing purine derivatives, in particular purine derivatives aimed at achieving therapeutic purposes.

Some documents disclose purine derivatives without any therapeutic applications, i.e. are only focused on their synthesis.

For example, Ramzaeva et al. (Synthetic Communications, 1989; 19(9&10), 1669-1676) provides high yield and simple processes to synthesize 6,9-substituted and 7,9-substituted purine compounds.

In addition, Baraldi et al. (Tetrahedron, 2002; 58, 7607-7611) discloses methods for efficiently synthesizing purine derivatives, in particular 6,9-bisubstituted and 6,8,9-trisubstituted purine compounds.

One of the known purine derivatives that has been recently developed is roscovitine, and in particular (R)-roscovitine which is a relatively selective inhibitor of cyclin-dependent kinases (CDKs), which has been evaluated for the treatment of cancers, neurodegenerative disorders, renal disease and several viral infections.

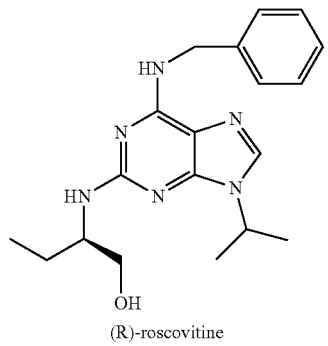

(R)-roscovitine

Another family of tri-substituted purines has been recently developed in a non-therapeutic approach: Aftins (Amyloid-β Forty-Two Inducers). Indeed these molecules have been showing production of $A\beta_{1-42}$. They have thus been investigated as pharmacological tools to investigate the molecular mechanism underlying the modified $A\beta_{1-42}/A\beta_{1-40}$ ratio associated in Alzheimer's disease (AD).

Bettayeb et al. (FASEB J., 2012; 26, 5115-5123) and Hochard et al. (J Alzheimer Dis., 2013; 35, 107-120) in particular, respectively disclose Aftin-4 and Aftin-5 as inducers of $A\beta_{1-42}$ production.

Further, patent EP 2 664 619 more generally discloses such Aftin derivatives as pharmacological tools to investigate AD. Said Aftin derivatives, as will be apparent in the rest of the present application via compounds of formula (I), have a special distinction in comparison to most of the known purine derivatives in that the N6 position is a tertiary amine and not a secondary amine.

Some documents disclose purine derivatives with various biological activities. For example, Knockaert et al. (Oncogene, 2002; 21, 6413-6424) discloses 2,6,9-substituted purine compounds, such as purvalanol and aminopurvalanol, which display, at least for some of them, an inhibitory effect on cyclin-dependent kinases and MAP kinases. Said compounds may hence potentially sustain anti-mitotic and anti-proliferative activities. On the contrary, methylated forms of purvalanol and aminopurvalanol on the N6 position represent inactive derivatives with respect to the inhibition of CDks and MAPKs.

Harmse et al. (Biochemical Pharmacology, 2001; 62, 341-348) discloses that purvalanol A, purvalanol B and aminopurvalanol display antimalarial activity, by the mean of an inhibitory effect of CDK1/cyclin B enzyme. On the contrary, methylated forms of purvalanol B and aminopurvalanol do not possess the inhibitory effect of CDK1/cyclin B enzyme. The later results are consistent with the teaching of Knockaert et al. (see above).

WO 98/05335 relates to 2,6,9-trisubstituted purine compounds for use in inhibiting cell proliferative disorders and for use as antifungal.

In addition several authors disclosed 2,6,9-trisubstituted purine compounds as kinase inhibitors, in particular, Vesely et al. (Eur. J. Biochem., 194; 224, 771-786); Shulze-Gahmen et al. (Proteins: Structure, Function and Genetics, 1995; 22, 378-391); Azevedo et al. (Eur. J. Biochem., 1997; 243, 518-526); Meijer et al. (Eur. J. Biochem., 1997; 243, 527-536); and Gray et al. (Science 281, 1998; 533-538).

WO 01/49688 relates to purine derivatives, aimed at achieving inhibitory effects on CDKs, on viruses, and on proliferation of hematopoietic and cancer cells.

However, among the herein above cited prior art documents, none disclose or suggest the use of Aftin derivatives as defined herein after, i.e. in particular with a tertiary amine on the N6 position thereof, useful as medicament. In other words, none of said documents teaches that such a derivative could be considered as a medicament candidate, regardless of a specific biological activity.

At last and interestingly, a great amount of research has been and is currently conducted to take advantage or purine derivatives' properties to provide therapeutic approaches towards Alzheimer's disease (AD).

It is noteworthy to mention that, to date, there is no effective therapy for AD. In fact, current therapies treat only the symptoms of AD, having limited efficacy and problematic side effects in some patients. This is notably the case of acetylcholine esterase inhibitors, which are employed to maintain cholinergic activity, despite progressive loss of cholinergic neurons. The commercial opportunity for new therapies is considerable, but, because of the complexity and sensitivity of the brain, investment in discovery and development carries significantly greater risk than for non-CNS disorders.

Thus, among the documents mentioning potential candidate compounds having an effect towards the physiological mechanisms involved in AD, one may cite the following documents.

Oumata et al. (J. Med. Chem., 2008; 51, 5229-5242) discloses roscovitine-derived compounds that inhibit cyclin-dependent kinases (CDKs) and casein kinases 1 (CK1), which are involved in the production of Aβ production and hyper-phosphorylation of Tau protein in AD.

WO 2002/04450 provides purine derivatives that inhibit the formation of Aβ proteins or stimulate the formation of amyloid precursor protein gene (APP).

WO 2002/04451 provides purine derivatives that stimulate the synthesis and/or secretion of synaptophysin, in order to compensate its loss in AD patients.

WO 2004/016612 and WO 2008/122767 provide purine derivatives intended to inhibit GSK-3 activity, resulting in a decrease of abnormal Tau protein hyper-phosphorylation.

Rivkin et al. (Bioorganic & Medicinal Chemistry Letters, 2010; 20, 2279-2282) and WO 2010/019392 disclose purine derivatives for the treatment of AD. These purine derivatives have been disclosed to exert a modulation of the γ-secretase activity, which result in a selective reduction of the formation of Aβ42 protein.

WO 2013/062762 provides caffeinated compounds that inhibit and/or prevent AR aggregation.

However, none of the specific compounds as disclosed in said documents more specifically dedicated to AD has a tertiary amine on the N6 position.

Moreover, all of these purine derivatives are single targeted compounds, having a limited effect towards a single mechanism observed in AD. Therefore, there is a need to provide compounds having a multi-targeted approach to prevent and/or treat AD, other neurodegenerative disorders and/or neuro-inflammatory disorders.

SUMMARY OF THE INVENTION

It has now been surprisingly found that Aftin compounds, and more particularly compounds of formula (I) as defined hereinafter, are useful as medicament.

On the basis of the biological activities as illustrated in the experimental data herein after, said compounds may in particular be useful in the treatment of neurodegenerative disorders, e.g. Alzheimer's disease, Parkinson's disease, Huntington's disease, amyotrophic lateral sclerosis and Down's syndrome, and disorders associated with neuro-inflammation, e.g. central nervous system (CNS) inflammatory disorders, inflammatory disorders associated with an autoimmune disease, joint inflammation disorders, inflammatory bowel diseases, viral-induced neuro-inflammatory disorders, traumatic brain injuries and inflammatory skin or epithelial disorders.

The present invention therefore relates to compounds of formula (I) as defined below for use in preventing and/or treating neurodegenerative disorders or neuro-inflammatory disorders, as defined above.

The present invention moreover relates to a method for preventing and/or treating neurodegenerative disorders or neuro-inflammatory disorders, as defined above, comprising at least one step consisting in administering to an individual at risk of developing said disorder, or suffering from said disorder, an effective amount of a compound of formula (I) as defined below or one of its pharmaceutically acceptable salts.

The present invention also provides pharmaceutical compositions comprising at least one of said compounds.

The invention further provides pharmaceutical compositions for use in preventing and/or treating a neurodegenerative disorder and/or a neuro-inflammatory disorder.

DEFINITIONS

Figure 1:
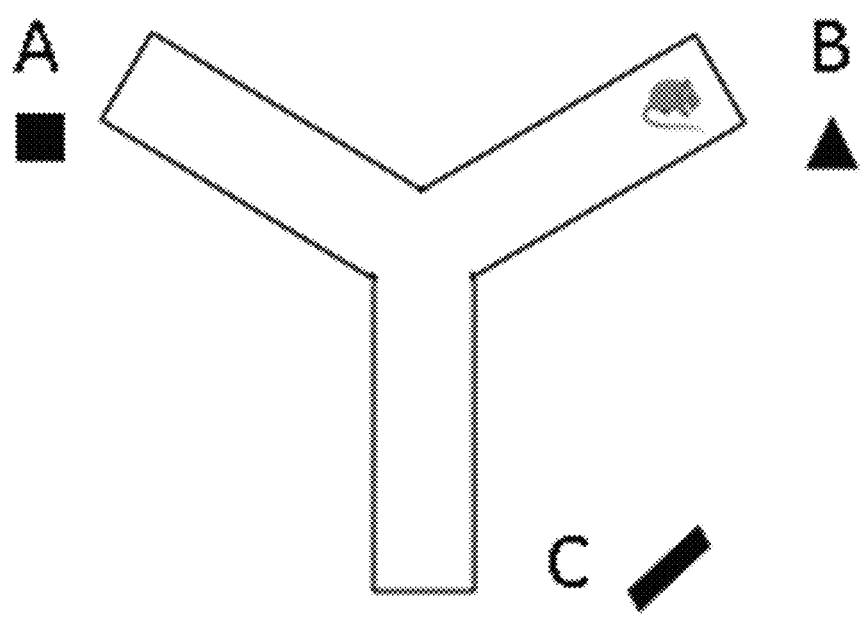
FIG. 1. Schematic plot illustrating the three arms of the Y-maze test.

As used herein, the term "individual" refers to either an animal, such as a valuable animal for breeding, company or preservation purposes, or preferably a human or a human child, which is afflicted with, or has the potential to be afflicted with one or more diseases and conditions described herein.

In particular, as used in the present application, the term "individual" refers to a mammal such as a rodent, cat, dog, primate or human, preferably said subject is a human.

The identification of those individuals who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those individuals who are in need of such treatment.

The term "effective amount" includes "prophylaxis-effective amount" as well as "treatment-effective amount".

The term "preventing", as used herein, means reducing the risk of onset or slowing the occurrence of a given phenomenon.

As used herein, "preventing" also encompasses "reducing the likelihood of occurrence" or "reducing the likelihood of reoccurrence".

The term "prophylaxis-effective amount" refers to a concentration of compound of this invention that is effective in inhibiting, decreasing the likelihood of the concerned diseases.

Likewise, the term "treatment-effective amount" refers to a concentration of compound that is effective in treating the concerned diseases.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

DETAILED DESCRIPTION OF THE INVENTION

Bettayeb et al. (2012), Hochard et al. (2013) and patent EP 2 664 619 as mentioned above, teach the selective induction of $A\beta_{1-42}$ versus $A\beta_{1-40}$, which was observed in cell line model, suggesting the existence of a general mechanism allowing, under certain conditions, the specific production of $A\beta_{1-42}$ but not $A\beta_{1-40}$. In particular, the disclosure of patent EP 2 664 619 strongly suggests that the purine "compounds represent potential hazards as possible 'pro-Alzheimer' compounds (Alzheimer inducing compounds)".

Now, by focusing on the molecular mechanisms underlying the production of selective $A\beta_{1-42}$, the inventors very surprisingly demonstrated that Aftin-5, its analogs and derivatives, exhibit beneficial properties in vitro and in vivo and plead in favor of their therapeutic use as drugs for the treatment of AD, other neurodegenerative disorders and disorders associated with neuro-inflammation. This assertion is based on solid in-vitro and in-vivo data including pharmacokinetics and pharmacodynamics studies on AD relevant pathological models as illustrated, for the first time, in the following examples and more detailed herein after.

According to a first aspect, a subject-matter of the present invention relates to a compound of formula (I), as already described in EP 2 664 619,

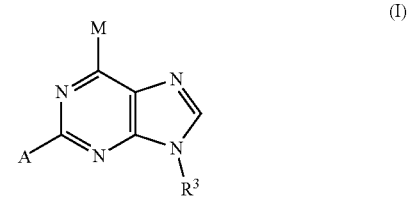

in which

M represents a $NR^1R^2$ group, an $OR^1$ group or a $SR^1$ group,

A represents a $NR^4R^5$ group, an $OR^{10}$ group or a hydrogen atom, $R^1$ is an aryl group, a heteroaryl group, a —$CH_2$-aryl group or a —$CH_2$-heteroaryl group, said aryl and heteroaryl being optionally substituted with one or more substituents independently chosen from a halogen atom, a $CF_3$ group, a hydroxyl group, an $OR^6$ group, a $SR^6$ group, a $NR^6R^7$ group, a CN group, a $CONR^6R^7$ group, a $SOR^6$ group, a $SO_2R^6$ group, an azido group (—$N_3$), an aryl group, a heteroaryl group and a ($C_1$-$C_6$)alkyl group, $R^2$ is a ($C_1$-$C_6$)alkyl group or a ($C_1$-$C_6$)cycloalkyl group said alkyl and cycloalkyl being optionally substituted with one or more substituents independently chosen from a halogen atom, a hydroxyl group and a $NH_2$ group, or $R^1$ forms together with $R^2$ and with the nitrogen atom that bears $R^1$ and $R^2$ an heterobicyclic ring, $R^6$ and $R^7$ represent independently of each other a hydrogen atom or a ($C_1$-$C_6$)alkyl group, $R^3$ is a $(C_1-C_6)$alkyl group, a $(C_1-C_6)$cycloalkyl group, an aryl group, a —$CH_2$-aryl group, a $CH_2$—$(C_1-C_6)$cycloalkyl group or a —$CH_2$-heteroaryl group, said alkyl, cycloalkyl, aryl and heteroaryl group being optionally substituted with one or more substituents independently chosen from a halogen atom, a hydroxyl group and a $NH_2$ group, $R^4$ is a hydrogen atom, a $(C_1-C_6)$alkyl group, a $(C_1-C_6)$ cycloalkyl group, an aryl group or a heteroaryl group, said alkyl and cycloalkyl being optionally substituted with one or more substituents independently chosen from a halogen atom, a hydroxyl group and a $NH_2$ group, said aryl and heteroaryl being optionally substituted with one or more substituents chosen from a halogen atom, a hydroxyl group, a $NH_2$ group and a NH—$R^9$ group, $R^9$ is a heteroaryl group optionally substituted with one or more substituents chosen from a halogen atom, a hydroxyl group, a $NH_2$ group and a heteroaryl group, $R^5$ is a hydrogen atom, a $(C_1-C_8)$alkyl group or a $(C_1-C_6)$cycloalkyl group, said alkyl and cycloalkyl being optionally substituted with one or more substituents independently chosen from a halogen atom, a hydroxyl group, an azido group and a $NR^6R^7$ group, one or more of the carbon atoms of said alkyl or cycloalkyl being optionally replaced by a nitrogen atom, or alternatively $R^4$ and $R^5$ may form with the nitrogen atom bearing them a $(C_3-C_6)$heterocylcoalkyl group, said $(C_3-C_6)$heterocylcoalkyl group being optionally substituted by one or more substituents independently chosen from a $(C_1-C_4)$alkyl group, a $NR^6R^7$ group and a halogen atom, $R^{10}$ is a hydrogen atom, a $(C_1-C_6)$alkyl group, a $(C_1-C_6)$ cycloalkyl group, an aryl group, a heteroaryl group, a —$CH_2$-aryl group or —$CH_2$-heteroaryl group, said aryl being optionally substituted with one or more substituents chosen from a halogen atom, a hydroxyl group, an $OR^6$ group, a $SR^6$ group, a $NR^6R^7$ group, a CN group, a $CONR^6R^7$ group, a $SO_2NR^6R^7$ group, a $SOR^6$ group, a $SO_2R^6$ group and an azido group ($N_3$), and its addition salts with pharmaceutically acceptable acids, for use as a medicament.

According to a particular embodiment, a subject-matter of the present invention relates to a compound of formula (I) as defined above, wherein M represents a $NR^1R^2$ group, an $OR^1$ group or a $SR^1$ group, A represents a $NR^4R^5$ group comprising at least three carbon atoms, a $NH_2$ group, an $OR^{10}$ group or a hydrogen atom, $R^1$ is an aryl group, a heteroaryl group, a —$CH_2$-aryl group or a —$CH_2$-heteroaryl group, said aryl and heteroaryl being optionally substituted with one substituent chosen from a halogen atom, a $CF_3$ group, a hydroxyl group, an $OR^6$ group, a $SR^6$ group, a $NR^6R^7$ group, a CN group, a $CONR^6R^7$ group, a $SOR^6$ group, a $SO_2R^6$ group, an azido group (—$N_3$), an aryl group, a heteroaryl group and a $(C_1-C_6)$alkyl group, $R^2$ is a $(C_1-C_6)$alkyl group or a $(C_1-C_6)$cycloalkyl group said alkyl and cycloalkyl being optionally substituted with one or more substituents independently chosen from a halogen atom, a hydroxyl group and a $NH_2$ group, or $R^1$ forms together with $R^2$ and with the nitrogen atom that bears $R^1$ and $R^2$ an heterobicyclic ring, $R^6$ and $R^7$ represent independently of each other a hydrogen atom or a $(C_1-C_6)$alkyl group, $R^3$ is a $(C_1-C_6)$alkyl group, a $(C_1-C_6)$cycloalkyl group, an aryl group, a —$CH_2$-aryl group, a $CH_2$—$(C_1-C_6)$cycloalkyl group or a —$CH_2$-heteroaryl group, said alkyl, cycloalkyl, aryl and heteroaryl group being optionally substituted with one or more substituents independently chosen from a halogen atom, a hydroxyl group and a $NH_2$ group, $R^4$ is a hydrogen atom, a $(C_1-C_6)$alkyl group, a $(C_1-C_6)$ cycloalkyl group, an aryl group or a heteroaryl group, said alkyl and cycloalkyl being optionally substituted with one or more substituents independently chosen from a halogen atom, a hydroxyl group and a $NH_2$ group, said aryl and heteroaryl being optionally substituted with one or more substituents chosen from a halogen atom, a hydroxyl group, a $NH_2$ group and a NH—$R^9$ group, $R^9$ is a heteroaryl group optionally substituted with one or more substituents chosen from a halogen atom, a hydroxyl group, a $NH_2$ group and a heteroaryl group, $R^5$ is a hydrogen atom, a $(C_1-C_8)$ alkyl group or a $(C_1-C_6)$ cycloalkyl group, said alkyl and cycloalkyl being optionally substituted with one or more substituents independently chosen from a halogen atom, a hydroxyl group, an azido group and a $NR^6R^7$ group, one or more of the carbon atoms of said alkyl or cycloalkyl being optionally replaced by a nitrogen atom, or alternatively $R^4$ and $R^5$ may form with the nitrogen atom bearing them a $(C_3-C_6)$heterocylcoalkyl group, said $(C_3-C_6)$heterocylcoalkyl group being optionally substituted by one or more substituents independently chosen from a $(C_1-C_4)$alkyl group, a $NR^6R^7$ group and a halogen atom, $R^{10}$ is a hydrogen atom, a $(C_1-C_6)$alkyl group, a $(C_1-C_6)$ cycloalkyl group, an aryl group, a heteroaryl group, a —$CH_2$-aryl group or —$CH_2$-heteroaryl group, said aryl being optionally substituted with one or more substituents chosen from a halogen atom, a hydroxyl group, an $OR^6$ group, a $SR^6$ group, a $NR^6R^7$ group, a CN group, a $CONR^6R^7$ group, a $SO_2NR^6R^7$ group, a $SOR^6$ group, a $SO_2R^6$ group and an azido group ($N_3$), and its addition salts with pharmaceutically acceptable acids, for use as a medicament.

In the context of the present invention, the term "halogen" is understood to mean chlorine (Cl), fluorine (F), bromine (Br) or iodine (I).

The term "alkyl" as used herein refers to a linear or branched, saturated aliphatic hydrocarbon group. For instance a $(C_1-C_6)$alkyl group denotes a linear or branched carbon chain of 1 to 6 carbon atoms. Examples are, but are not limited to, methyl, ethyl, propyl, isopropyl, butyl, isobutyl, methylbutyl.

The term "cycloalkyl" refers to a cyclic alkyl group that may be substituted by one or more $(C_1-C_6)$alkyl groups. Examples are, but are not limited to cyclopropyl, cyclobutyl, cyclopentyl, methylcyclopropyl, methylcyclobutyl.

The term "$(C_3-C_6)$heterocylcoalkyl" refers to a $(C_3-C_6)$ cycloalkyl group wherein one or two of the carbon atoms are replaced with a heteroatom such as oxygen or nitrogen. Examples are, but not limited to, morpholinyl, piperidinyl, pyrrolidinyl, piperazinyl and homopiperazinyl.

The term "aryl" refers to a monocyclic or polycyclic aromatic hydrocarbon radical of 6-20 atoms derived by the removal of one hydrogen from a carbon atom of a parent aromatic ring system. Typical aryl groups include, but are not limited to 1 ring or 2 or 3 rings fused together. Said radical is typically derived from the rings selected from benzene, naphthalene, anthracene, and the like. "Aryl" preferably refers to radicals such as phenyl.

The term "heteroaryl" denotes a 5- or 6-membered aromatic ring comprising 1 or 2 heteroatoms or a bi-cyclic or tricyclic aromatic nucleus comprising from 1 to 4 heteroatoms, and at least one of the rings of which has 6 ring members, the other fused ring or rings having 5 or 6 ring members. Examples are, but not limited to, pyridyl, pyrrolyl, thiophenyl, thiazolyl, triazolyl, isothiazolyl, isoxazolyl, imidazolyl, pyrazolyl, pyrazinyl, pyrimidinyl and pyridazinyl.

The term "heteroatom" is understood to mean nitrogen (N), oxygen (O) or sulphur (S).

Preferably, the heteroaryl comprises at least one nitrogen atom. In particular, the heteroaryl does not comprise an oxygen atom. Finally, very preferably, the heteroaryl comprises only nitrogen as heteroatom(s). Thus, advantageously, the heteroaryl comprises from 1 to 4 nitrogen atoms.

Mention may more particularly be made of pyridyl, pyrrolyl, thiazolyl, pyrazolyl and triazolyl and even more particularly of pyridyl and pyrrolyl.

In the context of the present invention, the terms "aromatic ring", "aryl", and "heteroaryl" include all the positional isomers.

The term "heterobicyclic ring" refers to 8 to 14-membered bicyclic radical that comprises at least one heteroatom. Preferably one ring from the heterobicyclic ring is aromatic. In particular the heterobicyclic ring comprises only nitrogen as heteroatom(s). Finally, very particularly the heterobicyclic ring may be chosen from these 2 following radicals:

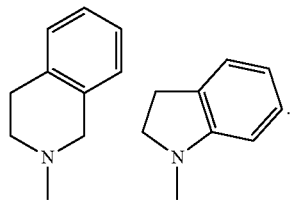

The M radical, when being $NR^1R^2$, may in particular be chosen among the following radicals (1) to (89):

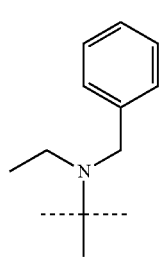 (1)

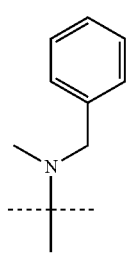 (2)

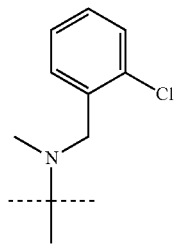 (3)

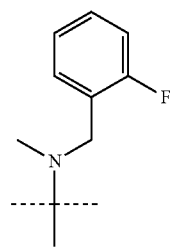 (4)

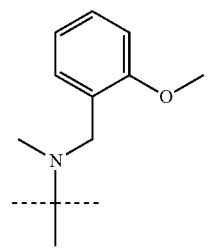 (5)

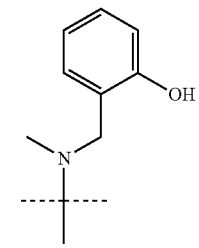 (6)

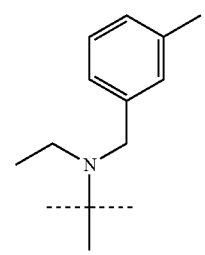 (7)

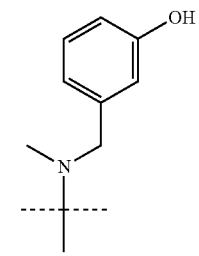 (8)

-continued
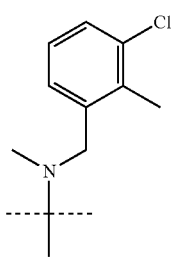
(9)
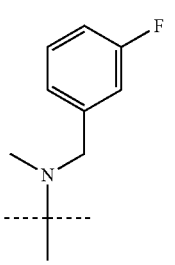
(10)
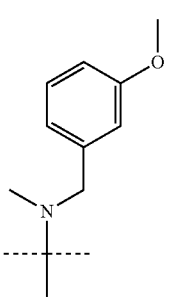
(11)
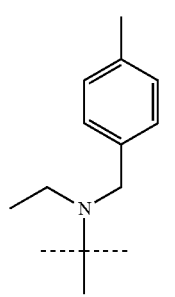
(12)
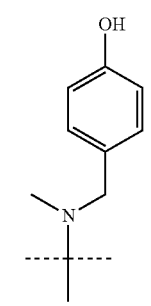
(13)
-continued
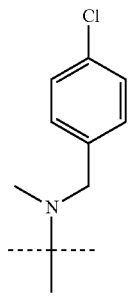
(14)
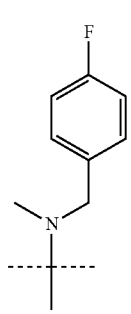
(15)
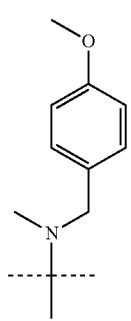
(16)
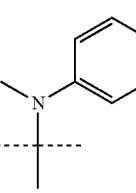
(17)
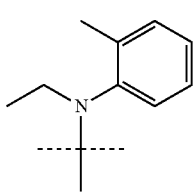
(18)
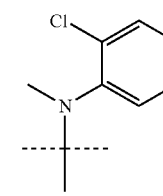
(19)

-continued
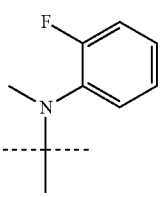 (20)
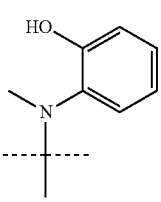 (21)
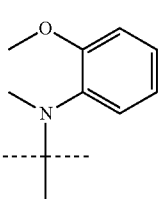 (22)
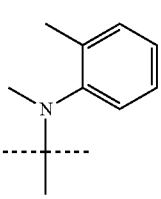 (23)
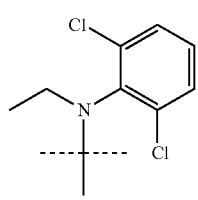 (24)
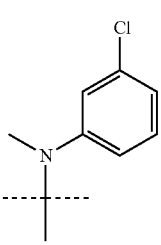 (25)
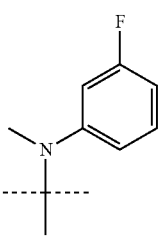 (26)
-continued
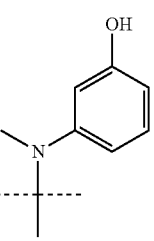 (27)
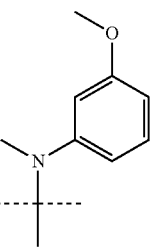 (28)
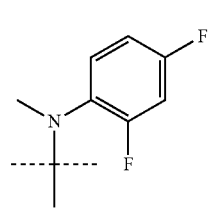 (29)
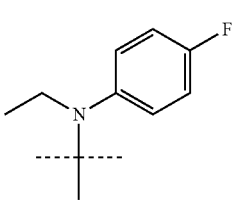 (30)
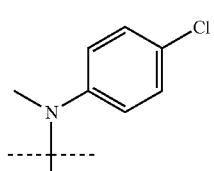 (31)
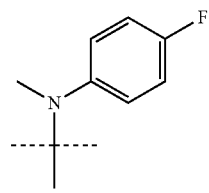 (32)
(33)

(34) 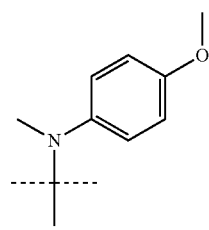
(35) 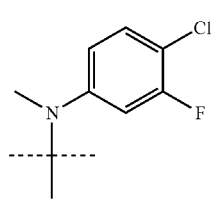
(36) 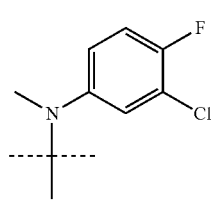
(37) 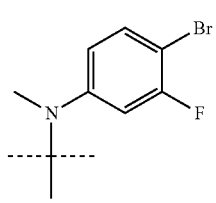
(38) 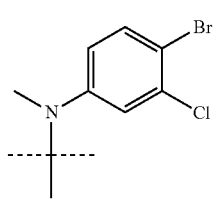
(39) 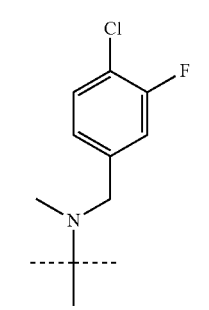
(40) 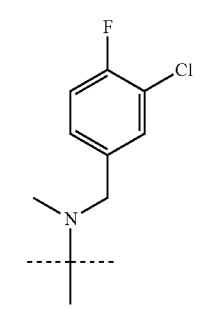
(41) 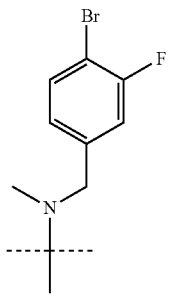
(42) 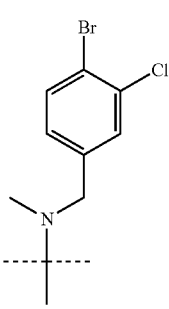
(43) 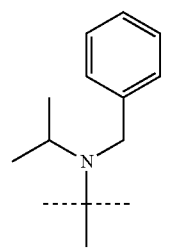
(44)
(45)
(46) 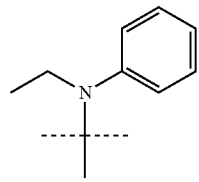

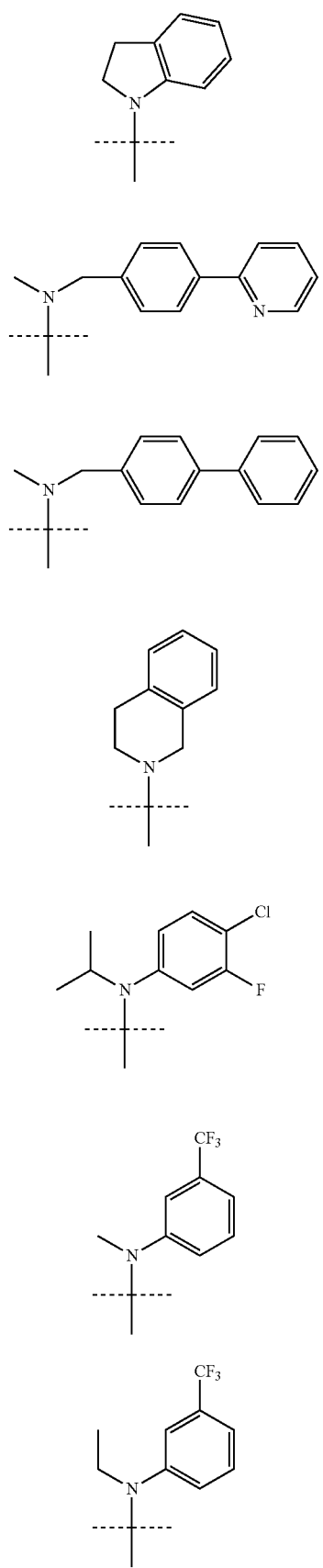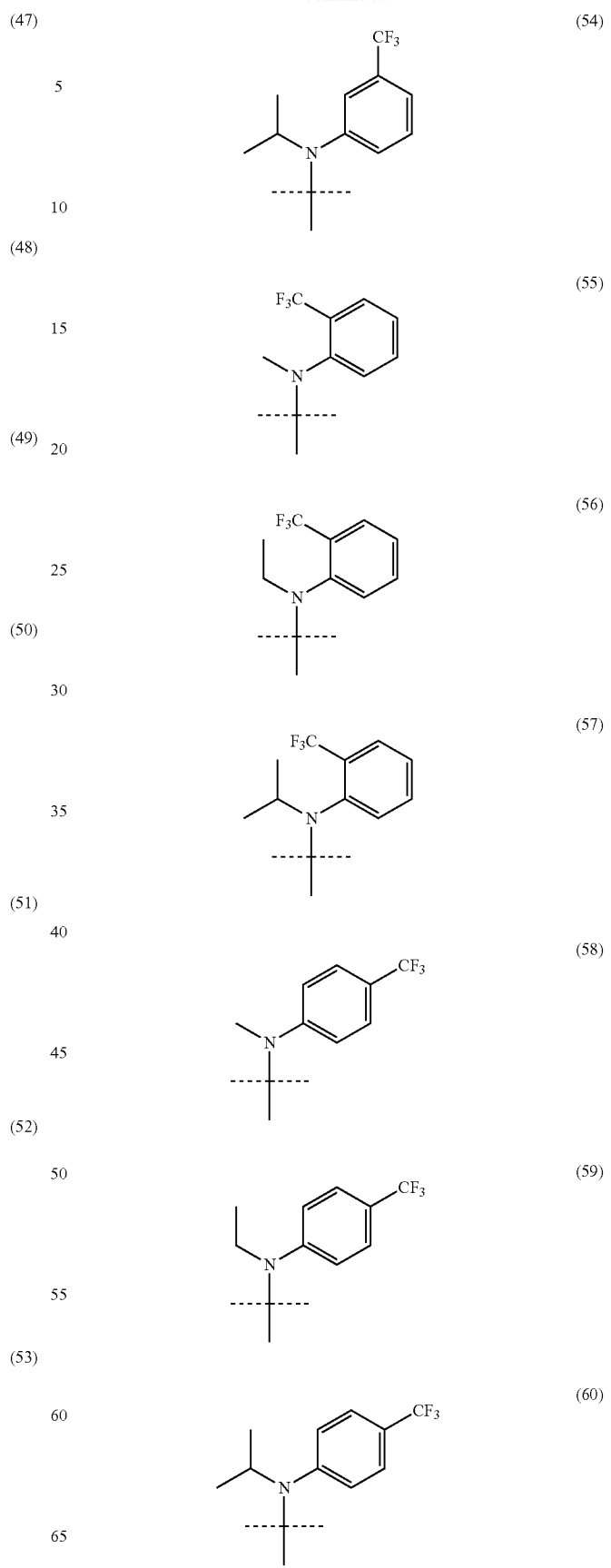

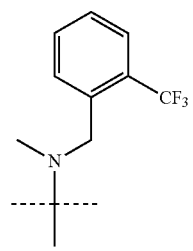
(61)
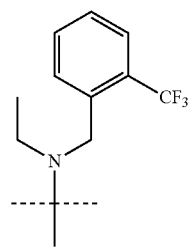
(62)
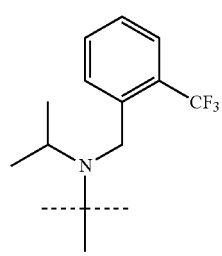
(63)
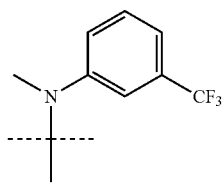
(64)
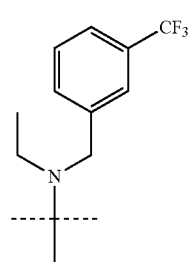
(65)
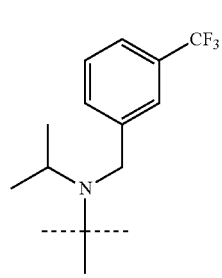
(66)
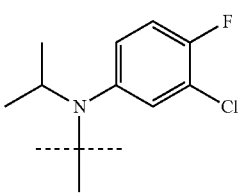
(67)
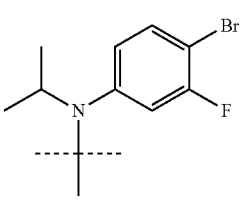
(68)
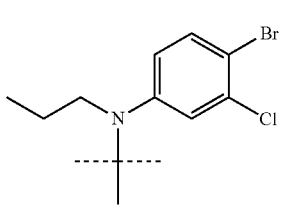
(69)
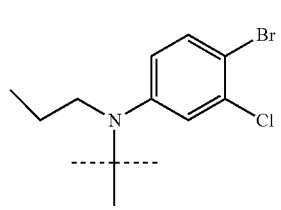
(70)
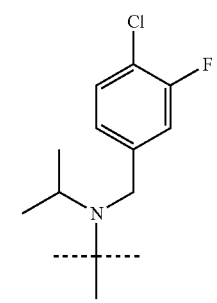
(71)
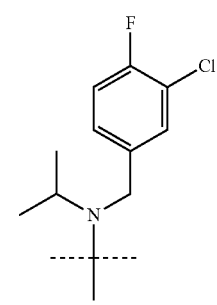
(72)

(73) 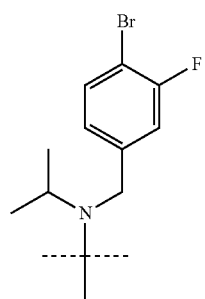
(74) 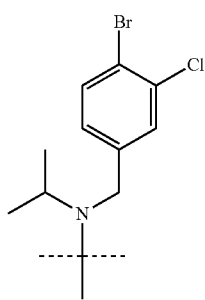
(75) 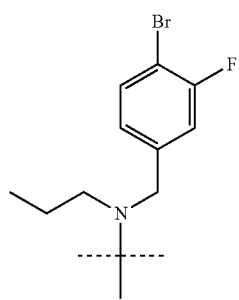
(76) 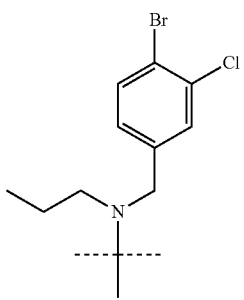
(77) 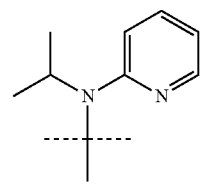
(78) 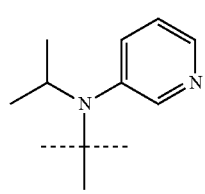
(79) 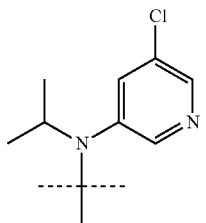
(80) 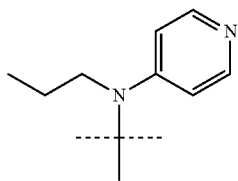
(81) 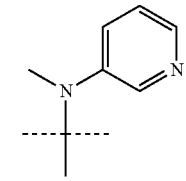
(82) 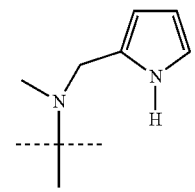
(83) 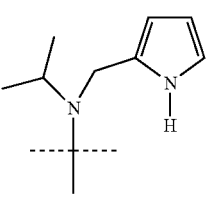
(84) 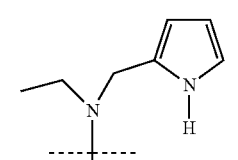
(85) 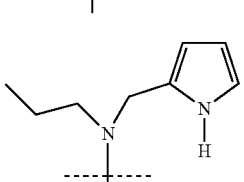
(86)

(87)
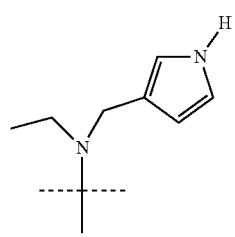
(88)
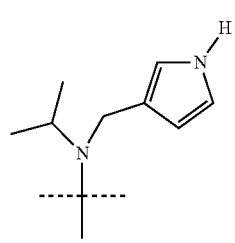
(89)
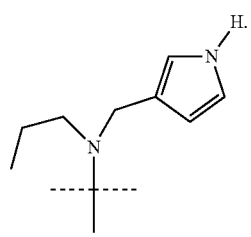
The A radical, when being NR⁴R⁵ may in particular be chosen among the following radicals (1') to (19'):
(1')
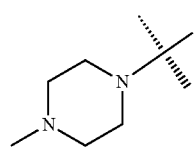
(2')
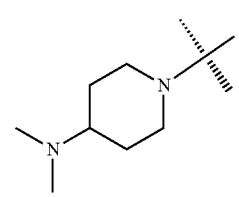
(3')
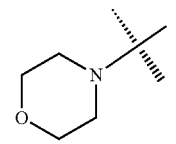
(4')
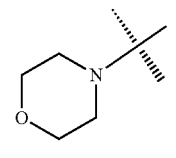
(5')
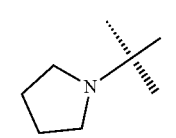
(6')
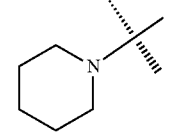
(7')
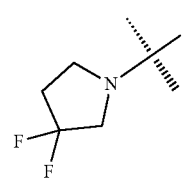
(8')
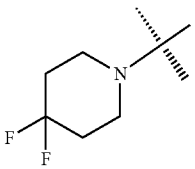
(9')
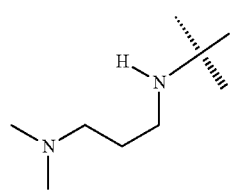
(10')
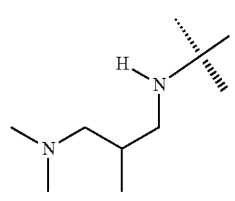
(11')
(12')
(13')

(14′)
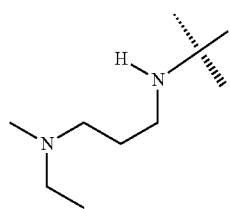
(15′)
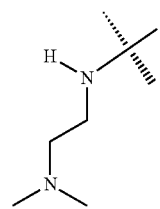
(16′)
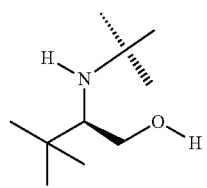
(17′)
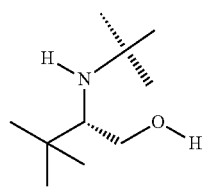
(18′)
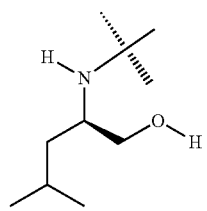
(19′)
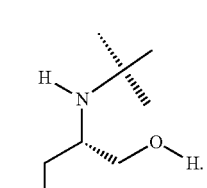
R³ may in particular be chosen among the following radicals (1″) to (14″):
(1″)
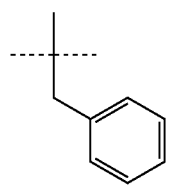
(2″)
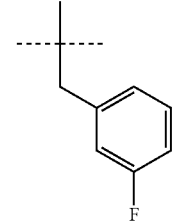
(3″)
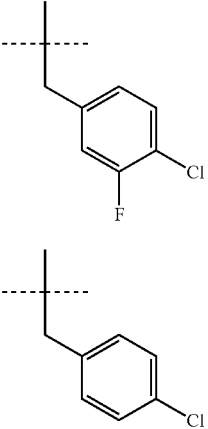
(4″)
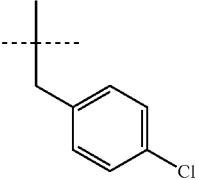
(5″)
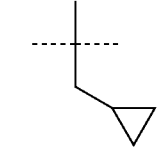
(6″)
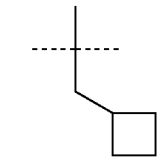
(7″)
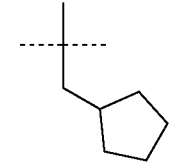
(8″)
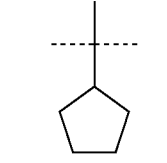
(9″)
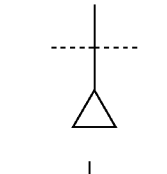
(10″)

-continued

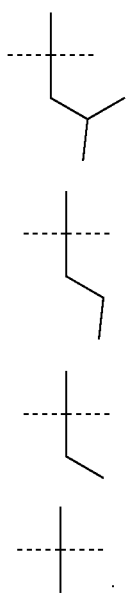

(11″)

(12″)

(13″)

(14″)

The present invention extends to the following new compounds:
  compounds of formula (I) wherein M and $R^3$ are as defined above and A is one of the radicals (5') to (19') as defined above,
  compounds of formula (I) wherein A and $R^3$ are as defined above and M is one of the radicals (35) to (42), (51) or (67) to (89) as defined above, and
  compounds of formula (I) wherein A and M are as defined above and $R^3$ is one of the radicals (2″) to (7″), (9″) and (11″) to (14″) as defined herein above,
  compounds of formula (I) wherein A and $R^3$ are as defined above and M is a $NR^1R^2$ group, where $R^1$ is an aryl group, a heteroaryl group, a —$CH_2$-aryl group or a —$CH_2$-heteroaryl group, said aryl and heteroaryl being substituted with at least one $CF_3$ group,
  and pharmaceutically acceptable salts thereof.

Among the compounds of general formula (I) for use as a medicament, a first subgroup of compounds is formed from compounds for which M represents a $NR^1R^2$ group, an $OR^1$ group or a $SR^1$ group,
  $R^1$ is an aryl group, a —$CH_2$-aryl group, a heteroaryl or a $CH_2$-heteroaryl group, said aryl and heteroaryl being optionally substituted with one or more substituents independently chosen from a halogen atom, a $CF_3$ group, a hydroxyl group, an $OR^6$ group, a $CONR^6R^7$ group, an azido group (—$N_3$), an aryl group, a heteroaryl group and a ($C_1$-$C_6$)alkyl group,
  $R^2$ is a ($C_1$-$C_6$)alkyl group,
  or $R^1$ forms together with $R^2$ and with the nitrogen atom that bears $R^1$ and $R^2$ an heterobicyclic ring,
  $R^6$ and $R^7$ represent independently of each other a hydrogen atom or a ($C_1$-$C_6$)alkyl group.

Among the compounds of general formula (I) for use as a medicament, a second subgroup of compounds is formed from compounds for which M represents a $NR^1R^2$ group, an $OR^1$ group or a $SR^1$ group;
  $R^1$ is an aryl group, a —$CH_2$-aryl group, a heteroaryl or a $CH_2$-heteroaryl, said aryl being optionally substituted with one or more substituents chosen from a halogen atom, a $CF_3$ group, an $OR^6$ group, a $CONR^6R^7$ group, an aryl group, a heteroaryl group and a ($C_1$-$C_6$)alkyl group,
  $R^2$ is a ($C_1$-$C_6$)alkyl group,
  or $R^1$ forms together with $R^2$ and with the nitrogen atom that bears $R^1$ and $R^2$ an heterobicyclic ring,
  $R^6$ and $R^7$ represent independently of each other a hydrogen atom or a ($C_1$-$C_6$)alkyl group.

Among the compounds of general formula (I) for use as a medicament, a third subgroup of compounds is formed from compounds for which M represents a $NR^1R^2$ group, an $OR^1$ group or a $SR^1$ group;
  $R^1$ is a phenyl group, a benzyl group, a pyridine group, a —$CH_2$-pyridine group, a pyrrole group or a —$CH_2$-pyrrole group, said groups being optionally substituted with one substituent chosen from a fluorine atom, a chlorine atom, a $CF_3$ group, an $OR^6$ group, a $CONR^6R^7$ group, a phenyl group, a pyridinyl group and a methyl group,
  $R^2$ is a methyl group, an ethyl group, a n-propyl group or an isopropyl group,
  or $R^1$ forms together with $R^2$ and with the nitrogen atom that bears $R^1$ and $R^2$ an heterobicyclic ring chosen from these 2 following radicals:

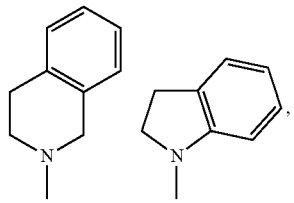

$R^6$ and $R^7$ represent independently of each other a hydrogen atom or a methyl group.

Among the compounds of general formula (I) for use as a medicament, a fourth subgroup of compounds is formed from compounds for which A represents a $NR^4R^5$ group, an $OR^{10}$ group or a hydrogen atom;
  $R^4$ is a hydrogen atom or a ($C_1$-$C_6$)alkyl group, said alkyl being optionally substituted with one hydroxyl group,
  $R^5$ is a hydrogen atom, a ($C_1$-$C_8$)alkyl group or a ($C_1$-$C_6$)cycloalkyl group, said alkyl being optionally substituted with one or two hydroxyl group, one of the carbon atoms of said alkyl or cycloalkyl being optionally replaced by a nitrogen atom,
  or alternatively $R^4$ and $R^5$ may form with the nitrogen atom bearing them a ($C_3$-$C_6$)heterocylcoalkyl group, said ($C_3$-$C_6$)heterocylcoalkyl group being optionally substituted by one or more substituents independently chosen from a ($C_1$-$C_4$)alkyl group, a $NR^6R^7$ group and a halogen atom,
  $R^{10}$ is a —$CH_2$-aryl group.

Among the compounds of general formula (I) for use as a medicament, a fifth subgroup of compounds is formed from compounds for which A represents a $NR^4R^5$ group, an $OR^{10}$ group or a hydrogen atom;
  $R^4$ is a hydrogen atom or a 2-hydroxyethyl group,
  $R^5$ is a hydrogen atom, a 1-hydroxybutan-2-yl group, a 1-hydroxy-3-methylbutan-2-yl group, a 1,2-dihydroxypropan-3-yl group, a N-ditehylaminoeth-2-yl group, a piperidin-4-yl group, a 2-hydroxyethyl group, or anyone of the radicals (12') to (19') as defined above,
  or alternatively $R^4$ and $R^5$ may form with the nitrogen atom bearing them a morpholinyl group, a piperazinyl group, a pyrrolidinyl group, a piperidinyl group, said groups being optionally substituted by one or more substituents independently chosen from a ($C_1$-$C_4$)alkyl group, a $NR^6R^7$ group and a halogen atom, and for example form anyone of the radicals (5') to (11') as defined above, $R^6$ and $R^7$ represent independently of each other a hydrogen atom or a methyl group, $R^{10}$ is a benzyl group.

Among the compounds of general formula (I) for use as a medicament, a sixth subgroup of compounds is formed from compounds for which $R^3$ represents a ($C_1$-$C_6$)alkyl group, a ($C_1$-$C_6$)cycloalkyl group or a —$CH_2$-aryl group, said aryl being optionally substituted by one or more substituents independently chosen from halogen atoms.

Among the compounds of general formula (I) for use as a medicament, a seventh subgroup of compounds is formed from compounds for which $R^3$ represents anyone of the radicals (1") to (14") as defined above, and more particularly a cyclopentyl group, an isopropyl group or a benzyl group.

Among the compounds of general formula (I) for use as a medicament, an eighth subgroup of compounds is formed by the compounds of general formula (I) in which, simultaneously, A and/or M and/or $R^3$ are as defined in the above subgroups.

Among the compounds of general formula (I) for use as a medicament, an ninth subgroup of compounds is formed by the compounds of general formula (I) in which, M represents a $NR^1R^2$ group, $R^2$ represents a ($C_2$-$C_6$)alkyl group or a ($C_1$-$C_6$)cycloalkyl group said alkyl and cycloalkyl being optionally substituted with one or more substituents chosen from a halogen atom, a hydroxyl group and a $NH_2$ group, and $R^1$, A and $R^3$ are as defined above, with $R^3$ being preferably an isopropyl group, a benzyl group or a cyclopentyl group.

According to said particular embodiment, M is preferably a radical (1), (2), (15), (17), (25), (43) or (44) as defined herein above and even more preferably a radical (1), (43) or (44) as defined herein above.

Compounds 13, 15, 18, 20, 22 and 23 as defined herein after in Table 1, and their pharmaceutically acceptable salts are in particular encompassed within the scope of said particular embodiment.

Among the compounds of general formula (I) for use as a medicament, an tenth subgroup of compounds is formed by the compounds of general formula (I) in which, M represents a $NR^1R^2$ group, $R^3$ is a ($C_1$-$C_6$)cycloalkyl group, an aryl group, a —$CH_2$-aryl group or a —$CH_2$-heteroaryl group, said cycloalkyl, aryl and heteroaryl group being optionally substituted with one or more substituents chosen from a halogen atom, a hydroxyl group and a $NH_2$ group, $R^3$ being preferably a benzyl group or a cyclopentyl group, $R^1$, A and $R^2$ are as defined above.

According to said particular embodiment, M is preferably a radical (1), (2), (15), (17), (25), (43) or (44) as defined herein above, and even more preferably a radical (1) or (2).

Compounds 14, 15, 18 and 22 as defined herein after in Table 1, and their pharmaceutically acceptable salts are in particular encompassed within the scope of said particular embodiment.

Among the compounds of general formula (I) for use as a medicament, an eleventh subgroup of compounds is formed by the compounds M represents a $NR^1R^2$ group, an $OR^1$ group or a $SR^1$ group, A represents a group a $NR^4R^5$ group selected from the radicals (1'), (2'), (3') and (4'), and $R^1$, $R^2$ and $R^3$ are as defined above, with $R^3$ being preferably an isopropyl group, a benzyl group or a cyclopentyl group.

According to said particular embodiment, $R^1$ is an aryl group, a heteroaryl group, a —$CH_2$-aryl group or a —$CH_2$-heteroaryl group, said aryl and heteroaryl being optionally substituted with one substituent chosen from a halogen atom, a $CF_3$ group, a hydroxyl group, an $OR^6$ group, a $SR^6$ group, a $NR^6R^7$ group, a CN group, a $CONR^6R^7$ group, a $SOR^6$ group, a $SO_2R^6$ group, an azido group (—$N_3$) and a ($C_1$-$C_6$)alkyl group.

According to said particular embodiment, M is preferably a radical (1), (2), (15), (17), (25), (43) or (44) as defined herein above and even more preferably a radical (1) or (2).

Compounds 13, 14, 15, 18, 20, 22, 23, 26, 38 and Aftin-5, as defined herein after in Table 1, and their pharmaceutically acceptable salts, are in particular encompassed within the scope of said particular embodiment.

Subfamilies of compounds of formula (I) are also reported herein after, still conform to EP 2 664 619, which may also be used as medicament. Therefore, said compounds of formula (Ia), (Ib), (Ic), (Id), (Ie) useful as medicament are a further subject-matters forming part of the present invention.

Compound of Formula (Ia)

They are defined as follows:

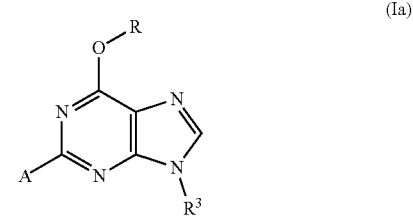

(Ia)

in which

A represents a $NR^4R^5$ group or an $OR^{10}$ group, $R^1$, $R^5$ and $R^{10}$ are as defined above, $R^3$ is a ($C_1$-$C_6$)alkyl group, a ($C_1$-$C_6$)cycloalkyl group, an aryl group, a —$CH_2$-aryl group or a —$CH_2$-heteroaryl group, said alkyl, cycloalkyl, aryl and heteroaryl group being optionally substituted with one or more substituents chosen from a halogen atom, a hydroxyl group and a $NH_2$ group, $R^4$ is a hydrogen atom, a ($C_1$-$C_6$) alkyl group or a ($C_1$-$C_6$)cycloalkyl group, said alkyl and cycloalkyl being optionally substituted with one or more substituents chosen from a halogen atom, a hydroxyl group and a $NH_2$ group.

According to a particular embodiment, the present invention relates to a compound of formula (Ia), as defined above, for use as a medicament, in which, A represents a $NR^4R^5$ group or an $OR^{10}$ group, $R^1$ is a —$CH_2$-aryl group, preferably a benzyl group, $R^3$ is a ($C_1$-$C_6$)alkyl group or a ($C_1$-$C_6$)cycloalkyl group, preferably a methyl, ethyl, cyclopropyl, cyclobutyl, methylcyclopropyl, methylcyclobutyl or isopropyl group, in particular an isopropyl group, $R^4$ is a hydrogen atom, $R^5$ is a ($C_1$-$C_6$)alkyl group or a ($C_1$-$C_6$)cycloalkyl group, said alkyl and cycloalkyl being optionally substituted with one hydroxyl group, preferably $R^5$ is a methyl, ethyl, cyclopropyl, cyclobutyl, methylcyclopropyl, methylcyclobutyl or 1-hydroxybutan-2-yl group in particular a 1-hydroxybutan-2-yl group, $R^{10}$ is a —CH$_2$-aryl group, preferably a benzyl group, and its addition salts with pharmaceutically acceptable acids.

Aftin-3, as represented herein after, is encompassed within the scope of said formula (Ia).

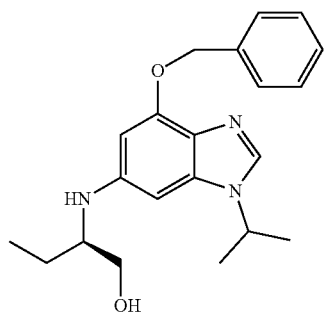 [SMILES: CC[C@H](CO)Nc1cc(OCc2ccccc2)c2ncn(C(C)C)c2c1]

The compounds Aftin-3 is disclosed in Tang et al. (J. Biol. Chem. 2005; 280, 31220-21229) as a negative control in a kinase activity test.

Compounds 31, 32 and 46 as defined herein after in Table 1, and their pharmaceutically acceptable salts, are in particular encompassed within the scope of formula (Ib).

Compound of Formula (Ib)

They are defined as follows:

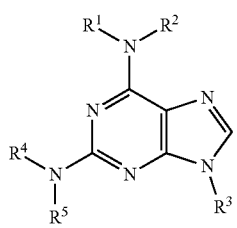

(Ib)

in which $R^1$, $R^2$ and $R^5$ are as defined above, $R^3$ is a (C$_1$-C$_6$)alkyl group, a (C$_1$-C$_6$)cycloalkyl group, an aryl group, a —CH$_2$-aryl group or a —CH$_2$-heteroaryl group, said alkyl, cycloalkyl, aryl and heteroaryl group being optionally substituted with one or more substituents chosen from a halogen atom, a hydroxyl group and a NH$_2$ group, $R^4$ is a hydrogen atom, a (C$_1$-C$_6$)alkyl group or a (C$_1$-C$_6$)cycloalkyl group, said alkyl and cycloalkyl being optionally substituted with one or more substituents chosen from a halogen atom, a hydroxyl group and a NH$_2$ group, and its addition salts with pharmaceutically acceptable acids.

Compounds 13, 14, 15, 18, 20, 22, 23, 26 and 38 as defined herein after in Table 1, and their pharmaceutically acceptable salts, are in particular encompassed within the scope of formula (Ib).

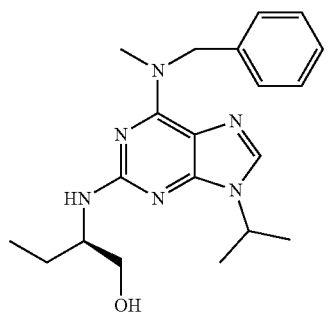 [SMILES: CC[C@H](CO)Nc1nc(N(C)Cc2ccccc2)c2ncn(C(C)C)c2n1]

Aftin-4 is encompassed within the scope of said formula (Ib). The compounds Aftin-4 is disclosed in Tang et al. (J. Biol. Chem. 2005; 280, 31220-21229) as a negative controls in a kinase activity test.

Aftin-5, as represented herein after, is also encompassed within the scope of said formula (Ib).

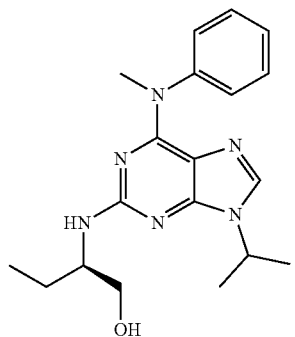 [SMILES: CC[C@H](CO)Nc1nc(N(C)c2ccccc2)c2ncn(C(C)C)c2n1]

Aftin-5 is disclosed and covered in EP 2 664 619.

According to a particular embodiment, the present invention relates to a compound of formula (Ib), as defined above, for use as a medicament, in which, the NR$^1$R$^2$ radicals are chosen from the radicals (1) to (89) as defined above.

According to an even more particular embodiment, the present invention relates to a compound of formula (Ib), as defined above, for use as a medicament, in which, the NR$^1$R$^2$ radical is as defined above, preferably, NR$^1$R$^2$ radical is chosen from radicals of formulae (1), (2), (11), (15), (17), (25), (32), (34) and (43) to (51) as defined above, and more particularly chosen from radicals of formulae (1), (2), (15), (17), (25), (43) and (44), $R^3$ is a (C$_1$-C$_6$)alkyl group, a (C$_1$-C$_6$)cycloalkyl group or a —CH$_2$-aryl group, a CH$_2$—(C$_1$-C$_6$)cycloalkyl group, preferably $R^3$ is a methyl, ethyl, cyclopropyl, cyclobutyl, methylcyclopropyl, methylcyclobutyl, isopropyl, cyclopentyl or benzyl group, in particular $R^3$ is an isopropyl, cyclopentyl or benzyl group, $R^4$ is a hydrogen atom, a (C$_1$-C$_6$)alkyl group or a (C$_1$-C$_6$)cycloalkyl group, said alkyl and cycloalkyl being optionally substituted with one or more hydroxyl group, preferably $R^4$ is a methyl, ethyl, cyclopropyl, cyclobutyl, methylcyclopropyl, methylcyclobutyl or 2-hydroxyethyl group or a hydrogen atom, in particular $R^4$ is a 2-hydroxyethyl group or a hydrogen atom, $R^5$ is a hydrogen atom, a (C$_1$-C$_6$)alkyl group or a (C$_1$-C$_6$)cycloalkyl group, said alkyl and cycloalkyl being optionally substituted with one or more hydroxyl group, one or more of the carbon atoms of said alkyl and cycloalkyl being optionally replaced by a nitrogen atom.

Preferably $R^5$ is a methyl, ethyl, cyclopropyl, cyclobutyl, methylcyclopropyl, methylcyclobutyl, 1-hydroxybutan-2-yl, 1-hydroxy-3-methylbutan-2-yl, 1,2-dihydroxypropan-3-yl, N-ditehylaminoeth-2-yl, piperidin-4-yl or 2-hydroxyethyl group, or a hydrogen atom, in particular $R^5$ is a 1-hydroxybutan-2-yl, 1-hydroxy-3-methylbutan-2-yl, 1,2-dihydroxypropan-3-yl, N-diethylaminoeth-2-yl, piperidin-4-yl or 2-hydroxyethyl group, or a hydrogen atom, and its addition salts with pharmaceutically acceptable acids.

Compound of Formula (Ic)
They are defined as follows:

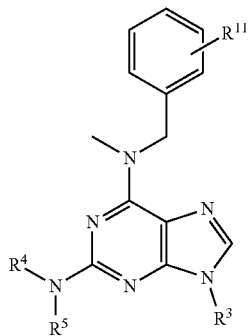

(Ic)

in which, $R^3$ is a $(C_1-C_6)$alkyl group, a $(C_1-C_6)$cycloalkyl group, a —$CH_2$-aryl group or a —$CH_2$-heteroaryl group, preferably $R^3$ is a methyl, ethyl, cyclopropyl, cyclobutyl, methylcyclopropyl, methylcyclobutyl, isopropyl, cyclopentyl or benzyl group, in particular $R^3$ is an isopropyl, cyclopentyl or benzyl group, $R^4$ is a hydrogen atom, $R^5$ is a hydrogen atom, a $(C_1-C_6)$alkyl group or a $(C_1-C_6)$cycloalkyl group, said alkyl and cycloalkyl being optionally substituted with one or more hydroxyl group, one or more of the carbon atoms of said cycloalkyl being optionally substituted by a nitrogen atom, preferably $R^5$ is a methyl, ethyl, cyclopropyl, cyclobutyl, methylcyclopropyl, methylcyclobutyl, 1-hydroxybutan-2-yl, 1,2-dihydroxypropan-3-yl or piperidin-4-yl group, or a hydrogen atom, in particular $R^5$ is a 1-hydroxybutan-2-yl, 1,2-dihydroxypropan-3-yl, or piperidin-4-yl group, or a hydrogen atom, $R^{11}$ is chosen from a halogen or a hydrogen atom, an $OR^6$ group, a $CONR^6R^7$ group, an aryl group and a heteroaryl group, preferably $R^{11}$ is an $OR^6$, $CONR^6R^7$, pyridinyl, phenyl group, or a fluorine or a hydrogen atom, $R^6$ and $R^7$ represent independently of each other a hydrogen atom or a $(C_1-C_6)$alkyl group, and its addition salts with pharmaceutically acceptable acids.

Compounds 14, and 38 as defined herein after in Table 1, and their pharmaceutically acceptable salts, are in particular encompassed within the scope of formula (Ic).

Compound of Formula (Id)
They are defined as follows:

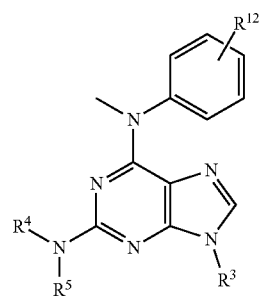

(Id)

in which, $R^3$ is a $(C_1-C_6)$alkyl group, a $CH_2$-aryl group, a —$CH_2$-heteroaryl group or a $(C_1-C_6)$cycloalkyl group, preferably $R^3$ is a methyl, ethyl, cyclopropyl, cyclobutyl, methylcyclopropyl, methylcyclobutyl, isopropyl or cyclopentyl group, in particular $R^3$ is an isopropyl or cyclopentyl group, $R^4$ is a hydrogen atom, a $(C_1-C_6)$alkyl group or a $(C_1-C_6)$cycloalkyl group, said alkyl and cycloalkyl being optionally substituted with one or more hydroxyl group, preferably $R^4$ is a methyl, ethyl, cyclopropyl, cyclobutyl, methylcyclopropyl, methylcyclobutyl or 2-hydroxyethyl group or a hydrogen atom, in particular $R^4$ is a 2-hydroxyethyl group or a hydrogen atom, $R^5$ is a $(C_1-C_6)$alkyl group or a $(C_1-C_6)$cycloalkyl group, said alkyl and cycloalkyl being optionally substituted with one or more hydroxyl group, preferably $R^5$ is a methyl, ethyl, cyclopropyl, cyclobutyl, methylcyclopropyl, methylcyclobutyl, 1-hydroxybutan-2-yl or 2-hydroxyethyl group, in particular $R^5$ is a 1-hydroxybutan-2-yl or 2-hydroxyethyl group, $R^{12}$ is chosen from a halogen, a $CF_3$ group or a hydrogen atom, an $OR^6$ group and a $(C_1-C_6)$alkyl group, preferably $R^{12}$ is a hydrogen, a $CF_3$ group, fluorine or chloride atom, or an $OR^6$ or methyl group, $R^6$ is a $(C_1-C_6)$alkyl group, preferably, $R^6$ is a methyl group, and its addition salts with pharmaceutically acceptable acids.

Compounds 26 and Aftin-5 as defined herein after in Table 1, and their pharmaceutically acceptable salts, are in particular encompassed within the scope of formula (Id).

Compound of Formula (Ie)
They are defined as follows:

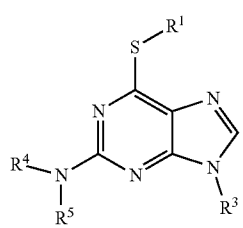

(Ie)

in which $R^1$ and $R^5$ are as defined above, $R^3$ is a $(C_1-C_6)$alkyl group, a $(C_1-C_6)$cycloalkyl group, an aryl group, a —$CH_2$-aryl group or a —$CH_2$-heteroaryl group, said alkyl, cycloalkyl, aryl and heteroaryl group being optionally substituted with one or more substituents chosen from a halogen atom, a hydroxyl group and a $NH_2$ group, $R^4$ is a hydrogen atom, a $(C_1$-$C_6)$alkyl group or a $(C_1$-$C_6)$cycloalkyl group, said alkyl and cycloalkyl being optionally substituted with one or more substituents chosen from a halogen atom, a hydroxyl group and a $NH_2$ group, and their addition salts with pharmaceutically acceptable acids.

According to a particular embodiment, the present invention relates to a compound of formula (Ie), as defined above, for use as a medicament, in which, $R^1$ is a —$CH_2$-aryl group, preferably a benzyl group,
$R^3$ is a $(C_1$-$C_6)$alkyl group, preferably an isopropyl group,
$R^4$ is a hydrogen atom,
$R^5$ is a $(C_1$-$C_6)$alkyl group being optionally substituted with one or more hydroxyl group, preferably $R^5$ is a 1-hydroxybutan-2-yl group, and its addition salts with pharmaceutically acceptable acids.

Compound 47 as defined herein after in Table 1, and its pharmaceutically acceptable salts, are in particular encompassed within the scope of formula (Ie).

The compounds of formulae (I), (Ia), (Ib), (Ic), (Id) and (Ie) can comprise one or more asymmetric carbon atoms. They can thus exist in the form of enantiomers or of diastereoisomers. These enantiomers, diastereoisomers and their mixtures, including the racemic mixtures, form part of the invention.

The pharmaceutically acceptable salts of the compounds of formulae (I), (Ia), (Ib), (Ic), (Id) and (Ie) include the addition salts with pharmaceutically acceptable acids, such as inorganic acids, for example hydrochloric, hydrobromic, phosphoric or sulphuric acid and organic acids, such as acetic, trifluoroacetic, propionic, oxalic, succinic, fumaric, malic, tartaric, citric, ascorbic, maleic, glutamic, benzoic, toluenesulphonic, methanesulphonic, stearic and lactic acid.

The compounds of formulae (I), (Ia), (Ib), (Ic), (Id) and (Ie) or their salts can form solvates (namely hydrates); the invention includes such solvates.

Therefore, the present invention furthermore concerns a compound of formula (I)

according to the disclosed invention herein, wherein
M represents a $NR^1R^2$ group or an $OR^1$ group,
$R^1$ is an aryl group, a heteroaryl group, a —$CH_2$-aryl group or a —$CH_2$-heteroaryl group, said aryl and heteroaryl being optionally substituted with one or more substituents independently chosen from a halogen atom, a $CF_3$ group, a hydroxyl group, an $OR^6$ group, a $SR^6$ group, a $NR^6R^7$ group, a CN group, a $CONR^6R^7$ group, a $SOR^6$ group, a $SO_2R^6$ group, an azido group (—$N_3$), an aryl group, a heteroaryl group and a $(C_1$-$C_6)$alkyl group, and preferably $R^1$ is an aryl group, a heteroaryl group, a —$CH_2$-aryl group or a —$CH_2$-heteroaryl group, said aryl and heteroaryl being optionally substituted with one halogen atom or a $CF_3$ group, $R^6$ and $R^7$ represent independently of each other a hydrogen atom or a $(C_1$-$C_6)$alkyl group, and $R^2$ is a $(C_1$-$C_6)$alkyl group or a $(C_1$-$C_6)$cycloalkyl group said alkyl and cycloalkyl being optionally substituted with one or more substituents independently chosen from a halogen atom, a hydroxyl group and a $NH_2$ group, and preferably $R^2$ is a $(C_1$-$C_6)$alkyl group, and its addition salts with pharmaceutically acceptable acids, for use as a medicament.

In some embodiments, M represents a $NR^1R^2$ group, and said $NR^1R^2$ radical is chosen from the following radicals:

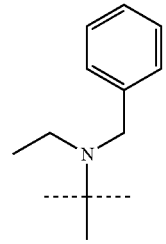

(1)

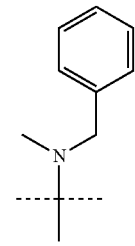

(2)

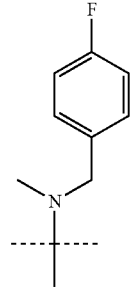

(15)

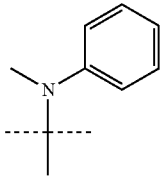

(17)

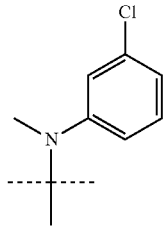

(25)

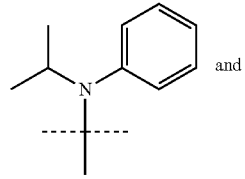

(43)

and

-continued (44)

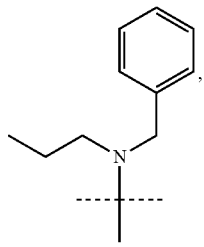

and their addition salts with pharmaceutically acceptable acids, for use as a medicament.

In some embodiments, the compound of formula (I) may be characterised in that: A represents a $NR^4R^5$ group,
$R^4$ is a hydrogen atom,
$R^5$ is a $(C_1-C_8)$ alkyl group, said alkyl being optionally substituted with one or more substituents independently chosen from a halogen atom, a hydroxyl group and a $NR^6R^7$ group, one or more of the carbon atoms of said alkyl being optionally replaced by a nitrogen atom, $R^5$ being preferably a $(C_1-C_6)$alkyl group, said alkyl being optionally substituted with one hydroxyl group, and one of the carbon atoms of said alkyl being optionally replaced by a nitrogen atom,
or alternatively $R^4$ and $R^5$ may form with the nitrogen atom bearing them a $(C_3-C_6)$heterocylcoalkyl group, said $(C_3-C_6)$heterocylcoalkyl group being optionally substituted by one or more substituents independently chosen from a $(C_1-C_4)$alkyl group, a $NR^6R^7$ group and a halogen atom, and
$R^6$ and $R^7$ represent independently of each other a hydrogen atom or a $(C_1-C_6)$alkyl group,
and its addition salts with pharmaceutically acceptable acids, for use as a medicament.

In some embodiments, A represents a group a $NR^4R^5$ group selected from the following radicals:

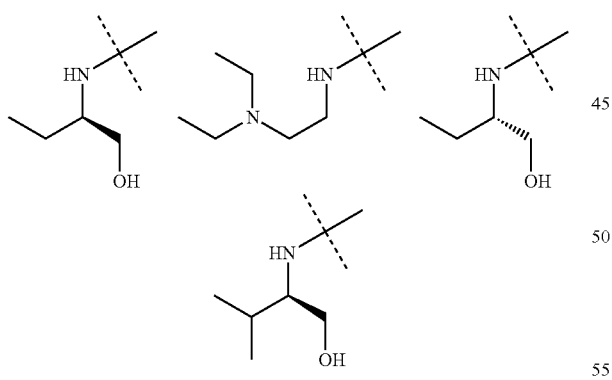

and their addition salts with pharmaceutically acceptable acids, for use as a medicament.

In some embodiments, the compound of formula (I) may be characterised in that: $R^3$ is a $(C_1-C_6)$alkyl group, a $(C_1-C_6)$cycloalkyl group, an aryl group or a —$CH_2$-aryl group, said alkyl, cycloalkyl and aryl group being optionally substituted with one or more substituents independently chosen from a halogen atom, a hydroxyl group and a $NH_2$ group, and preferably $R^3$ represents a cyclopentyl group, an isopropyl group or a benzyl group. and its addition salts with pharmaceutically acceptable acids, for use as a medicament.

More specific compounds are gathered in the following table, which may be used as medicament in the framework of the present invention, and in particular for preventing and/or treating neurodegenerative disorders or neuro-inflammatory disorders.

TABLE 1

| No | Structure |
|---|---|
| Aftin-1 | 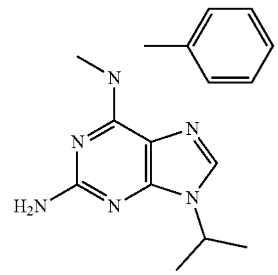 |
| Aftin-2 | 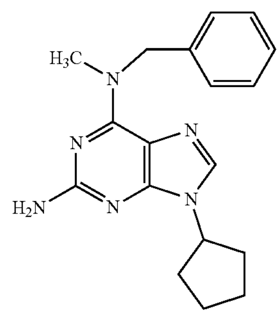 [SMILES: CN(Cc1ccccc1)c1nc(N)nc2c1ncn2C1CCCC1] |
| Aftin-3 | 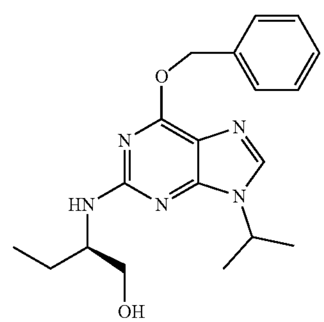 [SMILES: CC[C@H](CO)Nc1nc(OCc2ccccc2)c2ncn(C(C)C)c2n1] |
| Aftin-4 | 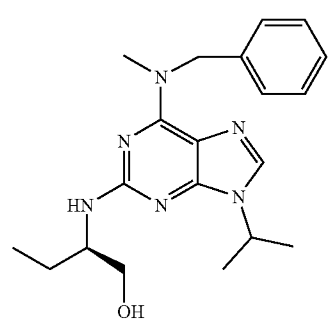 [SMILES: CC[C@H](CO)Nc1nc(N(C)Cc2ccccc2)c2ncn(C(C)C)c2n1] |

TABLE 1-continued

| No | Structure |
|---|---|
| Aftin-5 | 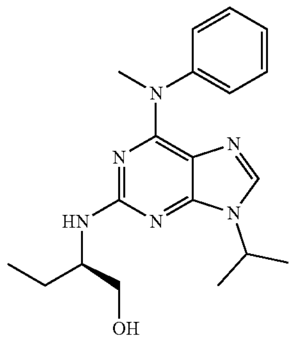 [SMILES: CC[C@H](CO)Nc1nc(N(C)c2ccccc2)c2ncn(C(C)C)c2n1] |
| 8 | 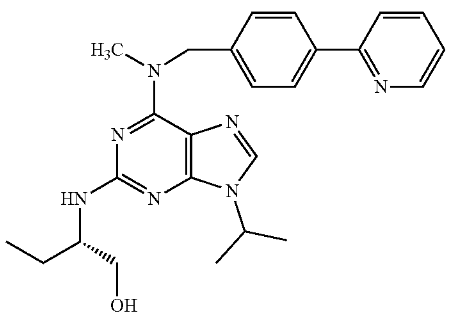 [SMILES: CC[C@@H](CO)Nc1nc(N(C)Cc2ccc(-c3ccccn3)cc2)c2ncn(C(C)C)c2n1] |
| 9 | 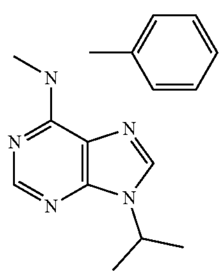 |
| 12 | 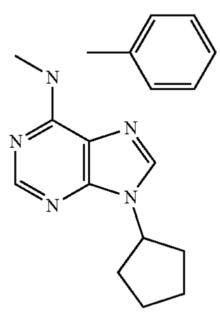 |
| 13 | 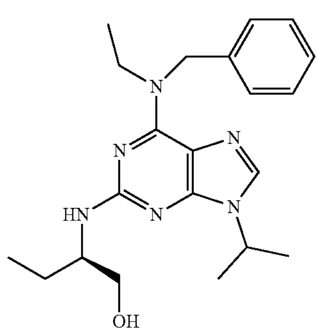 [SMILES: CC[C@H](CO)Nc1nc(N(CC)Cc2ccccc2)c2ncn(C(C)C)c2n1] |
| 14 | |
| 15 | |
| 16 | |
| 17 | |
| 18 | |

TABLE 1-continued
| No | Structure |
|---|---|
| 19 | 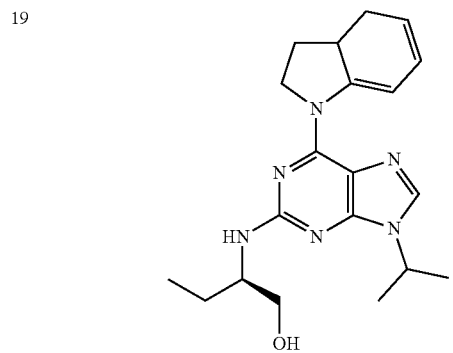 |
| 20 | 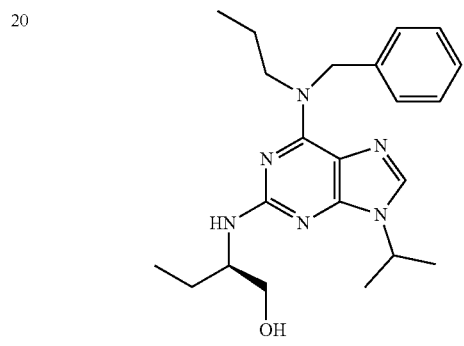 |
| 21 | 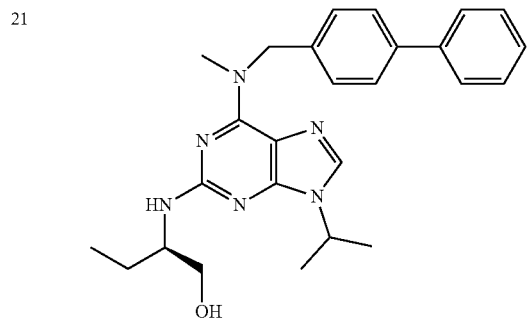 |
| 22 | 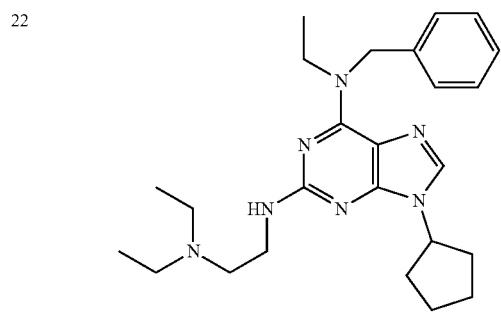 |
TABLE 1-continued
| No | Structure |
|---|---|
| 23 | 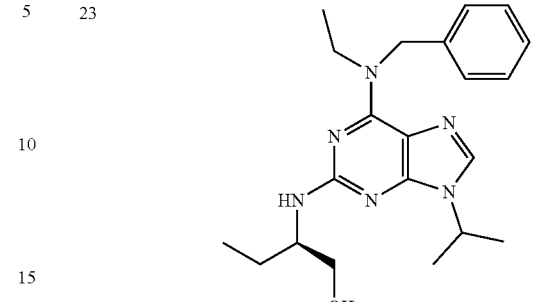 |
| 24 | 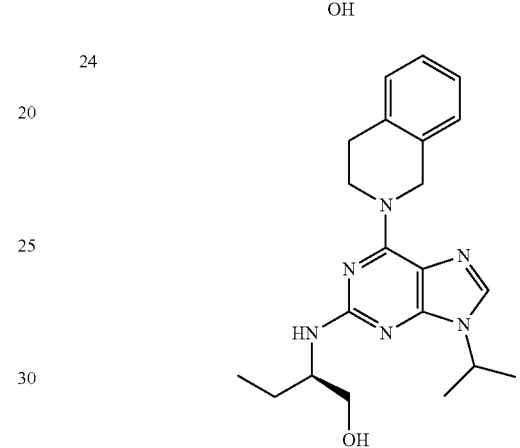 |
| 26 | 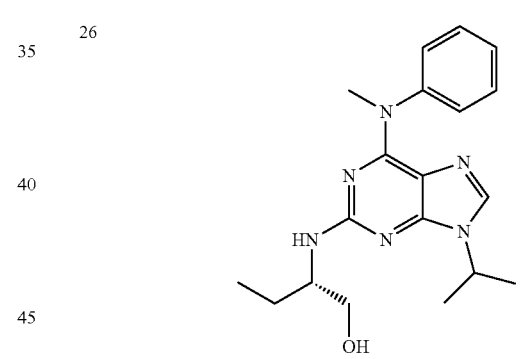 |
| 28 | 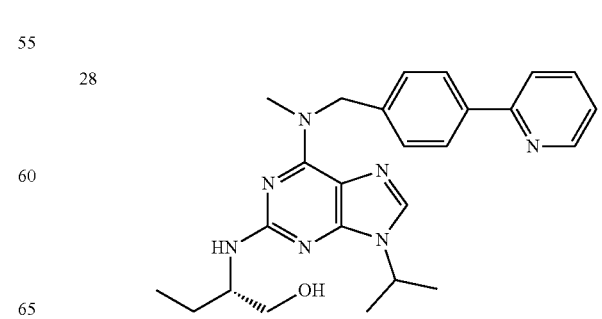 |

TABLE 1-continued

| No | Structure |
|---|---|
| 29 | 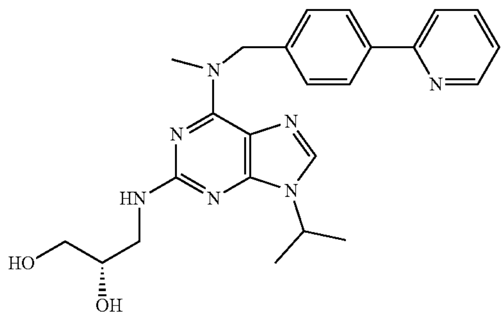 [SMILES: CC(C)n1cnc2c(N(C)Cc3ccc(-c4ccccn4)cc3)nc(NC[C@H](O)CO)nc21] |
| 31 | 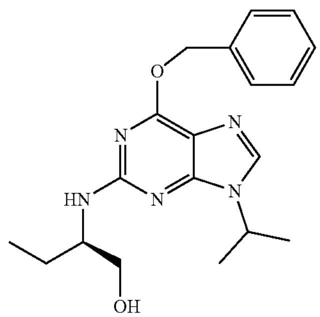 [SMILES: CC[C@H](CO)Nc1nc(OCc2ccccc2)c2ncn(C(C)C)c2n1] |
| 32 | 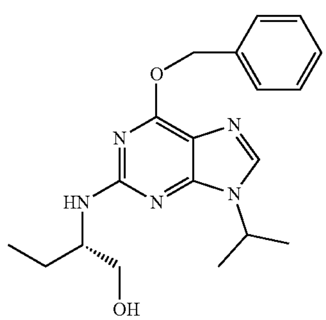 [SMILES: CC[C@@H](CO)Nc1nc(OCc2ccccc2)c2ncn(C(C)C)c2n1] |
| 33 | 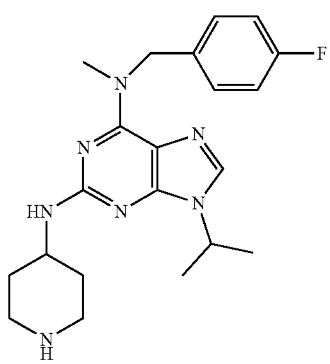 [SMILES: CC(C)n1cnc2c(N(C)Cc3ccc(F)cc3)nc(NC3CCNCC3)nc21] |
| 34 | 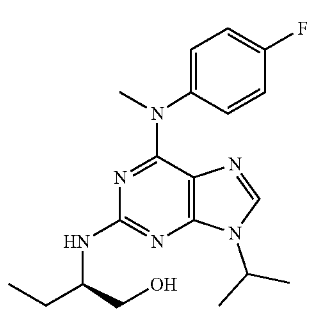 [SMILES: CC[C@H](CO)Nc1nc(N(C)c2ccc(F)cc2)c2ncn(C(C)C)c2n1] |
| 35 | |
| 36 | |
| 37 | |
| 38 | |
| 39 | |

TABLE 1-continued

| No | Structure |
|---|---|
| 40 | 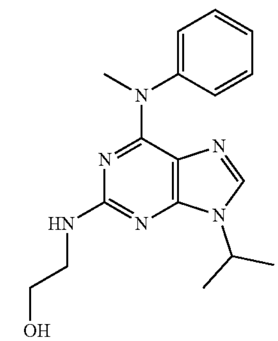 [SMILES: CC(C)n1cnc2c(N(C)c3ccccc3)nc(NCCO)nc21] |
| 41 | 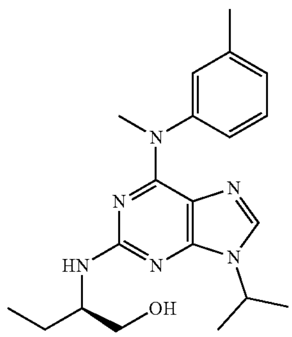 [SMILES: CC[C@H](CO)Nc1nc(N(C)c2cccc(C)c2)c2ncn(C(C)C)c2n1] |
| 42 | 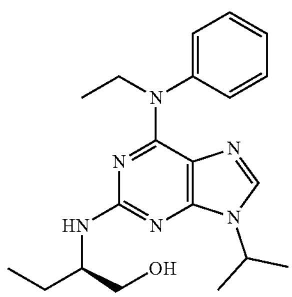 [SMILES: CC[C@H](CO)Nc1nc(N(CC)c2ccccc2)c2ncn(C(C)C)c2n1] |
| 43 | 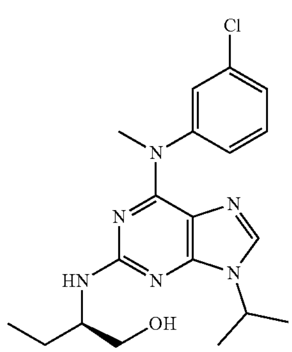 [SMILES: CC[C@H](CO)Nc1nc(N(C)c2cccc(Cl)c2)c2ncn(C(C)C)c2n1] |
| 44 | |
| 45 | |
| 46 | |
| 47 | |

TABLE 1-continued

| No | Structure |
|---|---|
| 48 | 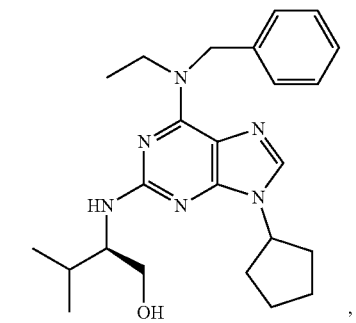 |

According to a preferred embodiment of the present invention, the compound of formula (I) for use as a medicament is selected from those disclosed in Table 1 herein above, and is in particular a compound selected from compound 13, 14, 15, 18, 20, 22, 23, 26, 31, 38 and Aftin-5, and more particularly is Aftin-5.

Illustratively, the compound of formula (I) for use as a medicament is selected from compound of formula:

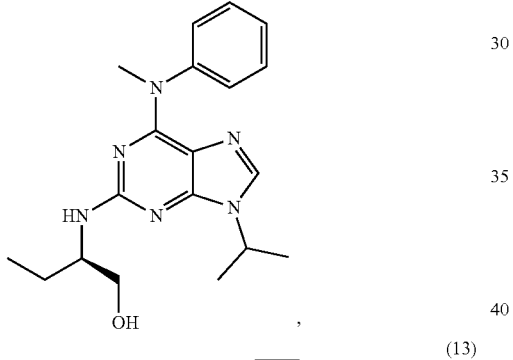

(Aftin-5),

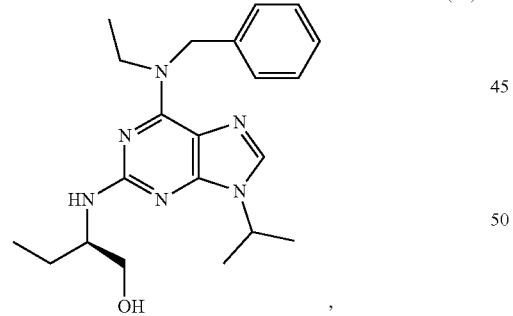

(13),

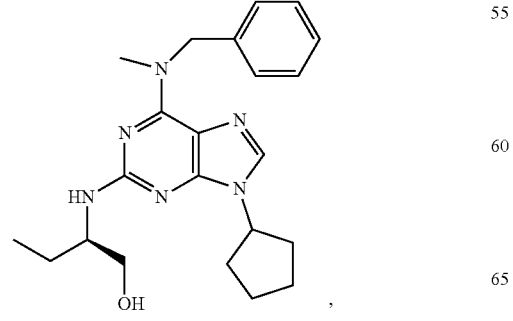

(14),

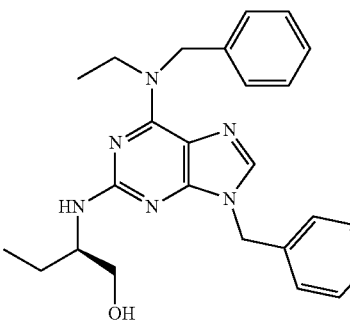

(15),

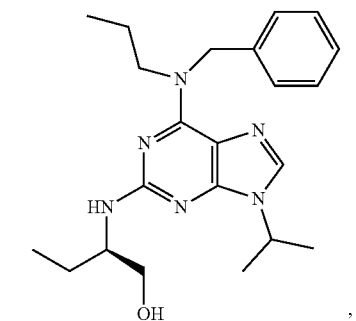

(18),

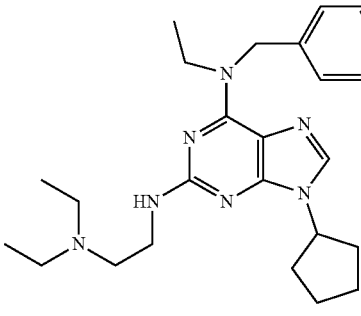

(20),

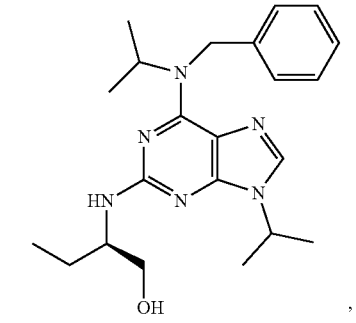

(22), (23),

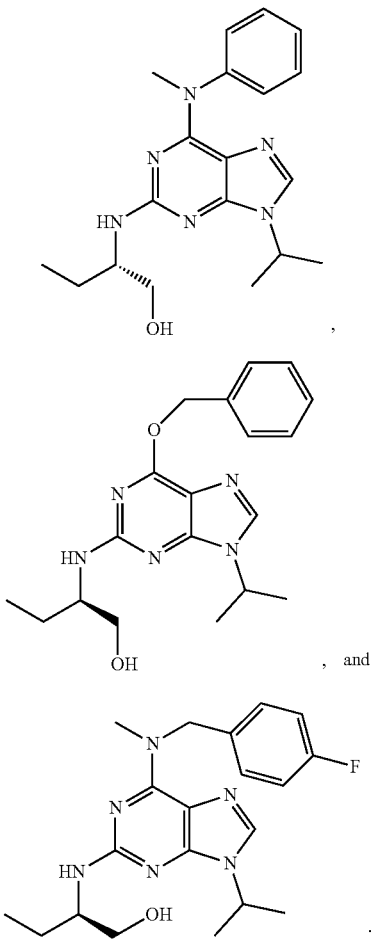

The compounds of formula (I) may be prepared according to any suitable method from the state in the art, e.g. the preparation procedures described in EP 2 664 619 and variant of these procedures, which may be implemented starting from the knowledge of a skilled artisan.

Uses

The compounds of formula (I), any one of the other sub-formulas as defined above or any one of their pharmaceutically acceptable salts may be used in the prevention and/or the treatment of neurodegenerative disorders or neuro-inflammation disorders.

Within the scope of the invention, the term 'prevention' refers to a reduction of the likelihood of the occurrence for an individual to develop a neurodegenerative disorder or a neuro-inflammatory disorder. In said circumstance, the individual may be from the general population or from a specific cohort of individuals presenting at least one risk factor for developing a neurodegenerative disorder or a neuro-inflammatory disorder.

Within the scope of the invention, the term 'treatment' refers to a therapy intended to partially or totally alleviating at least one symptom linked to said neurodegenerative disorder or said neuro-inflammatory disorder. In said circumstance, the individual may be from a specific cohort of individuals diagnosed for having a neurodegenerative disorder or a neuro-inflammatory disorder, or presenting at least one symptom of a neurodegenerative disorder or a neuro-inflammatory disorder.

Therefore, the present invention further relates to a compound of formula (I) as described above, or one of its pharmaceutically acceptable salts, for use in preventing and/or treating a neurodegenerative disorder and/or a neuro-inflammatory disorder.

The present invention further relates to a compound of formula (I) as described above, or one of its pharmaceutically acceptable salts, for use in preventing and/or treating a neurodegenerative disorder selected in a group comprising Alzheimer's disease, Parkinson's disease, Huntington's disease, amyotrophic lateral sclerosis, Down's syndrome, and more particularly Alzheimer's disease.

According to a preferred embodiment of the present invention, the compound of formula (I) selected from those disclosed in Table 1 herein above, or one of its pharmaceutically acceptable salts, in particular a compound selected from compound 13, 14, 15, 18, 20, 22, 23, 26, 31, 38 and Aftin-5, and more particularly is Aftin-5, is for use in the prevention and/or the treatment of Alzheimer's disease.

More particularly, as illustrated in the examples below, the compounds of formula (I), and in particular Aftin-5, are of use for the treatment of Alzheimer's disease (AD) and other neurodegenerative disorders.

As mentioned above, Aftins have been previously considered as compounds being useful to artificially induce the level of $A\beta_{1-42}$ in neuron cells at high dose, which is one among many hallmarks of AD physiopathology. Therefore, because the Aftins were thought to be capable of mimicking AD, they were envisioned to be of use at high dose for in vitro and in vivo screening compounds that modulate the production of $A\beta_{1-42}$ amyloid β peptides.

In other words, the Aftins were thought to be used to screen compounds aimed at treating AD.

On the contrary, as shown in the 'Examples' section below, the inventors unexpectedly found that Aftins may have a positive impact on some of the hallmarks associated with AD, hence favouring the use of Aftin compounds for the prevention and/or the treatment of AD.

AD is known to be multigenic and is likely to be correlated with a wide range of risk factors. Evidence from twin and family studies, however, supports a significant genetic component with heritability between 60% and 74%. Four genes have been associated with early onset familial AD, the amyloid precursor protein gene (APP) and the presenilin genes (PS1 & PS2). However, 98% of AD cases occur after the age of 65. So far only one genetic risk factor for this form of AD has been identified unequivocally, the E4 allele of apolipoprotein E (APOE).

Non-genetic factors constitute the main factors favoring the late onset AD. Age, low education, sedentary life, social & cognitive engagement, adiposity, obesity, hyperinsulinemia, high cholesterol, diabetes, metabolic syndrome, hypertension, heart disease have all been linked to increased AD probability. Despite numerous disclosures linking adiposity/obesity/diabetes and AD, no precise underlying molecular mechanisms have been identified.

a) Aftin-5 does not Induce AD Phenotype

Production of amyloid peptides by sequential catalytic cleavage of APP by β- and γ-secretases is unambiguously associated with familial AD and late onset AD. In particular, production of the aggregation prone amyloid $A\beta_{1-42}$ is increased during AD. An increased $A\beta_{1-42}/A\beta_{1-40}$ ratio is characteristic of AD, while $A\beta_{1-42}$ is one of the dominating peptides in senile plaques (a major AD hallmark). Rather than extracellular plaques, $A\beta_{1-42}$ oligomers most probably represent the toxic forms of amyloids.

Numerous studies have demonstrated the neurotoxicity of Aβ peptides, the Aβ$_{1-42}$ form appearing to be the most aggressive. Because of its high propensity to aggregate, Aβ$_{1-42}$ can be organized in a different ways: monomeric, oligomeric or fibrillar. Despite apparent contradictions in the literature regarding the identification of the really toxic form, recent work shows that the oligomeric form is associated with acute toxicity while the fibrillar form is more chronic. Nevertheless, the mechanisms causing neurotoxicity are yet still poorly understood.

Consistently with previous observations, a compound of formula (I) as described above, or one of its pharmaceutically acceptable salts, e.g. Aftin-5, triggers Aβ$_{1-42}$ increase at high dose, a decrease of Aβ$_{1-38}$ while Aβ$_{1-40}$ remains unchanged (see example 2). Despite in vitro production of Aβ$_{1-42}$ in OHSC, treatment of mice with aftin-5 does not lead to an aggregation of said protein into β-sheets plaques, which is observed in the brain of AD patients (see example 4). Consequently, Aftin-5 does not induce AD phenotype. In addition, Aftin-5 modulates in vitro the production of Aβ products even in the presence of the BMS γ-secretase inhibitor and is not able to induce amyloid aggregates despite the increase of Aβ$_{1-42}$.

In certain embodiments, the invention also relates to a compound of formula (I) for use in treating an individual having an altered production of Aβ$_{1-42}$ protein, in particular an increased production of Aβ$_{1-42}$ protein.

b) Aftin-5 Attenuates the Phosphorylation of Tau and Reduces the Activity of GSK-3β

Other hallmarks of AD are that Tau protein is abnormally phosphorylated and accumulated in the form of neurofibrillary tangles in AD brain.

Unpredictably, Aftin-5 is shown herein to efficiently promote an attenuation of the phosphorylation of Tau protein (see example 5). Since GSk-3β in AD patients is upregulated and accumulates in neurons, the effects of Aftin-5 on GSK-3β in organotypic slice cultures from transgenic mice overexpressing phosphorylated Tau protein were investigated. Very interestingly the data showed that Aftin-5 by promoting an attenuation of the phosphorylation of Tau protein reduces in the meantime the activity of GSK-3β.

In certain embodiments, the invention also relates to a compound of formula (I) for use in treating an individual having an altered level of phosphorylation of Tau protein, in particular an increased level of phosphorylation of Tau protein.

c) Aftin-5 Increases Glucose Metabolism and Increases Post-Synaptic Neuronal Activity Both Aβ peptides production and hyper phosphorylation of Tau have been hypothesized as representing downstream results in response to other cell metabolism dysfunctions. These dysfunctions might include impairment of glucose metabolism, formation of ion channels sensitive to cations, increased production of free radicals, mitochondrial dysfunction, activation of apoptotic pathways, microglial activation or disruption of synaptic functioning resulting in increased glutamate release and reduced liberation of acetylcholine.

Indeed, it was observed that brain glucose utilization declines in individual having AD, and this decline is accelerated during the progression of AD. Most glucose in the brain is metabolized to produce ATP in order to maintain neuronal activity. Approximatively 2-5% of total glucose feeds into the hexosamine biosynthesis pathway to produce glucosamine 6-phospate and UDP-N-acetylglucosamine. UDP-GlcNAc is the donor substrate for O-linked-β-N-acetylglucosamine (O-GlcNAC) transferase (OGT) which catalyses protein O-GlcNacylation.

Further, it has been suggested that Tau protein is modified by O-GlcNac. Thus restoration of the brain glucose metabolism could offer a therapeutic perspective approach for the treatment of AD.

Unexpectedly, Aftin-5 is shown herein to efficiently promote (i) an increase of postsynaptic density protein (PSD95), which is a hallmark of post-synaptic neuronal activity (see example 9) and (ii) an upregulation of insulin/insulin-like growth factor-1 (IGF-1) receptor, involved in glucose metabolism (see example 8).

In certain embodiments, the invention also relates to a compound of formula (I) for use in treating an individual having an altered glucose metabolism, in particular a down-regulation of insulin/insulin-like growth factor-1 (IGF-1) receptor.

In certain embodiments, the invention also relates to a compound of formula (I) for use in treating an individual having an altered post-synaptic neuronal activity, in particular a decreased of postsynaptic density protein (PSD95).

d) Aftin-5 Alleviates Neuro-Inflammation

Emerging evidences suggest that neuro-inflammation is also a key pathological hallmark of AD. Many reports suggest that microglia are attracted to amyloid-β deposits, which they internalize and degrade, contributing to clearance of amyloid-β from the brain. However, during the course of the disease, microglia may lose this beneficial effect as they acquire a 'toxic' phenotype due to chronic activation and continued production of pro-inflammatory mediators. Among numerous inflammatory cytokines associated with the AD, IL-1β appears to play a major role. Therefore, it is likely that attenuation of inflammatory responses could also alleviate cognitive deficits. Indeed, it was suggested that abrogating IL-1β signalling may offer therapeutic benefit to AD.

As shown in the examples section, Aftin-5 has been proved to efficiently downregulate inflammatory mRNA cytokines in organotypic slice cultures from WT mice, such as interleukin-1β and in a less extent IL-6 (see example 7), which are known to be upregulated in the brain and plasma of AD patients. In organotypic slice cultures from transgenic mice overexpressing phosphorylated Tau protein, a significant reduction of IL-1β, TNFα and IL-6 was evidenced (see example 7), as well as down regulation of p38-MAK activation.

In certain embodiments, the invention also relates to a compound of formula (I) for use in treating an individual having an altered production and/or secretion level of pro-inflammatory cytokines, in particular, an upregulated production and/or secretion level of pro-inflammatory cytokines.

e) Aftin-5 Improves Cognitive Performances

It is now accepted that Brain derived Neurotrophic factor (BDNF) is a cyclic AMP-responsive element-binding protein (CREB) target playing a pivotal role in learning and memory. Further, it has also been observed a correlation between a BDNF dysfunction and the physiopathology of AD.

As shown in example 9, Aftin-5 is capable of activating CREB and BDNF.

Altogether, the data showing that Aftin-5 increases the expression of PSD95, BDNF, CREB, IR, IGF-1R and decreases the expression of IL-1β, and in a less extent IL-6, support the fact that Aftin-5 may be involved in improving the learning memory capacity.

In certain embodiments, the invention also relates to a compound of formula (I) for use in treating an individual having an altered cognitive performance, in particular an altered long term and/or short term memory.

It is needless to mention that an alteration, such as an increase or a decrease, of a given parameter in an individual refers to a change of the level or the intensity of said parameter measured in said individual, as compared to the level or the intensity of the same parameter measured in either (1) an healthy individual, (2) an individual that is not considered to be at risk to develop a neurodegenerative disorder and/or a neuro-inflammatory disorder, or (3) an individual that has not developed a neurodegenerative disorder and/or a neuro-inflammatory disorder.

All of the above mentioned parameters, such as Aβ proteins production, aggregation of Aβ proteins, phosphorylation of Tau protein, expression of proteins (e.g. receptors, cytokines, proteins involved in the glucose metabolism or in cognitive capacities) and learning and/or memory capacities, may be measured following the usual standard methods and the common knowledge in the art.

For example, expression of proteins may be measured at the mRNA level (e.g. qPCR, RT-PCR) or the protein level (e.g. Western blotting, immunostaining).

For illustration purposes only, but not limited to learning and/or memory capacities may be measured by the means of a novel object recognition (NOR) test and/or a Y-maze test.

Finally, as shown below, the purine derivatives according to the invention, in particular Aftin-5, present the great advantage of crossing the blood-brain barrier; of entering the brain after intraperitoneal or oral administration; and of entering the brain after chronic subcutaneous injection in rat or oral administration (see example 3).

Therefore, compounds of formula (I) may be formulated in order to enter the systemic route.

As it will emerge from the 'Examples' section below, the experimental data provide converging evidences in favour of the use of a compound of formula (I), such as e.g. Aftin-5, to efficiently target several physiologic alteration observed within the course of AD.

In some embodiments, inflammatory disorders include, without limitation, a central nervous system (CNS) inflammatory disorder, an inflammatory disorder associated with an autoimmune disease, a joint inflammation disorder, an inflammatory bowel disease, viral induced neuro-inflammation, a traumatic brain injury and an inflammatory skin or epithelial disorder.

In some embodiments, a CNS inflammatory disorder may be selected in a group comprising Rasmussen inflammatory disorder, rheumatoid arthritis, multiple sclerosis, optic neuritis, osteoarthritis, atherosclerosis and ankylosing spondylitis.

In certain embodiments, an inflammatory disorder associated with an autoimmune disease may be Sjogren's syndrome.

In certain embodiments, the inflammatory bowel disease may be selected among a Crohn's disease and an ulcerative colitis.

In some embodiments, the inflammatory skin or epithelial disorder may be selected in a group comprising psoriasis, dermatitis, bronchitis and asthma.

The inventors have surprisingly observed that a compound of formula (I) according to the present invention, e.g. Aftin-5, is capable of reducing the expression of pro-inflammatory cytokines, such as e.g. IL-1β, IL-6 or TNF-α (see example 7). Therefore, without wishing to be bound to a theory, the inventors believe that any neuro-inflammatory disorder involving an increased expression of any pro-inflammatory cytokines, such as e.g. IL-1β, IL-6 or TNF-α would benefit from a treatment with a compound of formula (I) as described herein.

The present invention further relates to the use of a compound of formula (I) as described above, or one of its pharmaceutically acceptable salts, for the prevention and/or the treatment of a neurodegenerative disorder and/or a neuro-inflammatory disorder.

In another aspect, the present invention further relates to the use of at least a compound of formula (I), any one of the other sub-formulae as defined above or any one of its pharmaceutically acceptable salts for the manufacture of a pharmaceutical composition intended for preventing and/or treating a neurodegenerative disorder or a neuro-inflammatory disorder, in particular as described above.

The present invention is a disclosure of the use of purine derivatives, in particular Aftin-5 and its analogues, as good candidates for providing a therapeutic approach for the treatment of AD and other neurodegenerative disorders, such as Parkinson's disease, Huntington's disease, amyotrophic lateral sclerosis, Down's syndrome, and neuro-inflammatory disorders, such as a central nervous system (CNS) inflammatory disorder, an inflammatory disorder associated with an autoimmune disease, a joint inflammation disorder, an inflammatory bowel disease, viral-induced neuro-inflammatory disorders, traumatic brain injuries and an inflammatory skin or epithelial disorder.

With respect to the state of the art, the findings of the inventors are totally unexpected and could not be extrapolated or anticipated.

Indeed, Ramzaeva et al. and Baraldi et al. (see above) merely relate to the synthesis of purine compounds.

On another hand, Knockaert et al., Harmse et al. and Oumata et al. (see above) are aimed at providing purine compounds possessing inhibitory activities towards specific kinases.

For example, compounds 95M, 97M and 52M disclosed by Harmse et al., which represent a methylated form of respectively compounds 95, 97 and 52, were assayed for their anti-malaria properties and found to be less active than their non-methylated counterpart compounds. Therefore, compounds 95M, 97M and 52M can hardly be considered as representing good candidates for treating malaria and even for any use as a medicament. Their putative mode of action towards treating and/or preventing a neurodegenerative disorder and/or a neuro-inflammatory disorder remains so far not documented to the knowledge of the inventors.

Finally, none of the teachings from WO 98/05335, WO 01/49688, WO 2002/04450, WO 2002/04451, WO 2004/016612, WO 2008/122767, Rivkin et al., WO 2010/019392 and WO 2013/062762 discloses or suggests the benefit of the disclosed purine derivatives as medicament, in particular, aimed at achieving prevention and/or treatment of neurodegenerative disorders and/or neuro-inflammatory disorders.

For example, compounds P17 and P18 (also referred as P20) disclosed in WO 01/49688, represent compounds having an anti-proliferative activity towards lymphocytes and hematopoietic cell lines, such as macrophage from the bone marrow (KG-1 cell line) or T lymphoblast from the peripheral blood (Molt-3 cell line). However, none of these compounds are specifically discussed or suggested as representing a good candidate for being a medicament. Efficiently and reproducibly treating and/or preventing a neurodegenerative disorder and/or a neuro-inflammatory disorder are furthermore never disclosed therein.

Other features of the present invention will become apparent after review of the specification, claims and drawings.

Methods and Pharmaceutical Compositions

In one aspect, the invention relates to a method for treating and/or preventing a neurodegenerative disorder and/or a neuro-inflammatory disorder in an individual in need thereof, comprising the administration of an effective amount of a compound of formula (I), any one of the other sub-formulae as defined above or any one of its pharmaceutically acceptable salts, optionally in a pharmaceutically acceptable vehicle.

In a still other aspect, the present invention also relates to a method for reducing the likelihood of the occurrence of, and/or treating, a neurodegenerative disorder and/or a neuro-inflammatory disorder in an individual in need thereof, comprising the administration of an effective amount of a compound of formula (I), any one of the other sub-formulae as defined above or any one of its pharmaceutically acceptable salts, optionally in a pharmaceutically acceptable vehicle.

Another aspect of the invention also relates to a pharmaceutical composition comprising (i) a compound of formula (I), any one of the other sub-formulae as defined above or any one of its pharmaceutically acceptable salts, and (ii) a pharmaceutically acceptable vehicle.

Are also encompassed by the present invention, the pharmaceutical composition for use as a medicament and the use of the above described pharmaceutical composition as a medicament.

The formulation of pharmaceutical compositions comprising at least one compound of formula (I) or any one of the sub-formulae as defined above, according to the instant invention may be prepared according to the well-known principles and techniques applicable in the art.

In some embodiments, a suitable pharmaceutically acceptable vehicle according to the invention includes any and all conventional solvents, dispersion media, fillers, solid carriers, aqueous solutions, coatings, antibacterial and antifungal agents, isotonic and absorption delaying agents, and the like.

In certain embodiments, suitable pharmaceutically acceptable vehicles may include, water, saline, phosphate buffered saline, dextrose, glycerol, ethanol and a mixture thereof.

In some embodiments, pharmaceutically acceptable vehicles may further comprise minor amounts of auxiliary substances or excipients such as wetting or emulsifying agents, preservatives or buffers, which enhance the shelf life or effectiveness of the active ingredient. The preparation and use of pharmaceutically acceptable vehicles is well known in the art. The aforementioned excipients are selected according to the dosage form and the desired mode of administration.

With the express exception of any conventional media or agent incompatible with the active ingredient, use thereof in the pharmaceutical compositions of the present invention is contemplated.

In some embodiments, the active agent, e.g. in the form of a pharmaceutic composition may be administered by any suitable route, including enteral (e.g., oral), parenteral, intravenous, intramuscular, intra-arterial, intramedullary, intrathecal, subcutaneous, intraventricular, transdermal, intradermal, rectal, intravaginal, intraperitoneal, topical, mucosal, nasal, buccal, sublingual; by intratracheal instillation, bronchial instillation, and/or inhalation; and/or as an oral spray, nasal spray, and/or aerosol.

In some embodiments, the active agent is administered by oral administration or systemic intravenous administration.

In certain embodiments, the administration of the pharmaceutical composition by injection may be directly performed in the target tissue of interest, in particular in order to avoid spreading of the said active ingredient in the pharmaceutical composition.

Other modes of administration employ pulmonary formulations, suppositories, and transdermal applications.

In some embodiments, an oral formulation according to the invention includes usual excipients, such as, for example, pharmaceutical grades of mannitol, lactose, starch, magnesium stearate, sodium saccharine, cellulose, magnesium carbonate, and the like.

In some embodiments, an effective amount of said compound is administered to said individual in need thereof.

Within the scope of the instant invention, an "effective amount" refers to the amount of said compound of formula (I), which alone stimulates the desired outcome, i.e. alleviates or eradicates the symptoms of the encompassed disorder.

It is within the common knowledge of a skilled artisan to determine the effective amount of a compound of formula (I), as the active ingredient to observe the desired outcome.

Within the scope of the instant invention, the effective amount of the compound to be administered may be determined by a physician or an authorized person skilled in the art and can be suitably adapted within the time course of the treatment.

In certain embodiments, the effective amount to be administered may depend upon a variety of parameters, including the material selected for administration, whether the administration is in single or multiple doses, and the individual's parameters including age, physical conditions, size, weight, gender, and the severity of the disorder to be treated.

In certain embodiments, an effective amount of the active agent may comprise from about 0.001 mg to about 3000 mg, per dosage unit, preferably from about 0.05 mg to about 100 mg, per dosage unit.

Within the scope of the instant invention, from about 0.001 mg to about 3000 mg includes, from about 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg and 2950 mg, per dosage unit.

In certain embodiments, the active agent may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of the individual's body weight per day.

In certain embodiments, each dosage unit may be administered three times a day, two times a day, once a day, every other day, every third day, every week, every two weeks, every three weeks, or every four weeks.

In certain embodiments, the therapeutic treatment encompasses an administration of a plurality of dosage units, including two, three, four, five, six, seven, eight, nine, ten, eleven, twelve, thirteen, fourteen, or more administrations.

In certain embodiments, the treatment of the encompassed disorder may comprise the administration to the individual in need thereof of a compound of formula (I) or any one of the other sub-formulae as defined above, in combination with another compound, in particular a compound known in the art to benefit the individual in need thereof, with respect to the said disorder.

In some embodiments, treatment of AD may be achieved by the administration to the individual in need thereof of a compound of formula (I), any one of the other sub-formulae as defined above or any one of their pharmaceutically acceptable salts in combination with a compound selected in a group comprising donepezil, galantamine, rivastigmine and memantine.

Within the scope of the invention, the expression "an individual in need thereof" is intended to relate to a mammal or non-mammal animal, preferably a mammal, more preferably a human individual.

In some embodiments, said individual presents at least one or more symptoms correlated with a neurodegenerative disorder and/or a neuro-inflammatory disorder.

In some embodiments, said individual has been diagnosed with a neurodegenerative disorder and/or a neuro-inflammatory disorder.

In some embodiments, said individual presents an early stage of a neurodegenerative disorder and/or a neuro-inflammatory disorder.

In some embodiments, said individual presents an advanced or a late stage of a neurodegenerative disorder and/or a neuro-inflammatory disorder.

In some embodiments, said individual presents at least one risk factor of developing a neurodegenerative disorder and/or a neuro-inflammatory disorder.

In some embodiments, the risk factor of developing a neurodegenerative disorder and/or a neuro-inflammatory disorder is selected in a group comprising an altered production of $A\beta_{1-42}$ protein, an altered production of $A\beta_{1-38}$ protein, and altered phosphorylation of Tau protein, an altered production of pro-inflammatory cytokine, an altered glucose metabolism and an altered cognitive ability.

The present invention will be better understood by referring to the following examples and figures which are provided for illustrative purpose only and should not be interpreted as limiting in any manner the instant invention.

EXAMPLES

Example 1—Materials and Methods

1.A—Purine Derivatives According to the Invention

Among compounds of interest the following may be cited: compounds 13, 14, 15, 18, 20, 22, 23, 26, 31, 38 and Aftin-5, as defined above in Table 1.

Table 2 herein after represents control compounds. Compound 10 ((R)-roscovitine) and compound 1 are used herein for comparison only. Compounds 1 and 10 are not encompassed within the compounds according to the invention.

TABLE 2

Control compounds.

| Compound # | Structure |
|---|---|
| 1 | 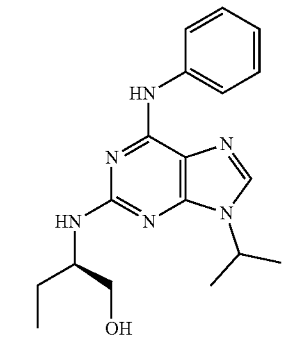 [SMILES: CC[C@H](CO)Nc1nc(Nc2ccccc2)c2ncn(C(C)C)c2n1] |
| 10 (R)-roscovitine | |

1.B—Methods for the Assessment of Translocation of Aftin-5 (See Table 1) and Purine Derivatives into the Brain 1.B.1—Isolation of Rat Brain Endothelial and Glial Cells.

Rat primary BECs and primary glial cells were isolated and cultured as previously described [Lacombe et al., 2011]. Briefly, for BECs, brain tissues were digested enzymatically (1 g/L collagenase/dispase, 20 U/mL DNAse I, 0.147 mg/L TCLK in HBSS, 1 h at 37° C.). A 20% BSA gradient was used for isolation of capillaries. After a second enzymatic digestion, cells were plated in 75 cm² coated culture flasks in EBM medium completed by the EGM-2 MV Single Quots kit (Lonza, Basel, Switzerland). Cultures were maintained at 37° C. in a humidified 5% $CO_2$ atmosphere for 5-6 days before being trypsinized and frozen.

1.B.2—In Vitro Cell-Based Rat Blood-Brain Barrier Model.

Glial cells ($2\times10^4$ cells) were plated on Transwell® plates (Costar, 187 pore size 0.4 Qm; 188 diameter 12 mm; insert growth area 1.12 cm², Dutscher SA, Brumath, France) in glial specific medium (α-MEM/F12) supplemented with 10 Qg ml-1, hEGF, 10 mg ml-insulin, 25 μg ml$^{-1}$, progesterone, 50 mg ml$^{-1}$ transferrin, 50 mg ml$^{-1}$ gentamicin, 50 μg ml$^{-1}$% amphotericin-B, 1% of human serum and 5% of fetal bovine serum. After 24-72 h, BECs ($5\times10^4$ cells) were plated on the upper side of a collagen-coated polyester Transwell® membrane (Costar, pore size 0.4 μm; diameter 12 mm; insert growth area 1 cm²) in 0.5 mL of the endothelial basal medium-2 (EBM-2, LONZA, Walkersville, Md., USA) containing 0.1% human recombinant epidermal growth factor (hEGF), 0.04% hydrocortisone, 0.1% human recombinant insulin like growth factor, 0.1% ascorbic acid, 0.1% gentamicin, 0.1% amphotericin-BN and 5% fetal bovine serum (0.5 mL). The chambers containing human glial cells and brain endothelial cells were considered as the basolateral and apical compartment, respectively. The microplates were then incubated at 37° C. in a 5% $CO_2$ atmosphere. Under these experimental conditions, brain endothelial cells formed a confluent monolayer within 15 days. The integrity of the cell-based BBB models was demonstrated (i) by assessing the presence of tight junctions between the endothelial cells under a confocal microscope, mRNA transcriptional profiles and (ii) by measuring the flux of the paracellular reference marker, [$^{14}$C]-sucrose, through the monolayer.

1.B.3—Analyze of Aftin-5 Translocation Across the Cell Based-BBB Model.

After checking BBB integrity, Transwells® with BEC monolayers were transferred to new plates. T buffer (150 mM NaCl, 5.2 mM KCl, 2.2 mM $CaCl_2$, 0.2 mM $MgCl_2$, 6 mM $NaHCO_3$, 2.8 mM glucose and 5 mM Hepes) was added 1.5 mL to the basal chamber (B) and 0.5 ml to the apical chamber (A). Experiments were performed in triplicate for each compound. The compounds (10 µM) were introduced in the donor chamber (either the apical or the basal compartment). After 60 minutes, aliquots were removed from the acceptor and basal chambers for drug concentration determination as previously described (Lacombe et al., 2011). The Papp value was calculated as followed: Papp=dQ/dT× A×C0 (1) where dQ/dT: amount of drug transported per time-point; A: membrane surface area; Co: donor concentration at time-point 0. Data are presented as the average±S.D. from three monolayers. Mass balance of all compounds was between 80% and 120%. The mass balance was calculated as follows: R (%)=([(Ap+Bs)/A0]×100 (2) where Ap and Bs are the amount of tested compounds in the apical and basal compartments, respectively. A0 is the initial amount in the donor compartment.

1.C—In Vitro Aβ Amyloid Modulation

1.C.1—Neuronal Primary Culture.

Hippocampi and cortex were dissected in HBSS containing 5 mM glucose (dissection medium). The medium was replaced 0.05% trypsin-0.5 mM EDTA (Life Technologies) and hippocampi and cortex were digested separately for 15 min at 37° C. After removing the trypsin, hippocampi and cortex were washed in dissection medium, and incubated in HBSS containing trypsin inhibitor (2 mg/ml, Sigma) and DNAseI (0.05%, Sigma) for 3 minutes at 37° C. Hippocampi and cortex were washed in dissection medium, taken up in few ml of dissection medium and gently triturated by passing through a 1 mL ART® filter tip. Cells were counted and seeded at a density of 22,000 per $cm^2$ for hippocampal neurons and $10^5$ per $cm^2$ for cortical neurons into 24 wells culture plates (Costar) in plating medium (DMEM medium containing 10% heat-inactivated horse serum (Life Technologies)). Wells contain acid-washed glass coverslips (14 mm diameter, Marienfeld, Germany) that had been pre-coated with 50 µg/ml poly-D-lysine (Sigma). The cultures were left to attach at 37° C. with 5% $CO_2$. After 2 h, the plating medium was replaced with Neurobasal containing 2 mM glutamine, 1 mM sodium pyruvate, 10 U/mL penicillin and streptomycin, and 2% B27 supplement (Life Technologies) (culture medium). After 4 days, cytosine arabinoside (3 µM) (Sigma) was added to suppress glial cell proliferation. Cultures were fed twice a week by adding quarter a volume of fresh culture medium.

1.C.2—Organotypic Hippocampal Slice Cultures.

Organotypic hippocampal slice cultures (OHSC) were prepared from newborn (P0-P3) $C_{57}$B16 or for transgenic 3×Tg-AD mice and were cultured according the interface method (Gogolla et al., 2006). OHSC were kept for 7 days in vitro (div) at 37° C. in a humidified atmosphere (5% CO2) before treatment. Medium was changed every other day.

1.D—Cells and mice preparation for immunostaining assays

1.D.1—In Vitro Aftin-5 Effects on Extracellular Aβ Production in Neurons and Organotypic Hippocampal Slice Culture.

For acute exposure, neurons were exposed to various concentration of Aftin-5 for 18 hours for acute exposure. For chronic exposure, OHSC cultures were exposed to Aftin-5 (100, 150 µM) for 18 hours or 10 days.

1.D.2—In Vivo Effects of Aftin-5 on Aβ Extracellular Production and Tau Phosphorylation in Mice.

C57B1 were exposed subcutaneously to Aftin-5 using osmotic minipumps (Alzet® model 2001, 1 µL/h; Saint-Germain-Nuelles, France). Aftin-5 was dissolved in in DMSO:propylene glycol:ethanol (45:45:10). Mice were treated with 1, 3 or 30 mg/Kg for 28 days. Filled pumps were left in saline overnight at 37° C. for priming. Mice were anesthetized with isoflurane (3-4% v/v, 1.5 mL/min) in an induction chamber and maintained under anesthesia through a mask. Mice were shaved on their back, disinfected and an incision made between the scapulae for pump implantation and finally closed with clips. 1% lidocaine gel was applied over the incision for local analgesia. Animals recovered from anesthesia in heated pads and immediately returned to the cages.

1.E—Immunostaining

1.E.1—Fluorescent Western Immunoblotting.

Cells were lysed in freshly prepared lysis buffer containing in mM: Tris-HCl 50, EDTA 2, EGTA 2, NaCl 100, SDS 0.2%, Triton X-100 1%, proteases inhibitors (Roche Protease Inhibitor Cocktail #04693116001), phosphatases inhibitors (in mM: ammonium molybdate 0.1, β-glycerophosphate 20, NaF 50, Na-pyrophosphate 10, Orthovanadate 1). Protein concentration was measured by the Bradford assay and Laemmli buffer was added to each lysate. Proteins (10 µg per lane) were resolved on 12% Nu-PAGE (LifeTechonoliges #NP0342BOX) using MOPS SDS running buffer and transferred on Immobilon-FL PVDF membrane (Millipore #IPFL00010). Membranes were blocked one hour in TBS Tween20 0.1% BSA 5% at room temperature. Primary antibodies were incubated O/N at 4° C. and detected by Alexa 488 conjugated secondary antibodies (Life Techonologies #A11034 and A11029) diluted 1:1.000 in TBS Tween20 0.05% and 1% BSA. The antibodies specific for pThr212-Tau (Abcam #ab4842), pThr181-Tau (AbCam #ab75679), Tau (Millipore #MAB361), APP (Millipore #07-667) and Actin (Millipore #MAB1501) were diluted in TBS Tween20 0.05% and 1% BSA. Fluorescent signal was visualized with the VersaDoc™ Imaging System (Bio-Rad Laboratories) and quantified with Quantity One® Analysis Software. Grey levels measured for bands of interest were normalized to the corresponding actin bands.

1.E.2—Immunocytochemistry.

Cells were fixed with freshly prepared 4% paraformaldehyde, 4% sucrose, PBS for 8 min at room temperature (RT), permeabilized with PBS 0.3% Triton X-100 at RT for 10 min and incubated in PBS 2% goat pre-immune serum (GPI) and 1% BSA at RT for 1 h. Primary antibodies were incubated in PBS 2% GPI and 1% BSA at RT O/N at 4° C. and detected by Alexa conjugated secondary antibodies (LifeTechonologies #A11034, A11029, A11037, and A11032; 1:1.000) in PBS 2% GPI and 1% BSA at RT for 1 h. DAPI was added with secondary antibodies at 0.5 µg/mL. Coverslips were mounted on slides in Mowiol medium (Calbiochem 475904). Images were captured with a Leica inverted microscope and processed with Metamorph® Microscopy Analysis Software (Molecular Devices).

1.F—Amyloid Aβ Quantification
1.F.1—Aβ Quantification in OHSC

All Aβ peptides assays in the samples were performed using V-PLEX Aβ Peptide Panel 1 (4G8) Kit (MSD Technologies_K15199E-1). All plates were read on the SECTOR Imager 2 400 (MSD Technologies). The Aβ peptides assay is based on the principle of the sandwich immunoassay. All assays have followed strictly the protocol kit and all reagents were from Meso Scale Discovery. Briefly, a 96-well plate having 4 spots pre-coated with the corresponding antibodies is provided by MSD Technology (4-spot MULTI-SPOT plates). Before adding the samples, a first saturation step is required. Once the plate is satured and washed, 25 μL of sample (or calibrators) per well are loaded, then 25 μL of the Detection Antibody solution (MSD SULFO-TAG). The plate is incubated for 2 hours. At the end of the incubation, the plate is washed and then a chemical solution (Read buffer 2×) is added allowing electrochemiluminescence. After a short incubation (5 min) at room temperature, the plate is read on the SECTOR Imager 2400. The instrument measures the intensity of the light electrochemiluminescence.

1.F.2—Aβ Amyloid Quantification in the Brain

For determination of total Aβ40 or Aβ42, or Aβ38, forebrain homogenates were extracted for 15 min at 4° C. with 70% formic acid according the method described elsewhere (Abramowski et al., 2008).

1.G—Tau Quantification

Tau and P-Tau in primary rat neurons, organotypic hippocampal slice cultures from wild type (WT) and transgenic Tau mice (3 Tg) after by Aftin-5. Tau was quantified by sandwich immunoassay using the Meso Scale Discovery technologies. Briefly, a 96-well plate having 4 spots pre-coated with the corresponding antibodies is provided by MSD Technology (4-spot MULTI-SPOT plates). Before adding the samples, a first saturation step is required. Once the plate is satured and washed, 25 μL of sample (or calibrators) per well are loaded and incubated for 1 hour. Then the plate is washed and incubated with 25 μL of the Detection Antibody solution (MSD SULFO-TAG) for 1 hour. At the end of the incubation, the plate is washed and then a chemical solution (Read buffer 1×) is added allowing electrochemiluminescence. After a short incubation (5 min) at room temperature, the plate is read on the SECTOR Imager 2400. The instrument measures the intensity of the light electrochemiluminescence.

1.H—Gene Expression Assessment by Total RNA Extraction and Real Time-Quantitative PCR (RT-qPCR)

The impact of Aftin-5 on gene expression of different biomarkers was determined by measuring mRNA levels of selected BDNF, CREB, PS95, INS Receptor/IGF-1 receptor, IL-1β, IL-6 in OHSC treated chronically with Aftin-5 or in a total brain from mice exposed to Aftin-5 at either 8 or 30 mg/Kg. Total RNA was extracted with TRIzol@ reagent and purified on RNeasy® minikit columns (Qiagen, Courtaboeuf, France). Briefly, cells were lysed with 0.5 mL of TRIzol@ reagent by pipetting. After addition of 100 μL of chloroform, mixtures were centrifuged at 10000 g for 15 min at 4° C., supernatants mixed with 600 μL of 70% ethanol and loaded onto RNeasy® columns. Total RNA was washed and eluted with RNase-free water according to manufacturer's protocol and stored at −80° C. RNA concentration was measured spectrophotometrically at 260 nm in a NanoDrop 2000c (Thermo Scientific, Villebon-sur-Yvette, France) (sample A260 nm/A280 nm ratios over 1.8 indicated reduced genomic DNA contamination). cDNAs were synthesized from 0.5 μg of total RNA with RT$^2$ First Strand kit (Qiagen, Courtaboeuf, France) according to the manufacturer's protocol and stored at −80° C. For qPCR, 1 μL of cDNA was mixed with 11.5 μL of 2× RT$^2$ SYBR® green Mastermix (Qiagen, Courtaboeuf, France) and completed to 25 μL with milli-Q water. Mixes were loaded onto customized FAST plates (Life Technologies, Villebon-sur-Yvette, France) containing primers of each gene and the qPCR reactions were performed in a 7900HT Fast Real-Time PCR System (Applied Biosystems, Villebon-sur-Yvette, France) with the following cycle conditions: 95° C. for 10 min, 40 cycles of 15 sec at 95° C. followed by 1 min at 60° C. Threshold cycles (Ct) of target gene and cyclophilin A (Ppia–control housekeeping gene) were recorded and gene expression was calculated as $2^{-\Delta\Delta Ct}$ ($\Delta\Delta Ct=\Delta Ct_{treated}-\Delta Ct_{control}$, $\Delta Ct=Ct_{target}-Ct_{Ppia}$). Specificity of PCR reactions was confirmed by melting curve analysis.

1.I—Cognitive Deficit Assessment
1.I.1—NOR Test.

The NOR test is a test to assess the medium-term non-spatial memory (object). This test takes place in 3 sessions: the Open Field, the Familiarization session and the Test session. The first session allows the habituation of the mouse to the arena. The mouse is placed in the empty arena for 15 min. During this session, the velocity, locomotor activity and anxiety of the mouse are checked. The second session is to familiarize the animal with objects. For this, 24 hours after the Open Field, the mouse is placed in the arena containing two identical objects. The mouse will explore the arena and the two objects placed in the center for 10 min. Finally, after an interval of pre-established time (24 hours), the mouse is placed again in the same arena. In this arena, one of the objects has been replaced by another. So, there are a familiar object (FO) and a novel object (NO) in the center of the arena. The mouse will naturally tend to explore the novelty. The exploration time of the NO versus the FO therefore evaluates the medium-term memory.

$$\text{Sniffing time (\%)} = \frac{FO}{NO+FO} \times 100 \text{ or } \frac{NO}{NO+FO} \times 100$$

$$\text{Discrimination Index} = \frac{NO-FO}{NO+FO}$$

1.I.2—Y-Maze.

The spontaneous alternation test (Y maze) is a test to evaluate the short-term memory (working memory) of the animal. This test is carried out in a Y-maze with arms customized by different forms; squares (A), triangles (B) and lines (C). The mouse is placed in one of the arms for 8 min. In this test, the mouse is free to explore spontaneously the three arms of the Y-maze (FIG. 1).

During the session, the number of entries of each arm of the Y-maze is counted. At the end of the session, the number of possibility (number of total entries in the arms) and the number of spontaneous alternation are calculated. An alternation is defined by consecutive entries in the three different arms (A-B-C).

$$\text{Alternation (\%)} = \frac{Nb \text{ of alternation}}{\text{Total } nb \text{ of arm entries}} \times 100$$

A mouse with a normal phenotype will tend to explore the novelty. Thus, the percentage of alternation will be higher in a mouse without impairment in working memory.

Example 2—Effect of Aftin-5 on Amyloid Proteins Production in OHSC

Figure 2A:
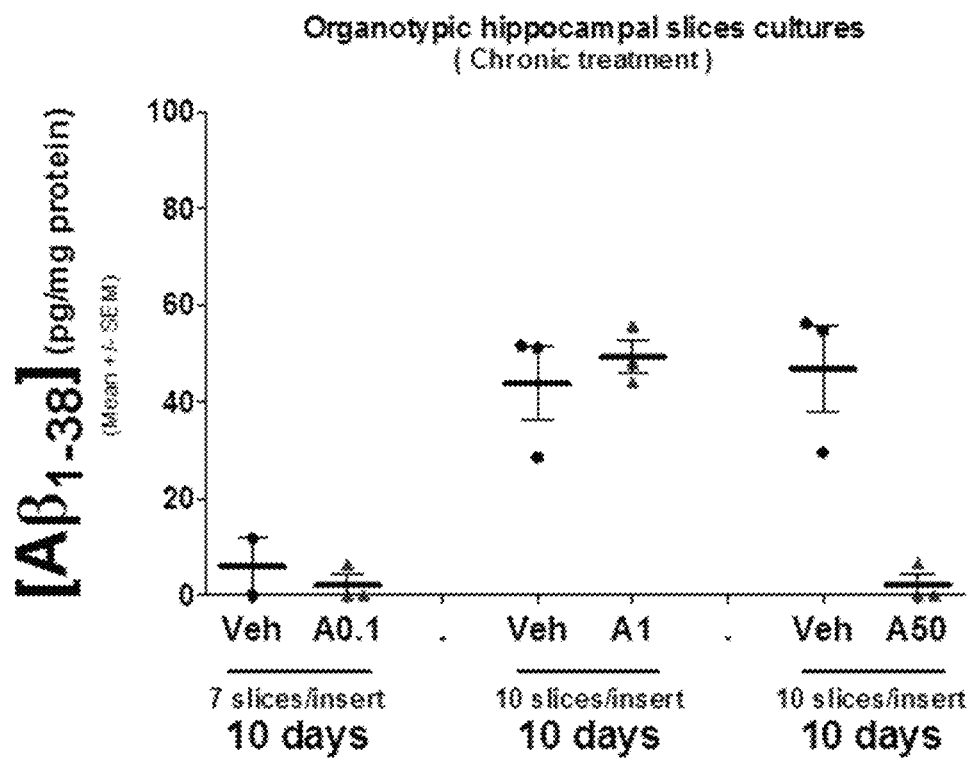
FIG. 2. Plots illustrating the effect on extracellular Aβ production in organotypic hippocampal slice cultures treated for 10 days with Aftin-5 at different concentrations. Culture media of slices were replaced by incubation medium containing Aftin-5 at 0.1 µM (A0.1), 1 µM (A1) or 50 µM (A50) or vehicle (0.1% DMSO; Veh). 10 days later, $A\beta_{1-38}$ (A), $A\beta_{1-40}$ (B) and $A\beta_{1-42}$ (C) were quantified by sandwich immunoassay using the Meso Scale Discovery technology. The concentration ratio $A\beta_{1-42}/A\beta_{1-40}$ is depicted in (D). Extracellular Aβ concentrations were expressed versus total proteins concentration. Data expressed as means+/−SEM from q=3 independent experiments with n=3 inserts/condition and 10 slices/insert.
Figure 2B:
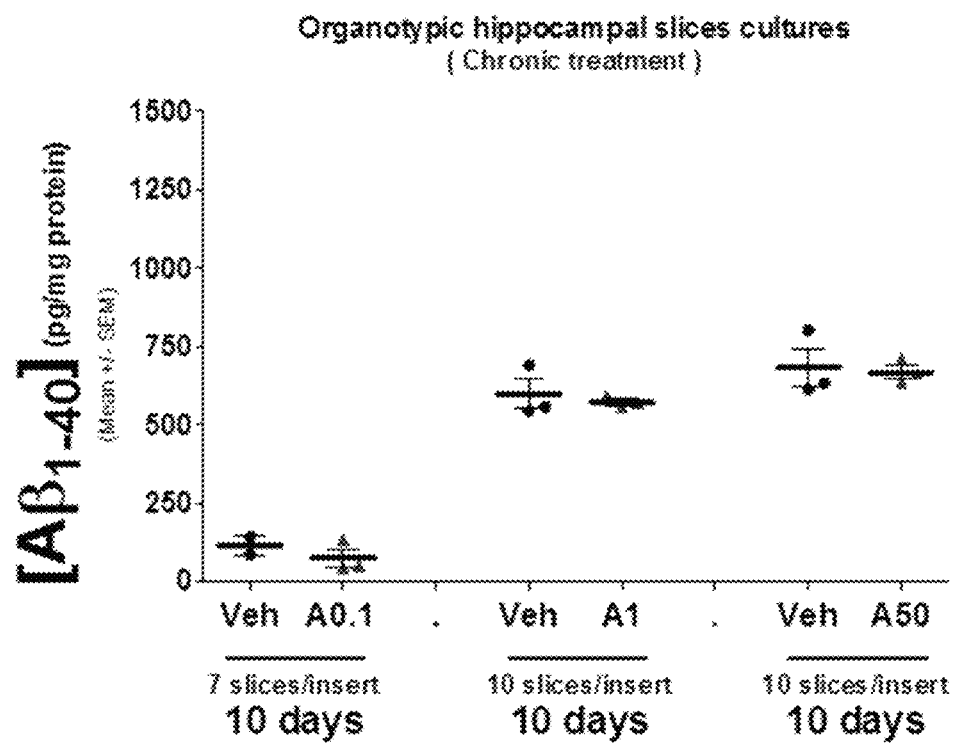
Figure 2C:
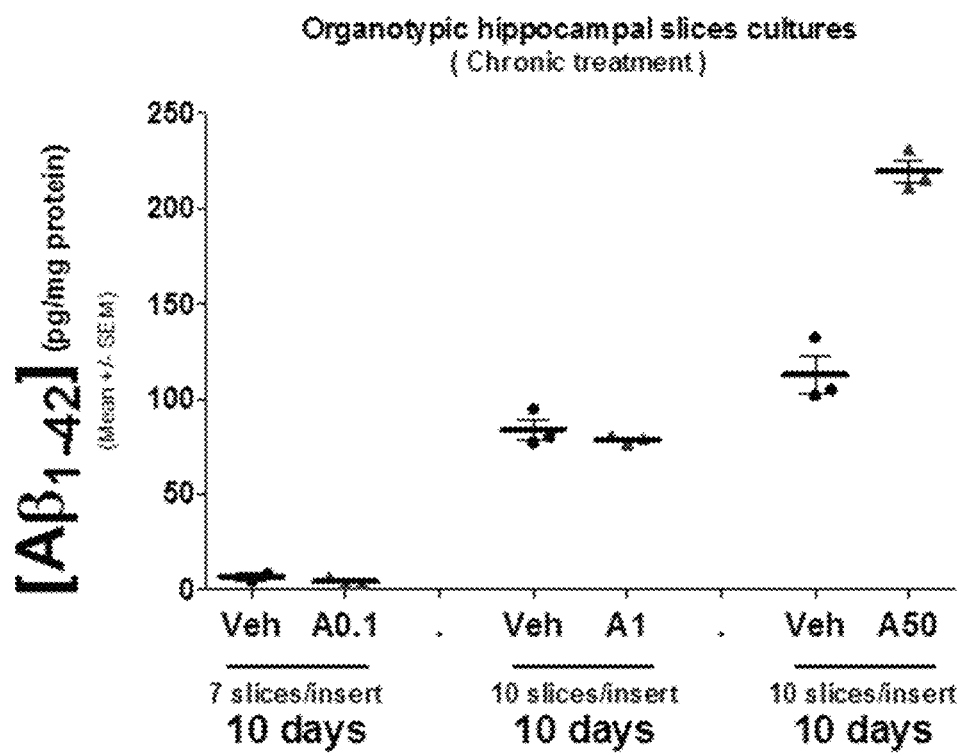
Figure 2D:
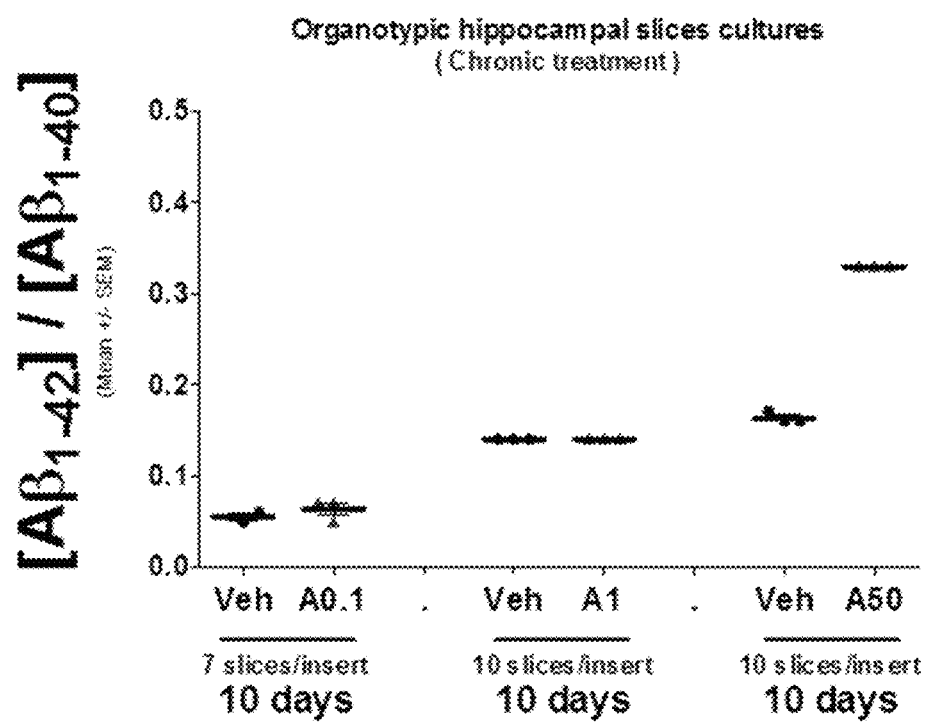
Figure 3A:
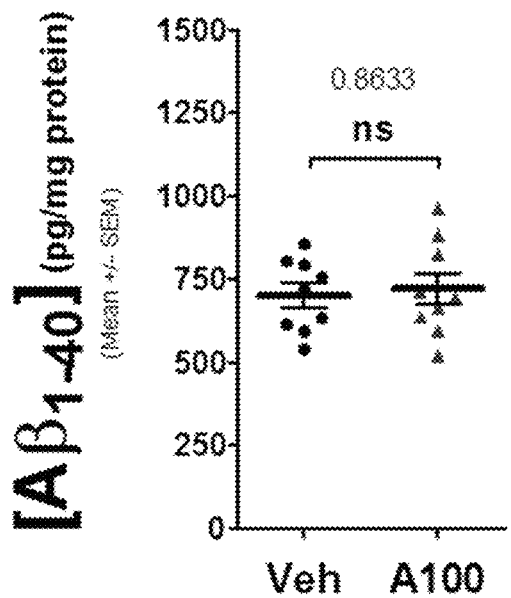
FIG. 3. Plots illustrating the effect of Aftin-5 chronic exposure on extracellular Aβ production in organotypic hippocampal slice cultures. Culture media of slices were replaced by incubation medium containing Aftin-5 at 100 µM (A100) or vehicle (0.1% DMSO; Veh). 10 days later, $A\beta_{1-40}$ (A) and $A\beta_{1-42}$ (B) were quantified by sandwich immunoassay using the Meso Scale Discovery technology. The concentration ratio $A\beta_{1-42}/A\beta_{1-40}$ is depicted in (C). Extracellular Aβ concentrations were expressed versus total proteins concentration. Mann-Whitney tests were performed and ***p<0.001 indicates significant differences between Aftin-5 and control conditions. Data expressed as means+/− SEM from q=3 independent experiments with n=3 inserts/condition and 10 slices/insert.
Figure 3B:
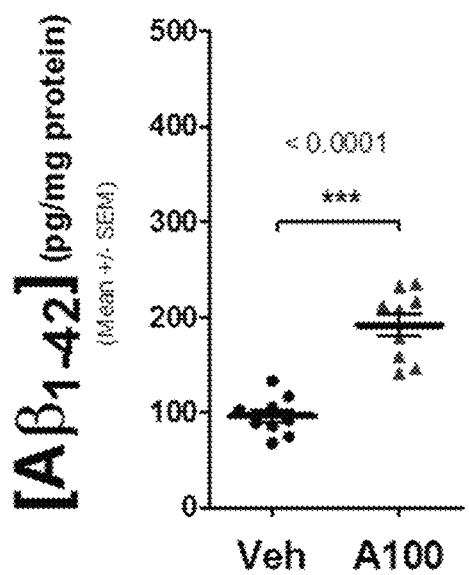
Figure 3C:
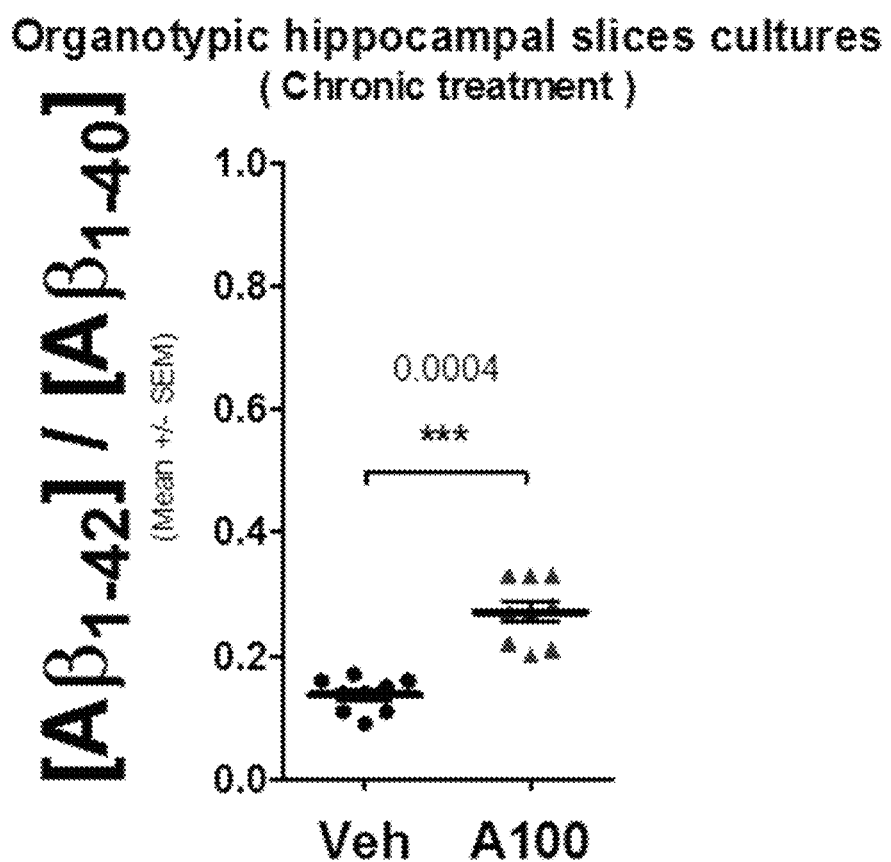

Chronic treatment of OHSC by Aftin-5 leads to an increase in the production of $A\beta_{1-42}$ (P<0.0001) (FIGS. 2C, 3B) and a decrease of $A\beta_{1-38}$ (FIG. 2A) while $A\beta_{1-40}$ remained unchanged (FIGS. 2B, 3A) and a slight but significant increase in the concentration ratio $A\beta_{1-42}/A\beta_{1-40}$.

Figure 4A:
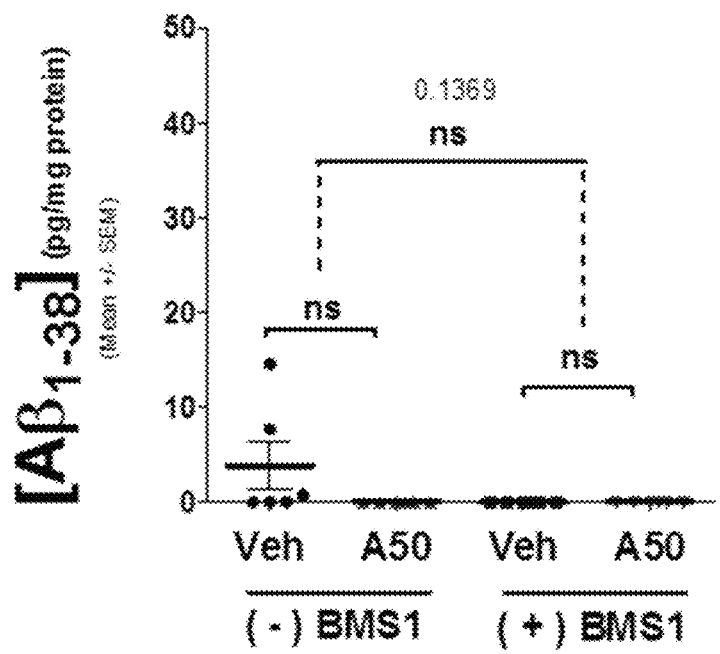
FIG. 4. Plots illustrating the effect of Aftin-5 and BMS on extracellular Aβ production in organotypic hippocampal slice cultures (OHSC). Culture media of OHSC were replaced by incubation medium containing Aftin-5 (50 µM; A50) or vehicle (0.1% DMSO; Veh) without ((−) BMS1) or with 1 µM γ-secretase inhibitor BMS ((+) BMS1). 10 days later, $A\beta_{1-38}$ (A), $A\beta_{1-40}$ (B) and $A\beta_{1-42}$ (C) were quantified by sandwich immunoassay using the Meso Scale Discovery technology. The concentration ratio $A\beta_{1-42}/A\beta_{1-40}$ is depicted in (D). Extracellular $A\beta$ concentrations were expressed versus total proteins concentration. Two-way ANOVA and Bonferroni post-hoc tests were performed and p<0.01 or *p<0.001 indicates significant differences between Aftin-5 and control conditions. Data expressed as means+/−SEM from q=2 independent experiments with n=3 inserts/condition and 10 slices/insert.
Figure 4B:
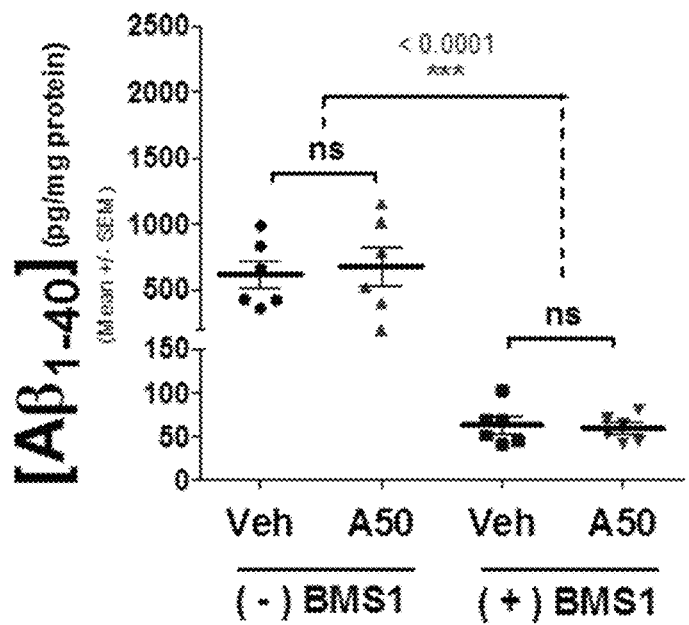
Figure 4C:
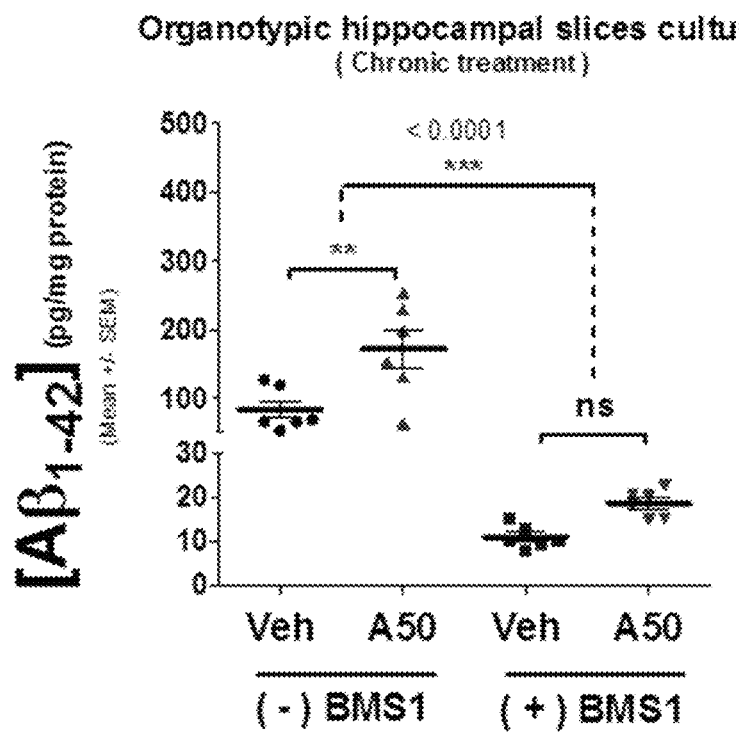
Figure 4D:
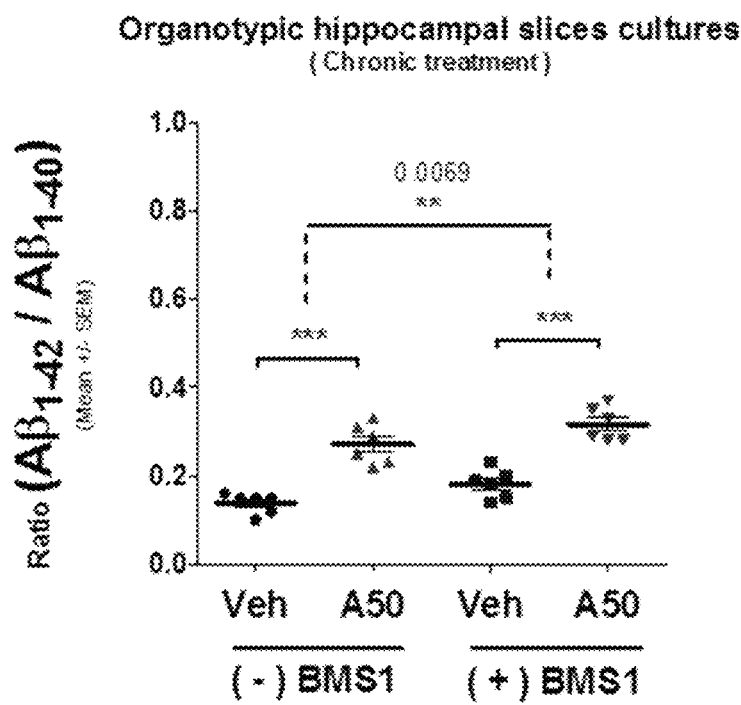

Moreover in AD, the molecular mechanisms underlying the selective Aβ production is a result of changes in γ-secretase activity on transmembrane section of 99 amino acids-long C-terminal fragment of amyloid precursor protein (APP) leading to a decrease and increase in $A\beta_{1-40}$ and $A\beta_{1-42}$ production, respectively. Generally speaking γ-secretase inhibitor reduced the production of $A\beta_{1-42}$ and $A\beta_{1-40}$ and therefore the ratio $A\beta_{1-42}/A\beta_{1-40}$. Treatment of OHSC with γ-secretase inhibitor, BMS (10 μM) revealed no changes in the modulation of $A\beta_{1-42}/A\beta_{1-40}$ ratio induced by Aftin-5 (FIG. 4D). Thus, Aftin-5 is not a modulator of γ-secretase activity.

Example 3—Brain Penetration of Aftin-5

The transport of Aftin5 across the in vitro cell based rat BBB model was performed. The in vitro cell based BBB model was used to investigate a possible translocation of Aftin-5 across the cell monolayer. Sucrose measurement permeability (Papp: 3.28 (0.82 cm·s$^{-1}$×10$^{-6}$ after 7 days of co-culture indicated a well tight monolayer. Having demonstrated the integrity of the cell monolayer, we investigated the ability of Aftin-5 to reach the brain. We demonstrated that Aftin-5 crosses the BBB with the apparent permeability value of about 35 cm·s$^{-1}$×10$^{-6}$. The Papp of Aftin-5 was not significantly different to the Papp value of memantine, another compound used in the treatment of AD.

In addition, pharmacokinetic experiments of Aftin-5 in mice confirmed the ability of the compound to reach the brain. The PK parameters are plotted in Table 3 below.

| Route | $C_{max}$ (nM) | $T_{max}$ (h) | $AUC_{0-\infty}$ (nMh) | $t^{1/2}$ (h) |
|---|---|---|---|---|
| Plasma PO | 3890 | 0.25 | 8111,187 | 1.9 |
| Brain PO | 44.93 | 0.25 | 115.25 | 1.8 |
| Plasma IP | 22564.50 | 0.083 | 13577.63 | 1.2 |
| Brain IP | 807.41 | 0.083 | 441.51 | 0.6 |

After oral administration (PO; single dose 5 mg/kg) or IP administration (single dose 10 mg/kg) to mice Aftin-5 was found to diffuse in the mice brains. $C_{max}$ in plasma was 3890 nM and 22564.50 nM for oral and IP administration, respectively. The terminal elimination half-life ($t^{1/2}$) was about 1.9 h and 1.2 h for oral and IP administration, respectively. The $C_{max}$ brain after oral administration was about 44.93 nM of tissue and about 807.41 nM of brain tissue for IP administration. The brain/plasma partition coefficient ($K_{pbrain/plasma}$) was about 0.014 and 0.033 for oral and IP administration, respectively.

Figure 5A:
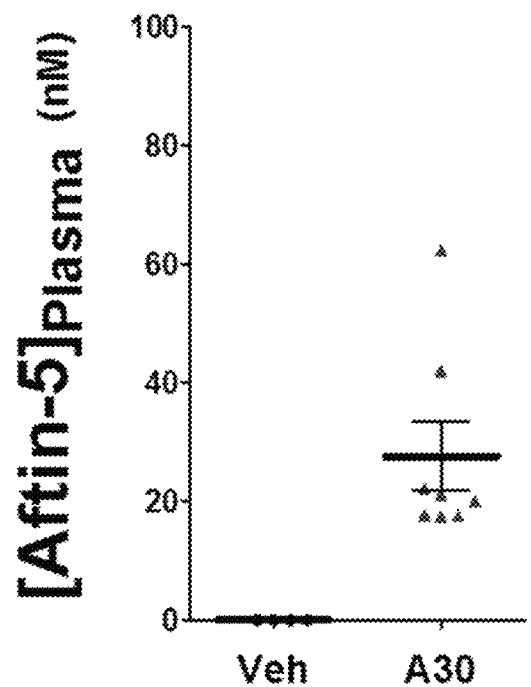
FIG. 5. Plots illustrating the effect of brain and plasma exposure after chronic subcutaneous administration of Aftin-5 to C57Bl6J mice. Due to short Aftin-5 elimination half-time, C57Bl/6J mice were exposed subcutaneously to Aftin-5 (30 mg/kg) or vehicle (DMSO/PEG) during 28 days through an Alzet osmotic pump (pump 1004, Q=0.14 μL/hrs). Plasma was collected at different time points and 28 days after, both brain tissue and plasma were collected. Aftin-5 were extracted and quantified by LC-MS/MS (Quattro Premier). Aftin-5 concentrations in plasma (A) and brain (B) were expressed in nM. Data expressed as means+/−SEM from one experiment with n=4-5 mice/condition.
Figure 5B:
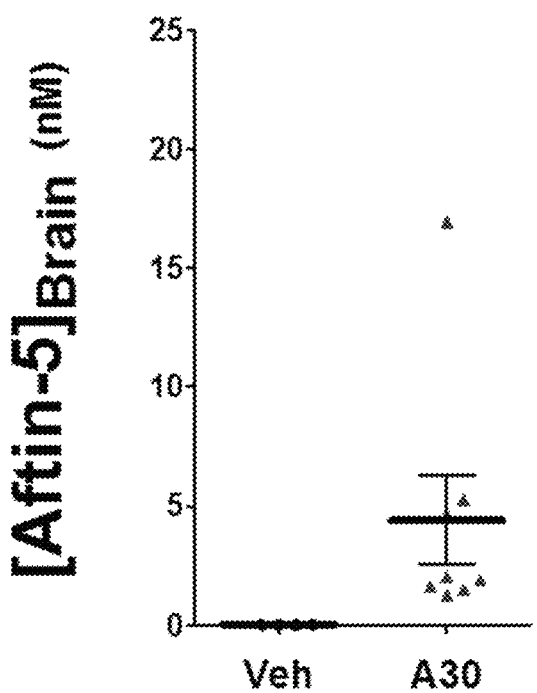
Figure 6A:
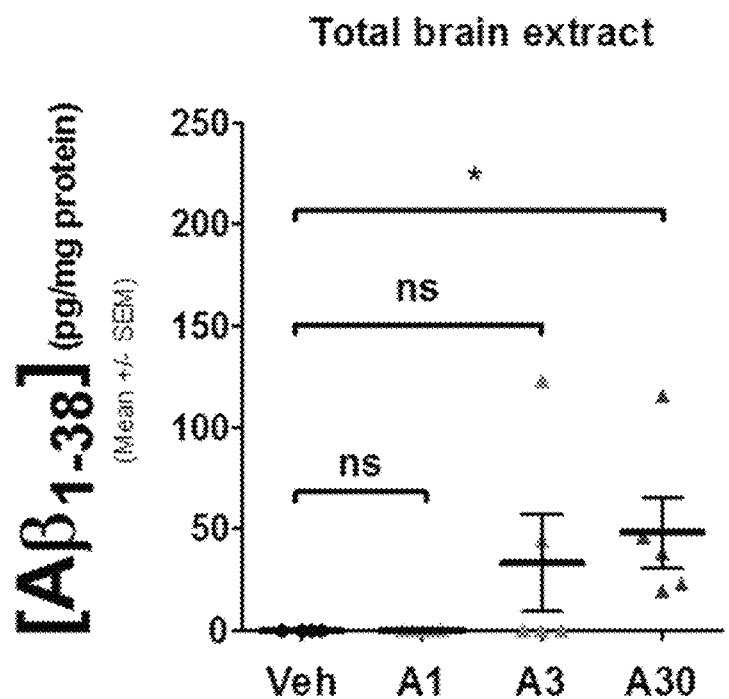
FIG. 6. Plots illustrating the effect of Aftin-5 on $A\beta$ production in total brain extract of C57Bl6J mice. C57Bl/6J mice were exposed sub-cutaneously to Aftin-5 at 1 mg/kg (A1), 3 mg/kg (A3) or 30 mg/kg (A30) or vehicle (DMSO/PEG; Veh) during 28 days through an Alzet osmotic pump (pump 1004, Q=0.14 μl/hrs). 28 days later, brain tissues were collected. $A\beta_{1-38}$ (A), $A\beta_{1-40}$ (B) and $A\beta_{1-42}$ (C) were extracted and quantified by sandwich immunoassay using the Meso Scale Discovery technology. The concentration ratio $A\beta_{1-42}/A\beta_{1-40}$ is depicted in (D). Brain $A\beta$ concentrations were expressed versus total proteins concentration. Kruskal-Wallis test and Dunn's Multiple Comparison post-hoc test were performed and *p<0.05 indicates significant differences between conditions, **p<0.01. Data expressed as means+/−SEM from one experiment with n=4-5 mice/condition.
Figure 6B:
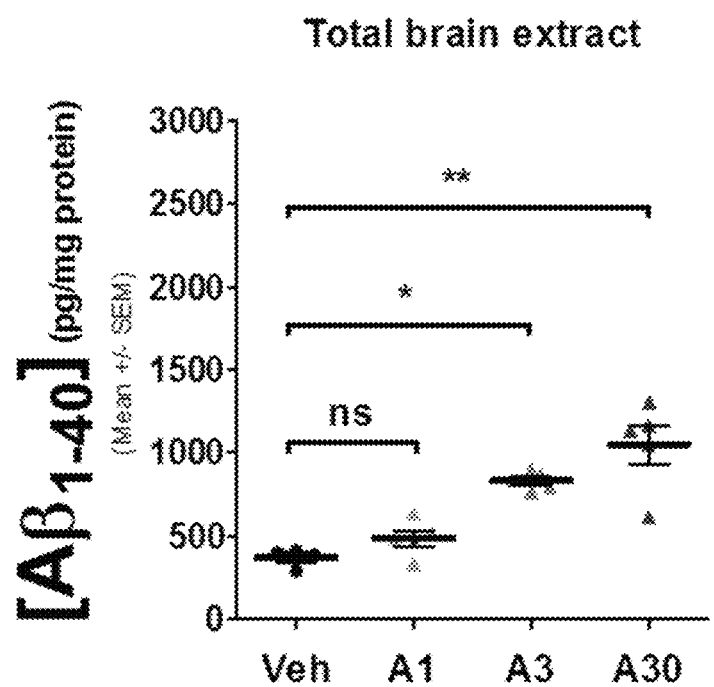
Figure 6C:
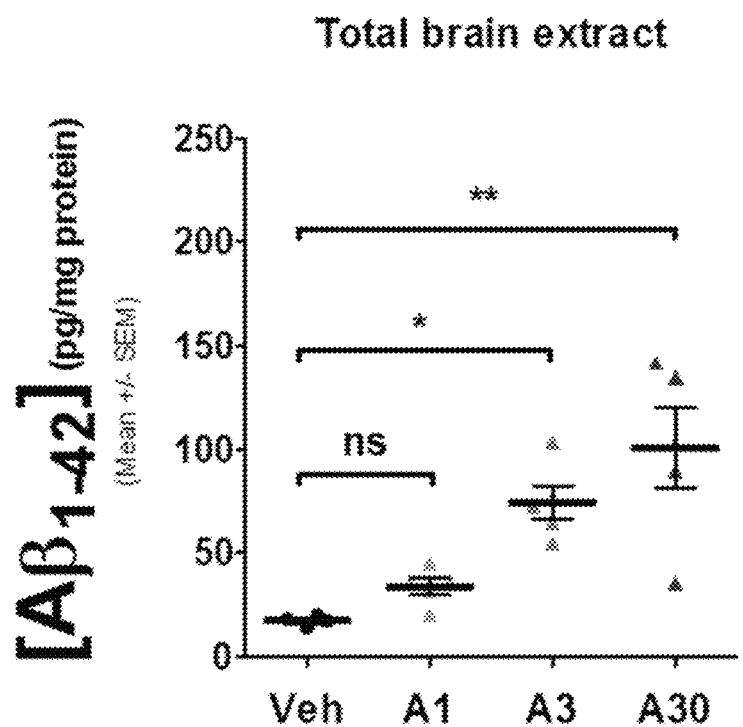
Figure 6D:
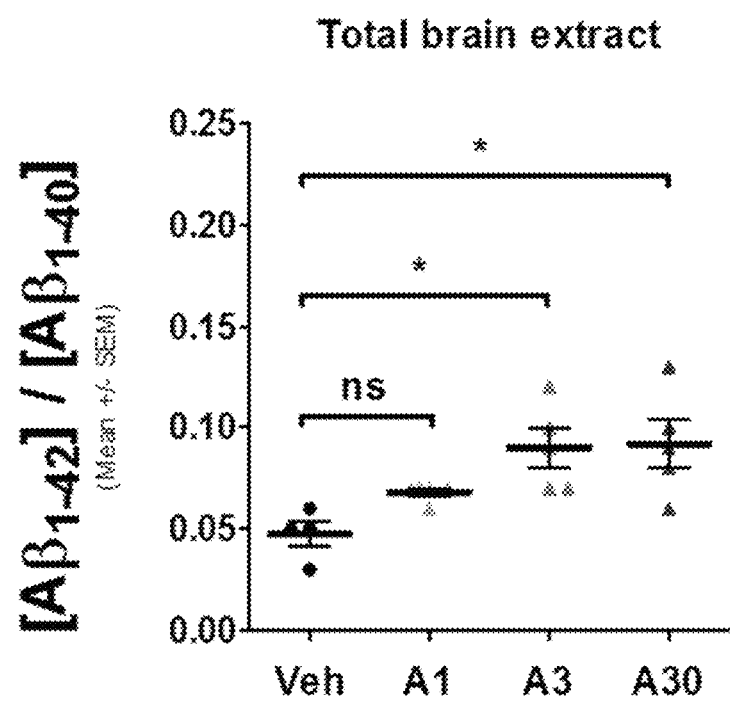

Subcutaneous chronic administration of Aftin-5 to mice increases afin-5 plasma and brain concentrations (FIGS. 5A and 5B). The brain/plasma partition coefficient ($K_{pbrain/plasma}$) was about 0.44, suggesting brain entry of Aftin-5 after subcutaneous chronic administration

Example 4—Effect of Aftin-5 on Aggregates R-Pleated Sheets in Mice

Immunohistochemistry assay was conducted with the total brain tissue, from mice treated with Aftin-5 during 28 days, in the presence of Thioflavin-S dye, which binds aggregates of β-pleated sheets. Observation by microscopy did not revealed binding of the Thioflavin-S dye, indicating the absence of aggregates of β-pleated sheets. Taken together, these findings revealed that Aftin-5 does not recapitulate the amyloid phenotype.

Example 5—Effect of Aftin-5 on Tau Protein Phosphorylation

Figure 7:
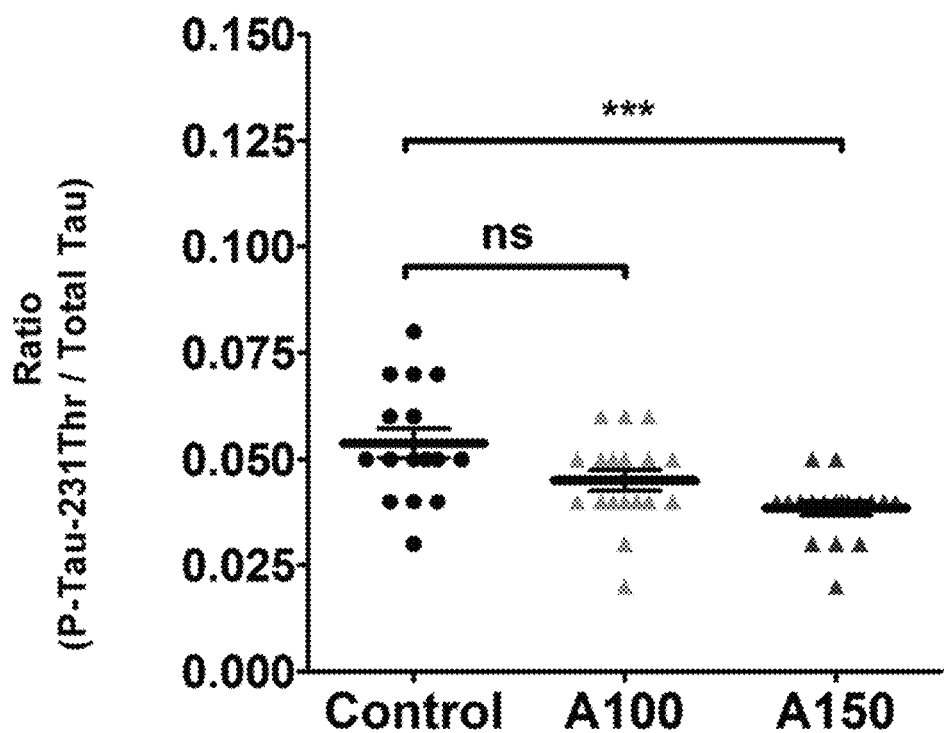
FIG. 7. Plots illustrating the effect of Aftin-5 mediated attenuation of Tau phosphorylation in neuronal primary cultures. Culture media of cortical neurons were replaced by incubation medium containing Aftin-5 at 100 μM (A100) or 150 μM (A150) or vehicle (0.1% DMSO; Control). After 18 h incubation pTau (Thr231) and total Tau were quantified by sandwich immunoassay using the Meso Scale Discovery technology. Different Tau concentrations were expressed versus total proteins concentration. Kruskal-Wallis test and Dunn's Multiple Comparison post-hoc tests were performed and ***p<0.001 indicates significant differences between Aftin-5 and control conditions. Data expressed as means+/−SEM (n=6 wells/condition).

To examine control and treated cell culture for the presence abnormal phosphorylation of Tau protein, one of the hallmarks of the pathogenesis Alzheimer's disease, we investigated the direct impact of Aftin-5 on the production of Thr231 phosphorylated Tau in neurons from WT mice using MSD technology. The results showed that treatment of neurons with Aftin-5 at 50 μM, 100 μM and 150 μM for 18 h resulted in significant dose dependent decrease of Thr231 phosphorylated Tau protein (FIG. 7).

Taken together, Aftin-5 downregulates phosphorylation of Tau protein and does not lead to AD like phenotype.

Example 6—Aftin-5 does not Promote Upregulation of APP

Figure 8:
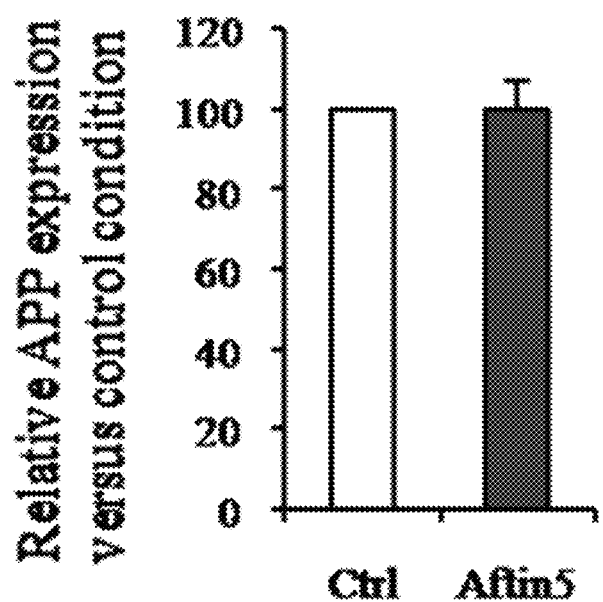
FIG. 8. Plots illustrating the effect of Aftin-5 on APP protein expression in neuronal primary cultures. Culture medium of hippocampal neurons was replaced by incubation medium containing Aftin-5 (100 μM) or vehicle (0.1% DMSO). 18 h later, APP protein in lysate was quantified by Western blotting with anti-APP polyclonal antibody (Millipore). The Western blots were quantified by densitometric analysis. Relative APP protein expression was expressed (Aftin-5) as comparison with the control condition (vehicle; Ctrl). Data expressed as means+/−SEM from one experiment with n=5 wells/condition.

A possible explanation of the action of Aftin-5 onto the observed induction of $A\beta_{1-42}$ may be an upregulation of amyloid precursor protein (APP). In order to assess this hypothesis, immunoblotting experiments were conducted. The data showed that Aftin-5 does not change the level of APP in neurons cells (FIG. 8). Therefore, the induction of $A\beta_{1-42}$ in vitro by Aftin-5 cannot be accounted for an induction of APP.

Example 7—Aftin-5 Attenuates Neuro-Inflammation

Neuro-inflammation may be observed in disorders such as ulcerative colitis, rheumatoid arthritis, Rasmussen disease, and has also been implicated in contributing to AD pathophysiology.

For example, pro-inflammatory cytokines such as IL-β, IL-6 and TNFα have been found to be elevated in plasma and brains of AD patients whereas anti-inflammatory cytokines such as IL10, IFN-γ decreased.

Figure 9:
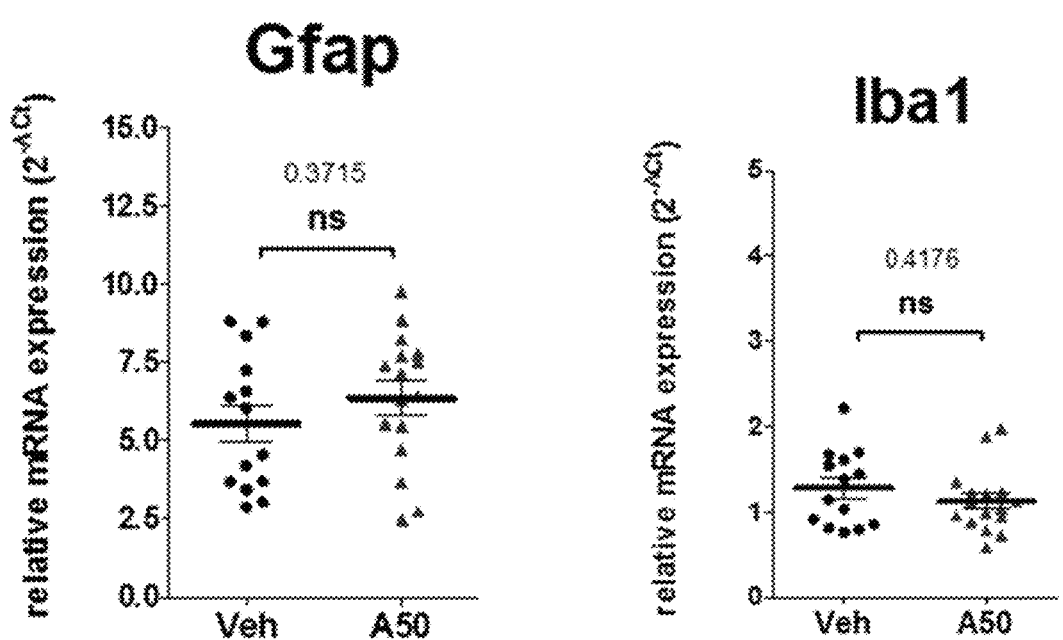
FIG. 9. Plots illustrating the effect of Aftin-5 on relative mRNA expression levels of GFAP (left panel) and Iba-1 (right panel) in organotypic hippocampal slice cultures (OHSC). OHSC culture media of cortical neurons were replaced by incubation medium containing Aftin-5 (50 μM; A50) or vehicle (0.1% DMSO; Veh). 10 days later, total mRNA in lysate was isolated and purified, cDNAs were then synthesized from 0.5 g of total mRNA. cDNA were amplified by quantitative RT-PCR and the relative expression of specific genes was normalized to the housekeeping gene HPRT1 ($2^{-\Delta Ct}$). Mann-Whitney tests were performed and show no significant differences between Aftin-5 and control conditions. Data expressed as means+/−SEM from q=3 independent experiments with n=4-6 inserts/condition and 10 slices/insert.
Figure 10A:
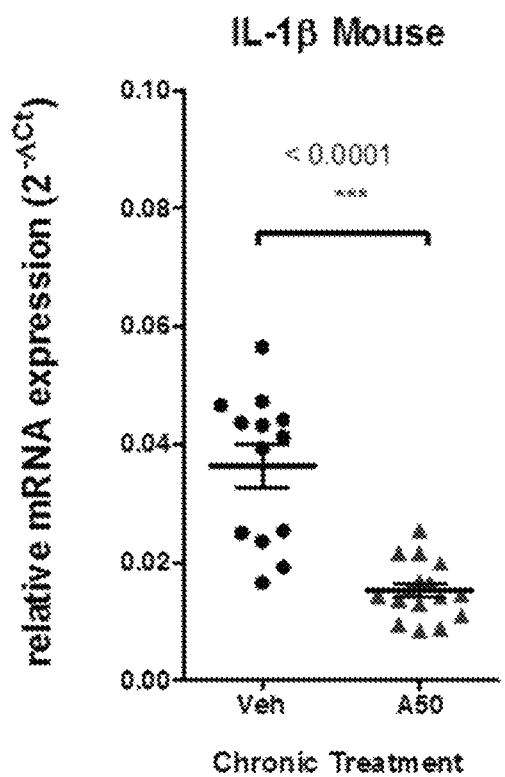
FIG. 10. Plots illustrating the effect of Aftin-5 on relative mRNA expression levels of interleukin-1-beta (IL-1β; (A)), interleukin-6 (IL-6; (B)), TNF-alpha (TNFα; (C)) and interleukin-10 (IL-10; (D)) in organotypic hippocampal slice cultures (OHSC). OHSC culture media of cortical neurons were replaced by incubation medium containing Aftin-5 (50 μM; A50) or vehicle (0.1% DMSO; Veh). 10 days later, total mRNA in lysate was isolated and purified, cDNAs were then synthesized from 0.5 g of total mRNA. cDNAs were amplified by quantitative RT-PCR and the relative expression of specific genes was normalized to the housekeeping gene HPRT1 ($2^{-\Delta Ct}$). Mann-Whitney tests were performed and ***p<0.001 indicates significant differences between Aftin-5 and control conditions. Data expressed as means+/−SEM from q=3 independent experiments with n=4-6 inserts/condition and 10 slices/insert.
Figure 10B:
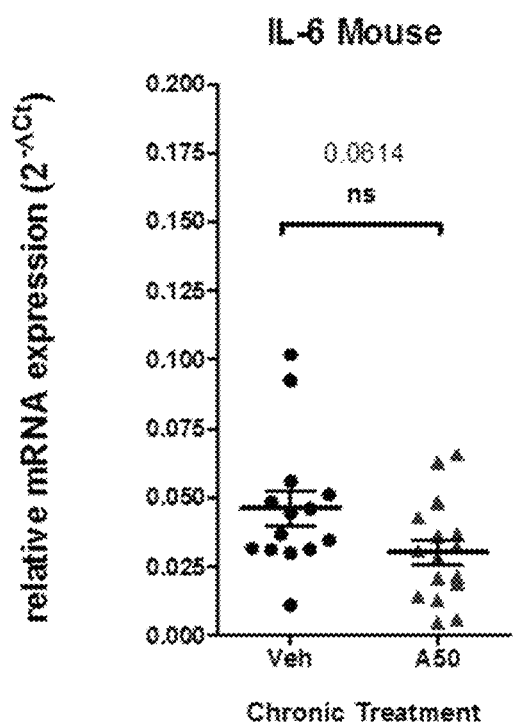

Chronic treatment of organotypic slice cultures with Aftin-5 (50 μM) does not affect microglial/astrocytes phenotype (FIG. 9), but significantly decrease IL-1β-mRNA synthesis (P<0.001) compared to OHSC treated with vehicle (0.1% DMSO) but do not achieve significance for IL-6 (P=0.06) (FIGS. 10A and 10B, respectively).

Figure 10C:
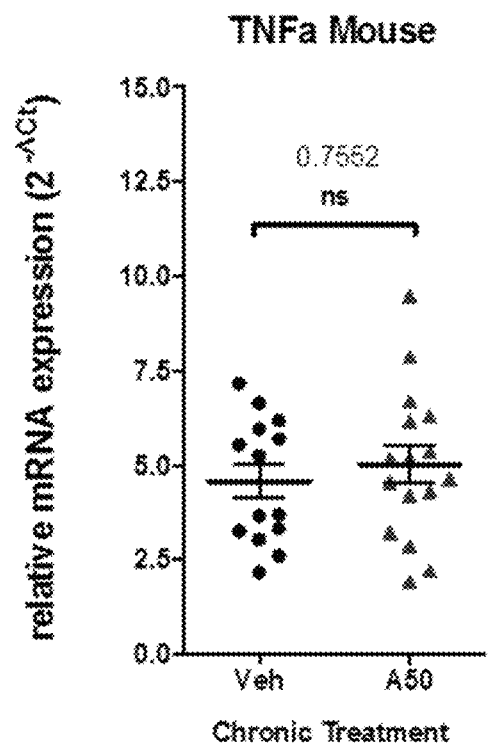
Figure 10D:
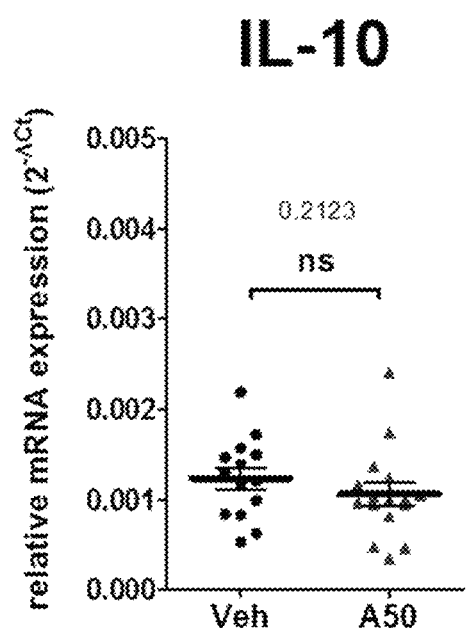

In addition, no changes in TNF-α as well as in IL-10 mRNA synthesis were evidenced (FIGS. 10C and 10D, respectively). The reduction of IL-1β mRNA and the trend of reduction of IL-6 mRNA synthesis may be due to the attenuation of IL-1β signaling in microglia of organotypic hippocampal slice cultures. The ultimate question that arises from these studies relates to the molecular pathway involved in the IL-1β and IL-6 downregulation.

Figure 11A:
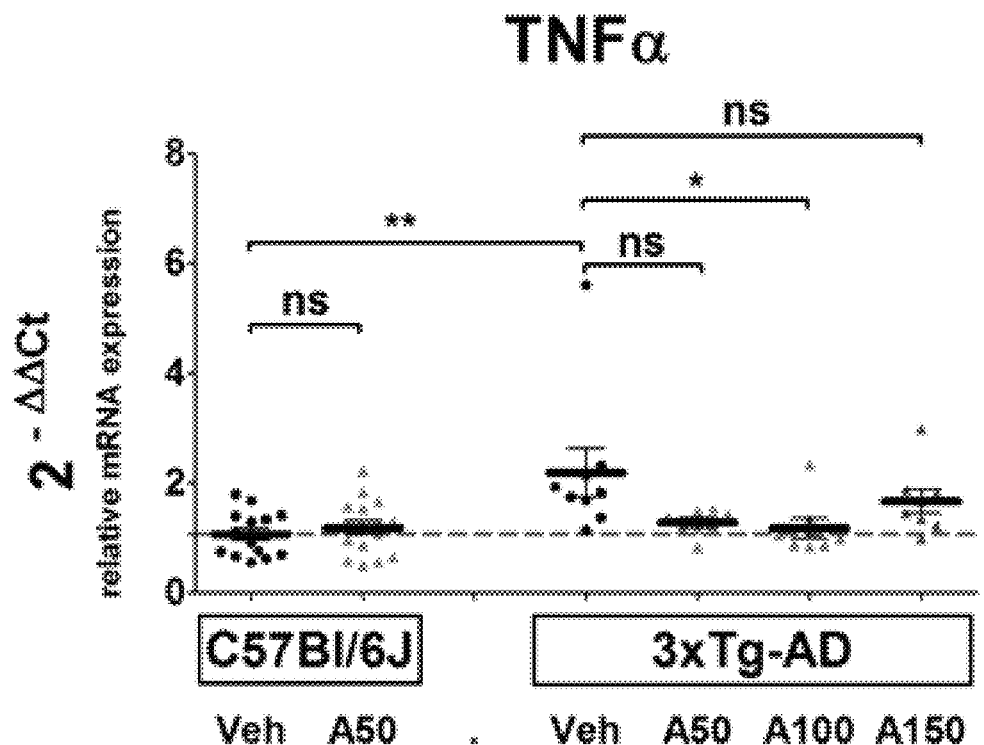
FIG. 11. Plots illustrating the effect of Aftin-5 mediated attenuation of TNF-α (A) and IL-1β (B) and IL-6 (C) in organotypic hippocampal slice cultures from wild type mice (C57Bl/6J) and transgenic Tau mice (3×Tg-AD). 3 Tg organotypic hippocampal slice cultures media were replaced by incubation medium containing Aftin-5 at 50 μM (A50), 100 μM (A100) and 150 μM (A150) or vehicle (0.1% DMSO; Veh). After chronic treatment (10 days) total mRNA in lysate was isolated and purified, cDNAs were then synthesized from 0.5 g of total mRNA. cDNAs were amplified by quantitative RT-PCR and the relative expression of specific genes was normalized to the housekeeping gene HPRT1 ($2^{-\Delta Ct}$). Kruskal-Wallis test and Dunn's Multiple Comparison post-hoc tests were performed and *p<0.05 indicates significant differences between Aftin-5 and control conditions, ***p<0.001. Data expressed as means+/−SEM (n=2-6 wells/condition) from q=2 independent experiments with n=2-6 inserts/conditions and 10 slices/insert.
Figure 11B:
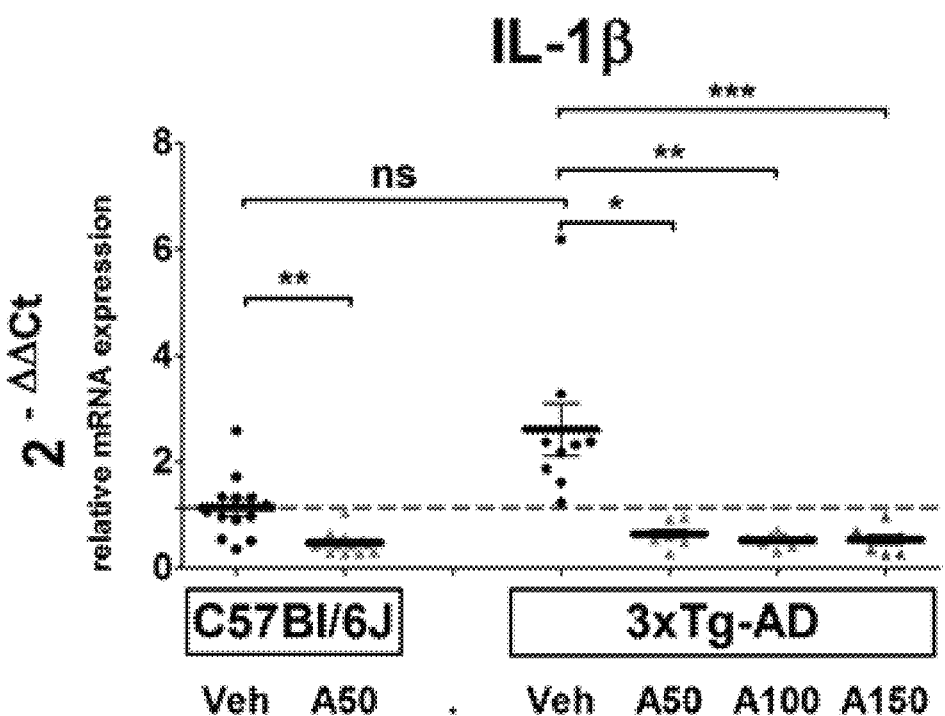
Figure 11C:
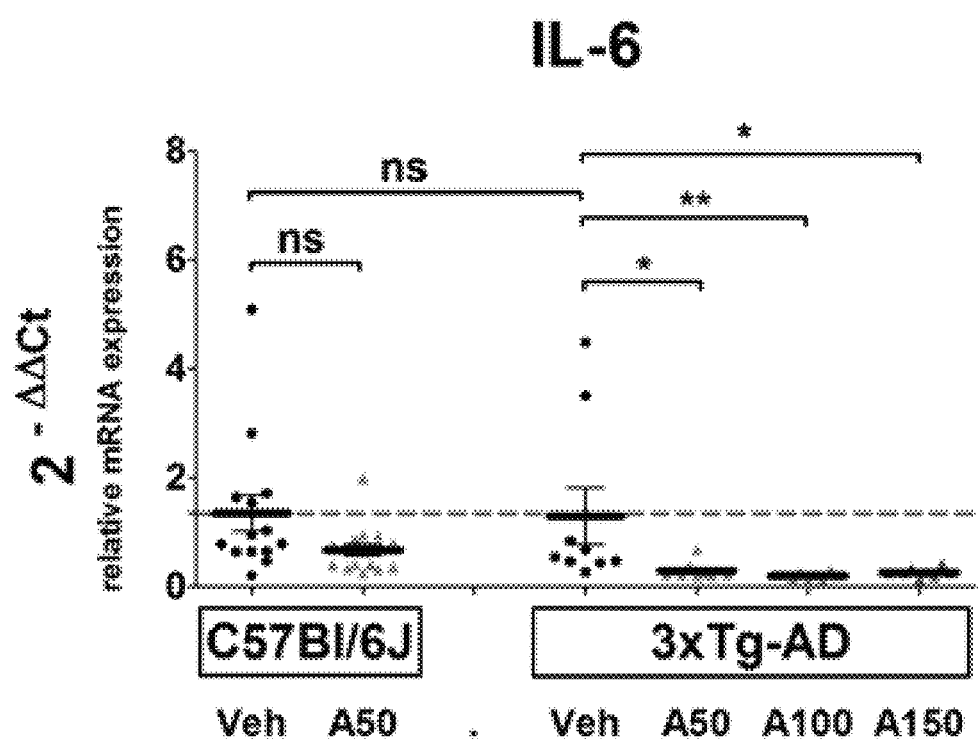

Generally speaking, IL1-β production in microglia activates p38-MAPK cascade in neurons, therefore we assume that Aftin-5 could reduce p38-MAK activation. Very interestingly, organotypic slice cultures from transgenic mice overexpressing P-Tau protein and exhibiting elevated TNF-α, IL-1β and IL-6 mRNA (FIGS. 11A, B and C, respectively), treatment of OHSC with Aftin-5 decreases cytokine-mRNA synthesis compared to OHSC treated with vehicle (0.1% DMSO) (FIG. 11).

Example 8—Aftin-5 Modulates Glucose Metabolism in OHSC and in Brain WT Mice

Figure 12A:
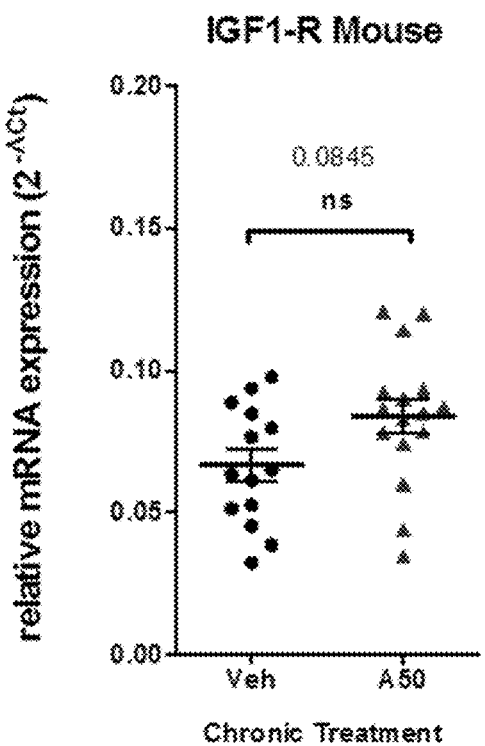
FIG. 12. Plots illustrating the effect of Aftin-5 on relative mRNA expression levels of murine insulin-like growth factor-1 receptor (IGF1-R; (A)) and murine insulin receptor (Insr; (B)) in organotypic hippocampal slice cultures (OHSC). OHSC culture media of OHSC were replaced by incubation medium containing Aftin-5 (50 μM; A50) or vehicle (0.1% DMSO; Veh). 10 days later, total mRNA in lysate was isolated and purified, cDNAs were then synthesized from 0.5 g of total mRNA. cDNAs were amplified by quantitative RT-PCR and the relative expression of specific genes was normalized to the housekeeping gene HPRT1 ($2^{-\Delta Ct}$) Mann-Whitney tests were performed and *p<0.05 indicates significant differences between Aftin-5 and control conditions. Data expressed as means+/−SEM from q=3 independent experiments with n=4-6 inserts/condition and 10 slices/insert.
Figure 12B:
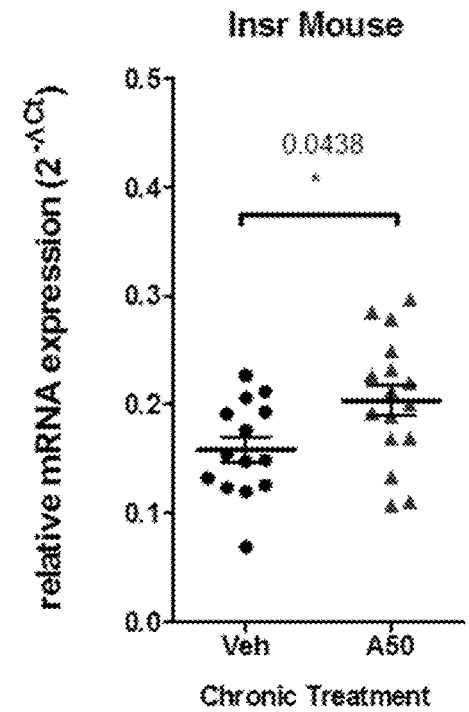

Several pieces of evidence showed that phosphorylation of Tau protein is associated with the decrease of O-GlucNacetylation, a common posttranscriptional modification of nucleocytoplasmic protein with β-Nacetyl glucose. This process depends on glucose metabolism and two tyrosine kinase receptors, InsR (insulin-receptor) and IGF-1R (insulin growth factor receptor 1), which are impaired in AD patients. Since Aftin-5 downregulates the production of Thr231 phosphorylated Tau in neurons from WT mice, we investigated the relationship between glucose metabolism and Tau phosphorylation and Aβ production. Transcriptional profiling for InsR, IGF-1R was performed. The results showed that treatment of OHSC with Aftin-5 at 50 μM for 10 days increased dramatically InsR-mRNA ($P<0.05$) and tend to increase IGF-1R mRNA without achieve significance ($P=0.0845$; FIGS. 12A and 12B).

Example 9—Aftin-5 Improves Long Term Memory

A. Aftin-5 Treatment in WT Mice Improve Long Term Memory

Figure 13A:
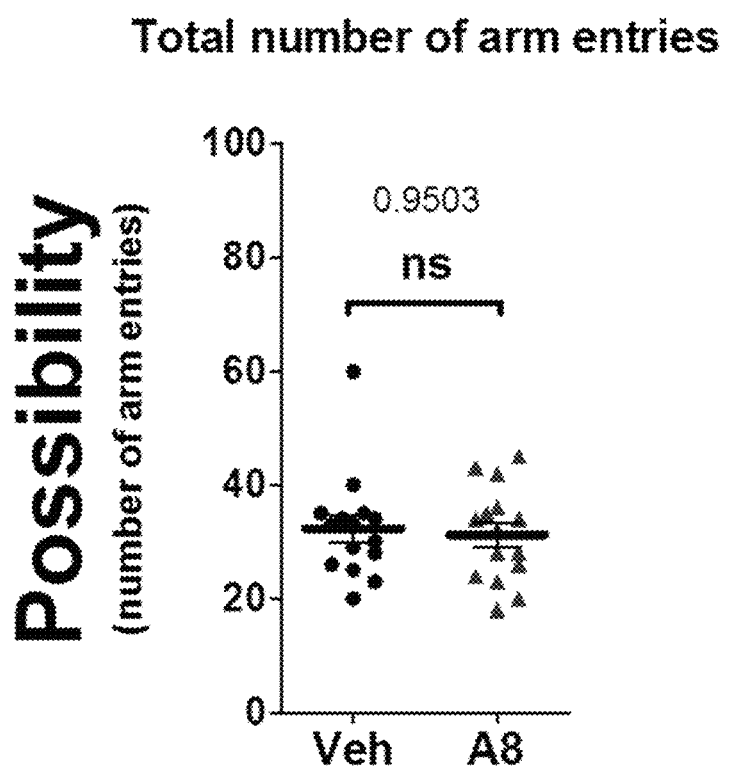
FIG. 13. Plots illustrating the effect of Aftin-5 on short-term memory (working memory) in Y maze. C57Bl/6J mice were exposed sub-cutaneously to Aftin-5 at 8 mg/kg (A8) or vehicle (DMSO/PEG; Veh) during 28 days through an Alzet pump. 3-4 weeks later, cognitive abilities were assessed by the means of the total number of arm entries (A) and the percentage of alternation (B). Mann-Whitney tests were performed and **p<0.01 indicates significant differences between Aftin-5 and control conditions. Data expressed as means+/−SEM with n=15 mice/condition.
Figure 13B:
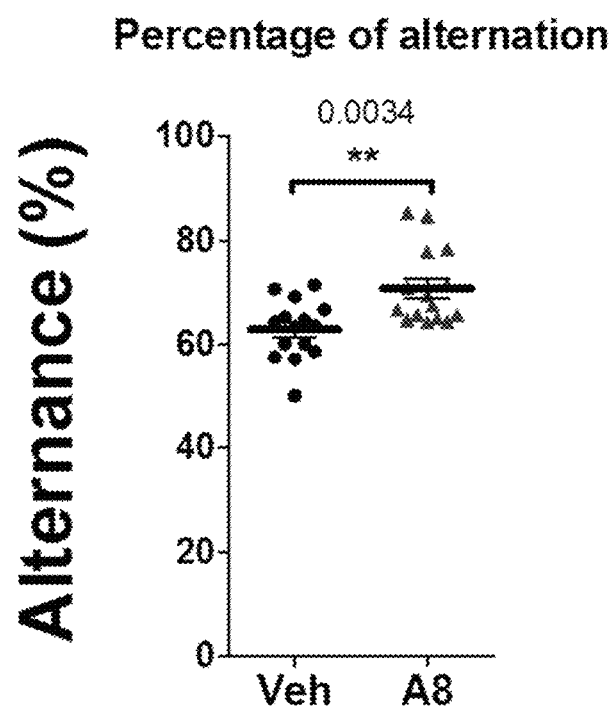
Figure 14A:
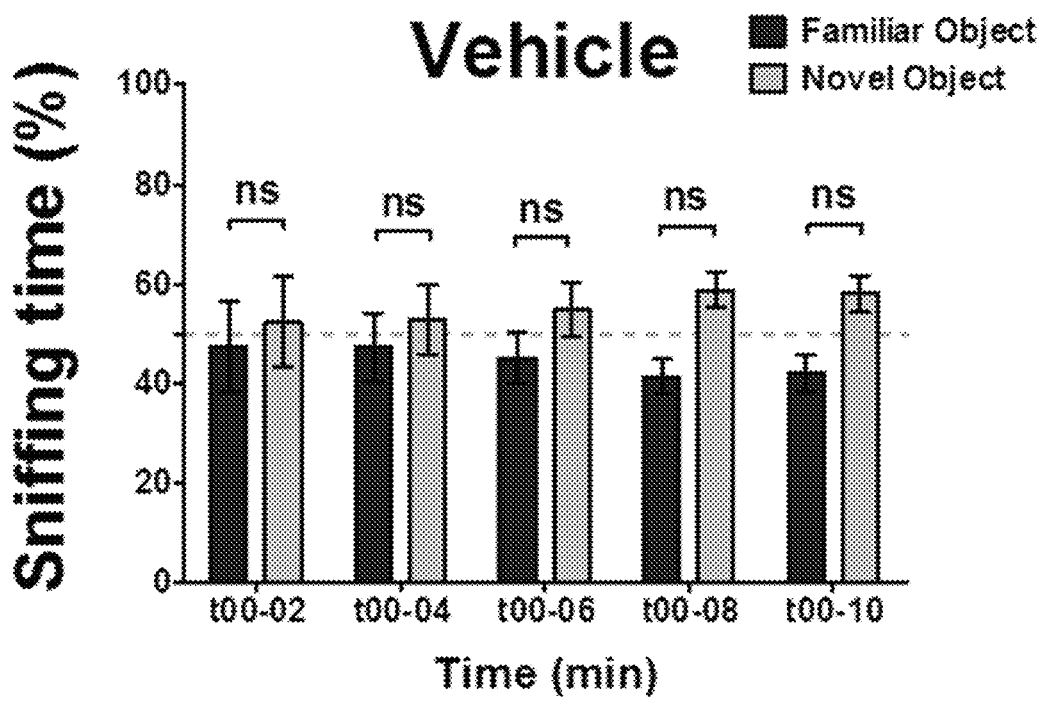
FIG. 14. Plots illustrating the effect of Aftin-5 on non-spatial medium-term memory. C57B1/6J mice were exposed sub-cutaneously to (A) the vehicle condition (DMSO/PEG) or (B) Aftin-5 at 8 mg/kg, during 28 days through an Alzet pump. 3-4 weeks later, cognitive abilities were assessed through different novel object recognition (NOR) tests, including the recognition of familiar objects (dark gray bars) or novel objects (light gray bars). Two-way ANOVA and Bonferroni post-hoc tests were performed and *p<0.05 indicates significant differences between Aftin-5 and control conditions, **p<0.01. Data expressed as means+/−SEM with n=15 mice/condition.
Figure 14B:
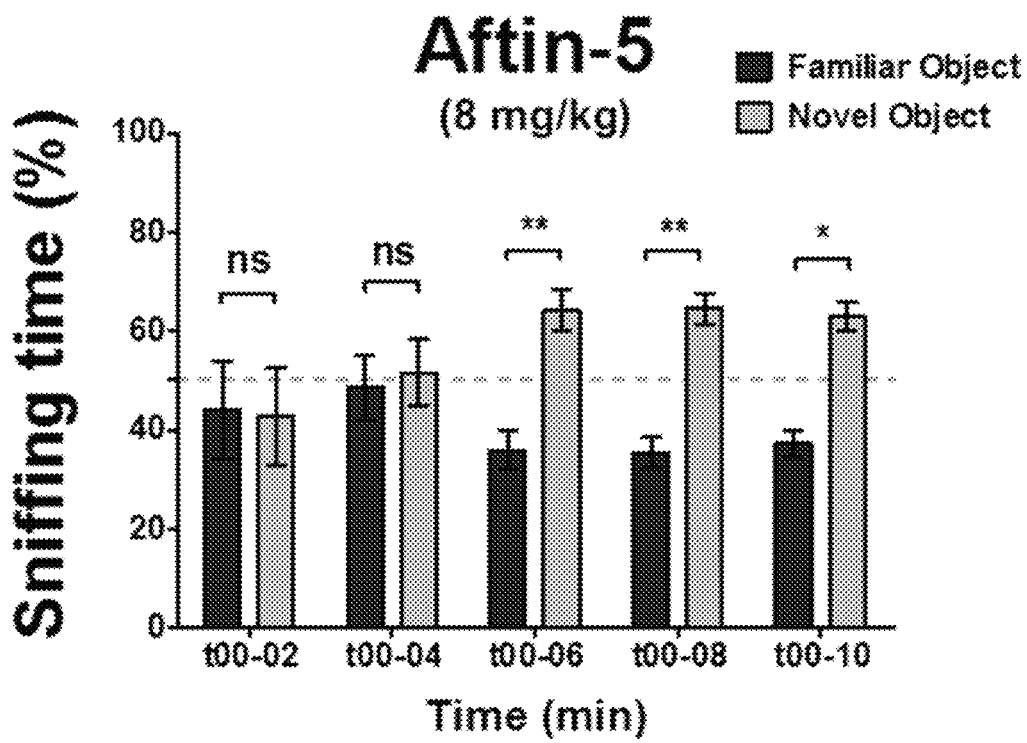

The hypothesis of whether Aftin-5 would improve long term spatial memory in WT mice was assessed. The Y-maze test and novel object recognition test (NOR) were performed in WT mice treated with Aftin-5 at 8 mg/kg or with vehicle (0.1/DMSO/PEG)). Within 28 days of subcutaneous treatment, in the Y-maze treated mice spent more time in the novel arm than animal control suggesting that Aftin-5 improved spatial memory in these animals (FIGS. 13A and 13B). In the NOR test, improvement of long term object recognition memory in the Aftin-5 treated mice does not achieve significance (FIGS. 14A and 14B).

B. Aftin-5 Improves Synaptic Function

Figure 15A:
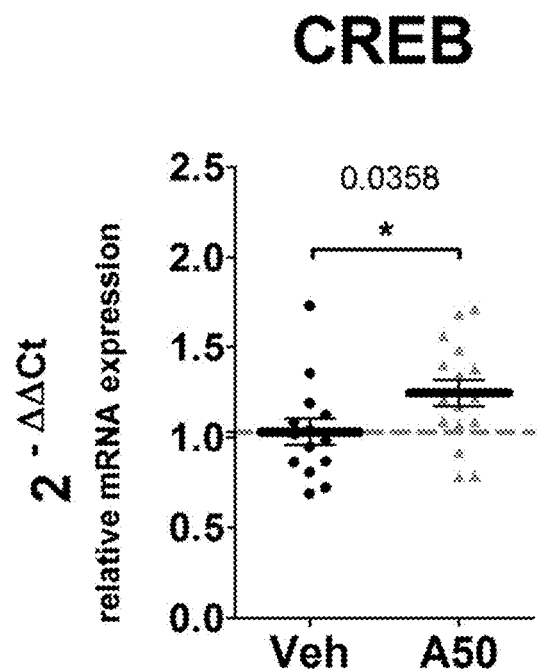
FIG. 15. Plots illustrating the effect of Aftin-5 on relative mRNA expression levels of Long Term Potentialisation (LTP) biomarkers, i.e CREB (A), PSD95 (B) and BDNF (C) in C57B16J OHSC mice treated chronically with Aftin-5. OHSC culture media of OHSC were replaced by incubation medium containing Aftin-5 (50 µM; A50) or vehicle (0.1% DMSO; Veh). 10 days later, total mRNA in lysate was isolated and purified, cDNAs were then synthesized from 0.5 g of total mRNA. cDNAs were amplified by quantitative RT-PCR and the relative expression of specific genes was normalized to the housekeeping gene HPRT1 ($2^{-\Delta Ct}$). Mann-Whitney tests were performed and *p<0.05 indicates significant differences between Aftin-5 and control conditions. Data expressed as means+/−SEM from q=3 independent experiments with n=4-6 inserts/condition and 10 slices/insert.
Figure 15B:
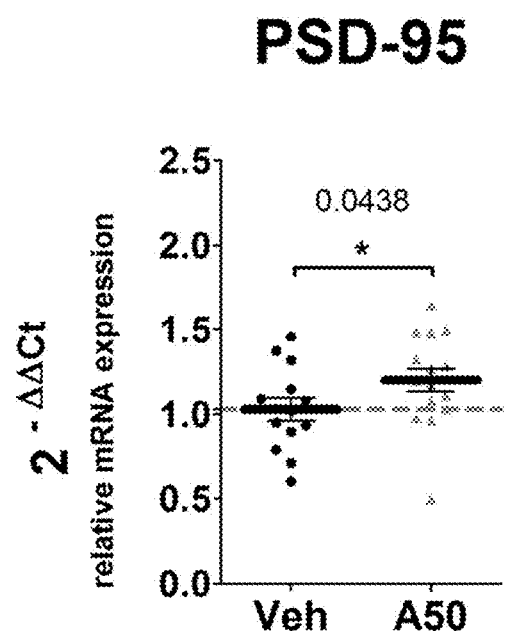
Figure 15C:
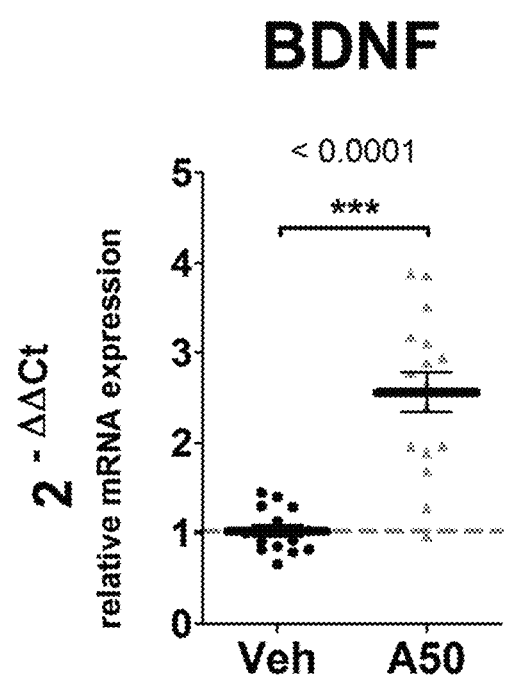

The hypothesis of whether the improvement of long term spatial memory in the brain of WT mice was associated with increased synaptic function was investigated. Transcriptional regulation of CREB, BDNF as well as of PSD95 was investigated. Indeed, abnormalities in the expression profile of immediate early genes that play a critical memory formation such as CREB have been reported in the brains of AD patients. And several pieces of evidences reported previously showed that Aβ accumulation playing a pivotal role in the cognitive deficits of AD patients interfere with CREB activity and thereby its target BDNF. Treatment of OHSCs from WT mice treated with aftin-5 for 10 days revealed transcriptional upregulation of CREB, PSD95 and BDNF (FIGS. 15A, 15B and 15C, respectively).

In addition, brains from WT mice treated chronically with Aftin-5 exhibited high mRNA for CREB, BDNF as well as for PSD95.

Thus, the improvement of cognitive function evidenced in the WT mice treated with Aftin-5 is associated with the increase in BDNF, CREB and PDS95.

Example 10—Attenuation of Protein Tau's Phosphorylation and Cytokines Production Mediated by Purine Derivatives For assessing the protein Tau's phosphorylation, the culture media of rat cortical neurons were replaced by incubation medium containing purine derivatives at 10 μM (A100) or vehicle (0.1% DMSO; Control). After 18 h incubation p-Tau (Thr212) and total Tau were quantified in the cellular extracts by western-blot.

For assessing the cytokine production, human primary glial cells were grown until confluent on coated collagen 12-well plates. Cells were serum-starved in glial serum-free medium for 2 h and treated with LPS for 6 h before treatment with purine derivatives (10 μM) for an additional 18 h. Supernatants were harvested and secreted IL-6 cytokine was measured by ELISA by the mean of the Meso Scale Discovery (MSD) technology. Briefly, a 96-well plate having 1 spot pre-coated with the corresponding antibody is provided by MSD Technology. Before adding the samples, a first saturation step is required. Once the plate is saturated and washed, 25 μL of sample (or calibrators) per well are loaded and incubated for 1 hour. Then the plate is washed and incubated with 25 μL of the Detection Antibody solution (MSD SULFO-TAG) for 1 hour. At the end of the incubation, the plate is washed and then a chemical solution (Read buffer 1x) is added allowing electrochemiluminescence. After a short incubation (5 min) at room temperature, the plate is read on the QUICK Plex SQ120. The instrument measures the intensity of the light electrochemiluminescence.

TABLE 4

Table illustrating the effect of selected purine derivatives Aftin-5 mediated attenuation of Tau phosphorylation in neuronal primary cultures and alleviation of cytokine production in human primary Glia cells.

| No | Structure | Anti-inflammatory Compounds[1] | Attenuation of P-Tau/Tau ratio[1,2] |
|---|---|---|---|
| Aftin-4 | 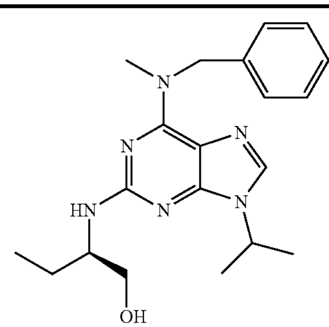 | +(>1 μM) | — |

TABLE 4-continued

Table illustrating the effect of selected purine derivatives Aftin-5 mediated attenuation of Tau phosphorylation in neuronal primary cultures and alleviation of cytokine production in human primary Glia cells.

| No | Structure | Anti-inflammatory Compounds[1] | Attenuation of P-Tau/Tau ratio[1,2] |
|---|---|---|---|
| Aftin-5 | 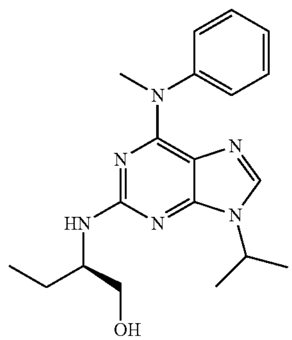 [SMILES: CC[C@H](CO)Nc1nc(N(C)c2ccccc2)c2ncn(C(C)C)c2n1] | +(>1 µM) | +(>1 µM) |
| 13 | 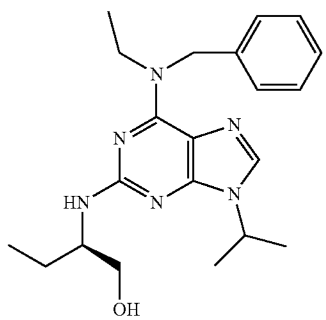 [SMILES: CC[C@H](CO)Nc1nc(N(CC)Cc2ccccc2)c2ncn(C(C)C)c2n1] | +(>1 µM) | +(>1 µM) |
| 14 | 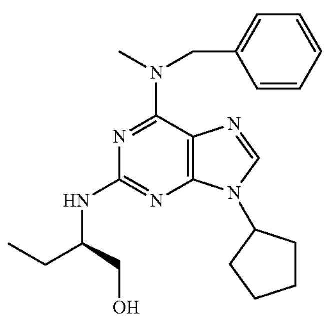 [SMILES: CC[C@H](CO)Nc1nc(N(C)Cc2ccccc2)c2ncn(C3CCCC3)c2n1] | +(>1 µM) | +(>1 µM) |
| 15 | 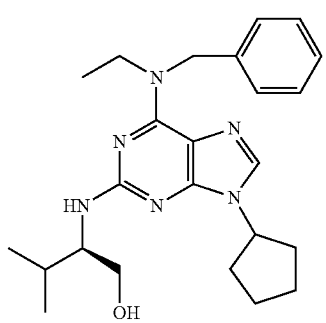 [SMILES: CCN(Cc1ccccc1)c1nc(N[C@@H](CO)C(C)C)nc2c1ncn2C1CCCC1] | +(>1 µM) | +(>1 µM) |

TABLE 4-continued

Table illustrating the effect of selected purine derivatives Aftin-5 mediated attenuation of Tau phosphorylation in neuronal primary cultures and alleviation of cytokine production in human primary Glia cells.

| No | Structure | Anti-inflammatory Compounds[1] | Attenuation of P-Tau/Tau ratio[1,2] |
|---|---|---|---|
| 20 | 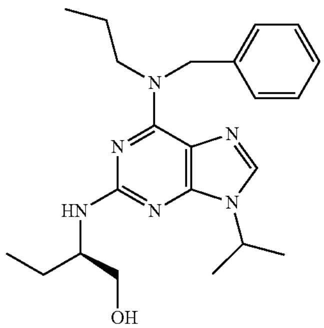 [SMILES: CCCN(Cc1ccccc1)c1nc(N[C@H](CC)CO)nc2c1ncn2C(C)C] | +(>1 μM) | +(>1 μM) |
| 22 | 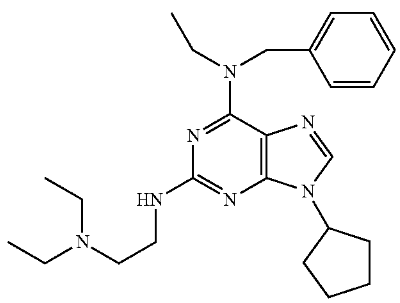 [SMILES: CCN(CC)CCNc1nc(N(CC)Cc2ccccc2)c2ncn(C3CCCC3)c2n1] | +(>1 μM) | +(>1 μM) |
| 23 | 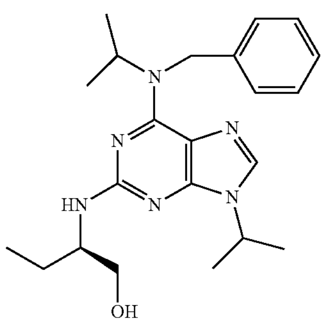 [SMILES: CC[C@H](CO)Nc1nc(N(Cc2ccccc2)C(C)C)c2ncn(C(C)C)c2n1] | +(>1 μM) | — |
| 26 | 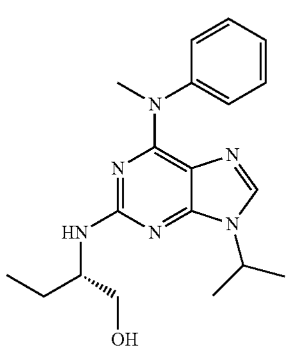 [SMILES: CC[C@@H](CO)Nc1nc(N(C)c2ccccc2)c2ncn(C(C)C)c2n1] | +(>1 μM) | — |

TABLE 4-continued

Table illustrating the effect of selected purine derivatives Aftin-5 mediated attenuation of Tau phosphorylation in neuronal primary cultures and alleviation of cytokine production in human primary Glia cells.

| No | Structure | Anti-inflammatory Compounds[1] | Attenuation of P-Tau/Tau ratio[1,2] |
|---|---|---|---|
| 31 | 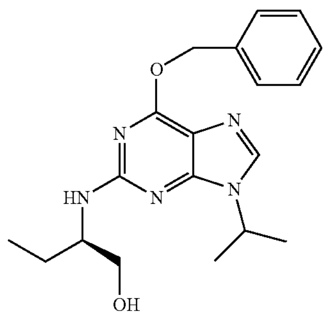 [SMILES: CC[C@H](CO)Nc1nc(OCc2ccccc2)c2ncn(C(C)C)c2n1] | +(>1 μM) | +(>1 μM) |
| Roscovitine | 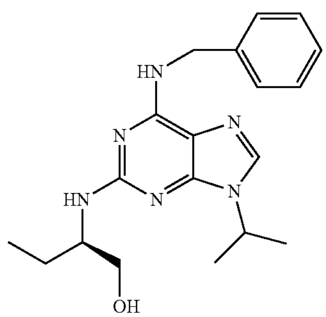 [SMILES: CC[C@H](CO)Nc1nc(NCc2ccccc2)c2ncn(C(C)C)c2n1] | +(>1 μM) | — |

[1] "+" means that the tested compound shows an anti-inflammatory and/or attenuation of Tau's phosphorylation property with a concentration higher than 1 μM and, whereas "–" means no detectable of anti-inflammatory and/or attenuation of Tau's phosphorylation properties.
[2] P-tau relates to the phosphorylated form of the Tau protein; the ratio relates to the content of P-Tau over total content of the Tau protein (both phosphorylated and non-phosphorylated forms).

The invention claimed is:

1. A compound of formula (Ib) as defined below

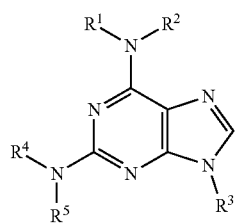

(Ib)

wherein
- $R^1$ is an aryl group, a heteroaryl group, a —$CH_2$-aryl group or a —$CH_2$-heteroaryl group, said aryl and heteroaryl being optionally substituted with one or more substituents independently chosen from a halogen atom, a $CF_3$ group, a hydroxyl group, an $OR^6$ group, a $SR^6$ group, a $NR^6R^7$ group, a CN group, a $CONR^6R^7$ group, a $SOR^6$ group, a $SO_2R^6$ group, an azido group (—N), an aryl group, a heteroaryl group and a ($C_1$-$C_6$) alkyl group,
- $R^2$ is a ($C_1$-$C_6$)alkyl group or a ($C_3$-$C_6$)cycloalkyl group said alkyl and cycloalkyl being optionally substituted with one or more substituents independently chosen from a halogen atom, a hydroxyl group and a $NH_2$ group,
- or $R^1$ forms together with $R^2$ and with the nitrogen atom that bears $R^1$ and $R^2$ an heterobicyclic ring,
- $R^6$ and $R^7$ represent independently of each other a hydrogen atom or a ($C_1$-$C_6$)alkyl group,
- $R^3$ is a ($C_1$-$C_6$)alkyl group, a ($C_3$-$C_6$)cycloalkyl group, an aryl group, a —$CH_2$-aryl group or a —$CH_2$-heteroaryl group, said alkyl, cycloalkyl, aryl and heteroaryl group being optionally substituted with one or more substituents chosen from a halogen atom, a hydroxyl group and a $NH_2$ group, wherein the heterobicyclic ring is selected from

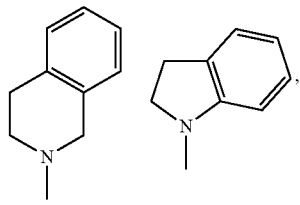

and wherein $NR^4R^5$ is one of the radicals (5'), (6'), (8')-(15'), (17') and (19') as defined herein after:

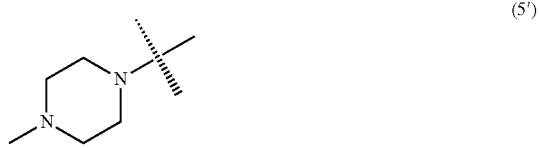

(5')

-continued
(6')
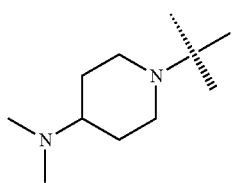
(8')
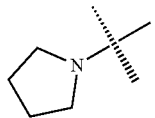
(9')
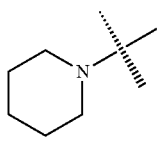
(10')
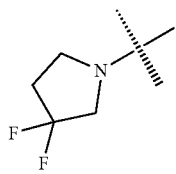
(11')
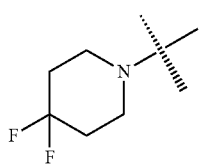
(12')
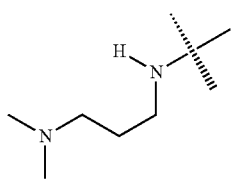
(13')
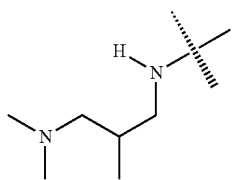
(14')
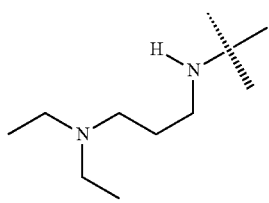
(15')
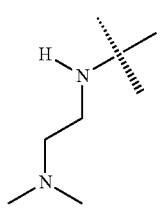
-continued
(17')
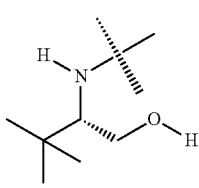
(19')
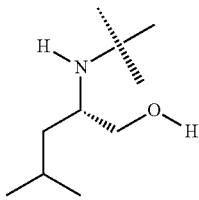
or a pharmaceutically acceptable salt thereof.
2. The compound of formula (Ib)
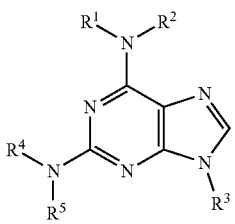
(Ib) as defined in claim 1, or a pharmaceutically acceptable salt thereof, wherein $NR^1R^2$ is one of the radicals (35) to (42), (51) or (67) to (89) as defined herein after:
(35)
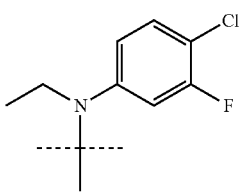
(36)
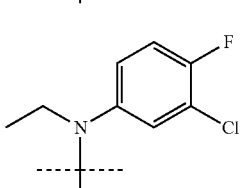
(37)
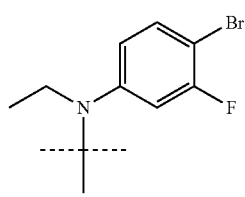

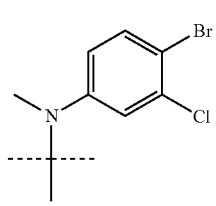
(38)
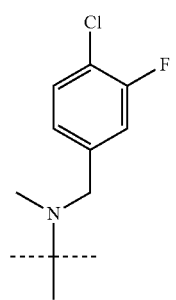
(39)
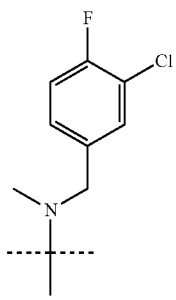
(40)
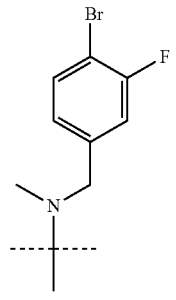
(41)
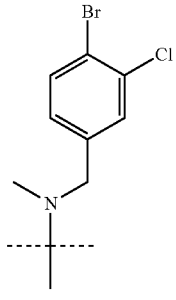
(42)
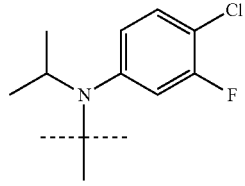
(51)
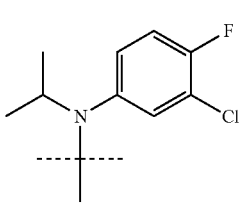
(67)
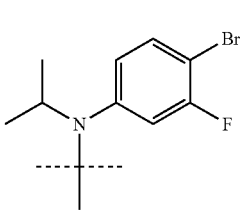
(68)
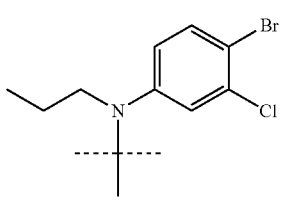
(69)
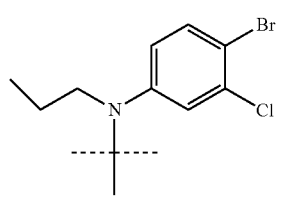
(70)
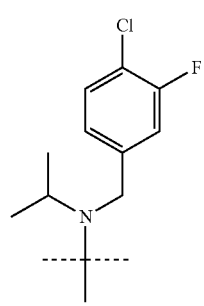
(71)
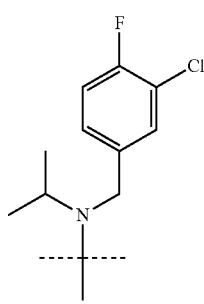
(72)

79
-continued
(73)
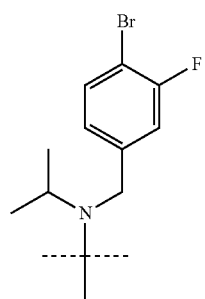
(74)
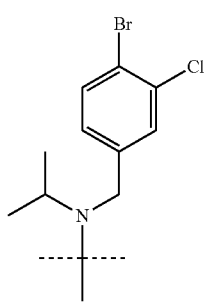
(75)
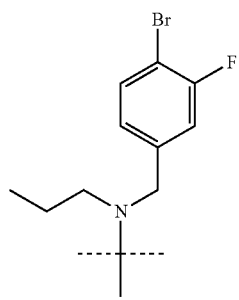
(76)
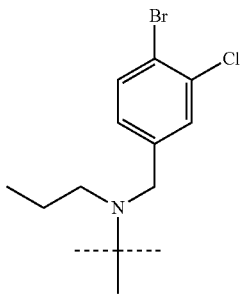
(77)
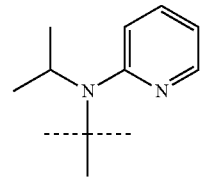
(78)
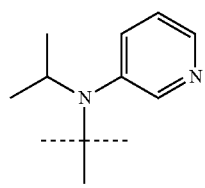
80
-continued
(79)
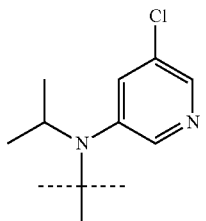
(80)
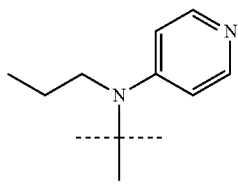
(81)
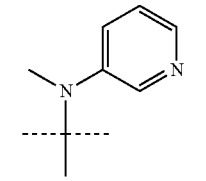
(82)
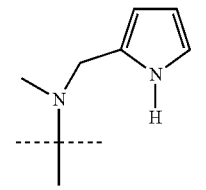
(83)
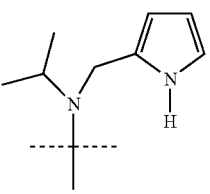
(84)
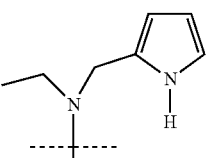
(85)
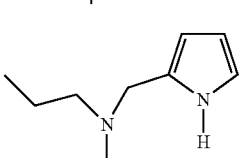
(86)

(87)

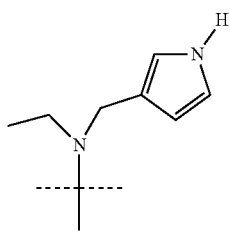

(88)

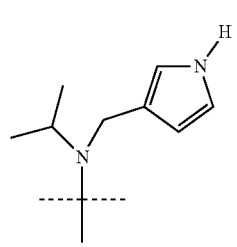

(89)

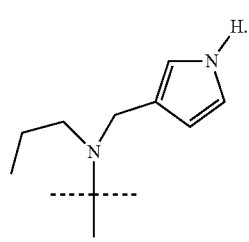

3. The compound of formula (Ib)

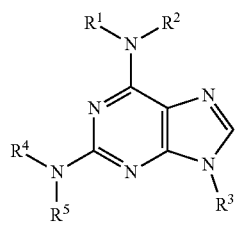

(Ib) as defined in claim 1, or a pharmaceutically acceptable salt thereof, wherein $R^3$ is one of the radicals (2″) to (4″), (9″) and (11″) to (14″) as defined herein after:

(2″)

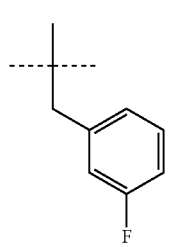

(3″)

(4″)

(9″)

(11″)

(12″)

(13″)

(14″)

4. The compound of formula (Ib)

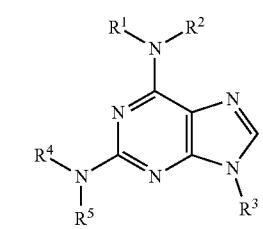

(Ib) as defined in claim 1, or a pharmaceutically acceptable salt thereof, wherein $R^1$ is an aryl group, a heteroaryl group, a —$CH_2$-aryl group or a —$CH_2$-heteroaryl group, said aryl and heteroaryl being substituted with at least one $CF_3$ group.

5. The compound of formula (Ib)

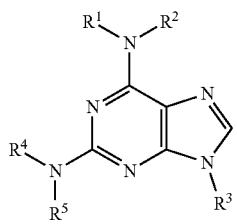
(Ib)

wherein

R¹ is an aryl group, a heteroaryl group, a —CH₂-aryl group or a —CH₂-heteroaryl group, said aryl and heteroaryl being optionally substituted with one or more substituents independently chosen from a halogen atom, a CF₃ group, a hydroxyl group, an OR⁶ group, a SR⁶ group, a NR⁶R⁷ group, a CN group, a CONR⁶R⁷ group, a SOR⁶ group, a SO₂R⁶ group, an azido group (—N₃), an aryl group, a heteroaryl group and a (C₁-C₆)alkyl group, R² is a (C₁-C₆)alkyl group or a (C₃-C₆)cycloalkyl group said alkyl and cycloalkyl being optionally substituted with one or more substituents independently chosen from a halogen atom, a hydroxyl group and a NH₂ group, or R¹ forms together with R² and with the nitrogen atom that bears R¹ and R² an heterobicyclic ring, R⁶ and R⁷ represent independently of each other a hydrogen atom or a (C₁-C₆)alkyl group, R³ is (5″)

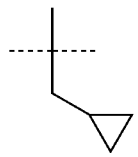

(6″)

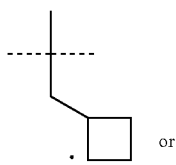   or (7″)

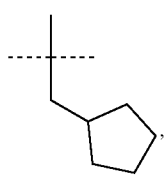, wherein the heterobicyclic ring is selected from

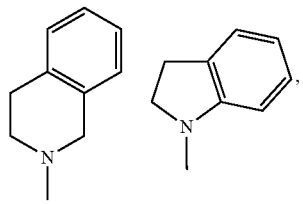

and wherein NR⁴R⁵ is one of the radicals (5'), (6'), (8')-(15'), (17') and (19') as defined herein after:

(5')

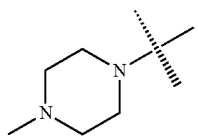

(6')

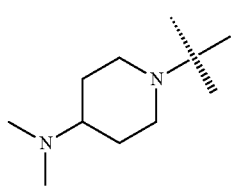

(8')

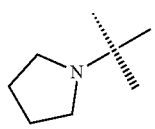

(9')

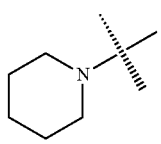

(10')

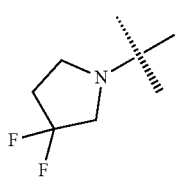

(11')

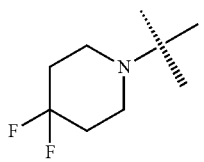

(12')

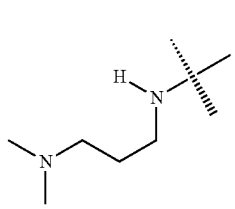

-continued

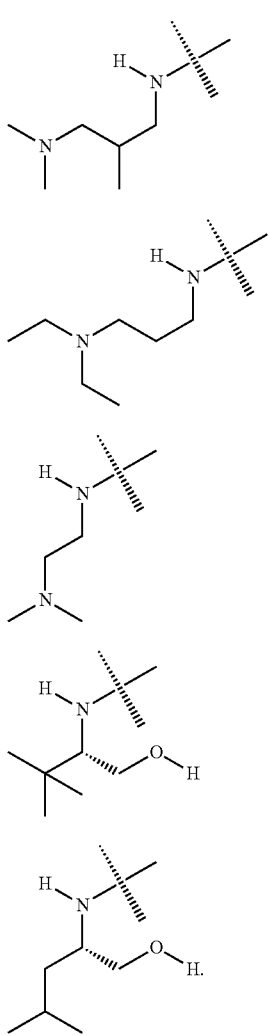

(13')

(14')

(15')

(17')

(19')

6. A pharmaceutical composition comprising the compound of formula (Ib), or a pharmaceutically acceptable salt thereof, and a pharmaceutically acceptable vehicle, wherein the pharmaceutically acceptable vehicle comprises an auxiliary substance or excipient, the auxiliary substance or excipient being one or more member selected from the group consisting of a wetting agent, an emulsifying agent, a preservative and buffer, and the compound of formula (Ib) is represented herein after

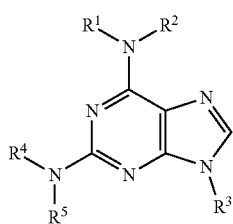

(Ib)

in which $R^1$ is an aryl group, a heteroaryl group, a —$CH_2$-aryl group or a —$CH_2$-heteroaryl group, said aryl and heteroaryl being optionally substituted with one or more substituents independently chosen from a halogen atom, a $CF_3$ group, an $OR^6$ group, a $SR^6$ group, a $NR^6R^7$ group, a CN group, a $CONR^6R^7$ group, a $SOR^6$ group, a $SO_2R^6$ group, an azido group (—$N_3$), an aryl group, a heteroaryl group and a ($C_1$-$C_6$)alkyl group, $R^2$ is a ($C_1$-$C_6$)alkyl group or a ($C_3$-$C_6$)cycloalkyl group said alkyl and cycloalkyl being optionally substituted with one or more substituents independently chosen from a halogen atom, a hydroxyl group and a $NH_2$ group, or $R^1$ forms together with $R^2$ and with the nitrogen atom that bears $R^1$ and $R^2$ an heterobicyclic ring, $R^6$ and $R^7$ represent independently of each other a hydrogen atom or a ($C_1$-$C_6$)alkyl group, $R^3$ is a ($C_1$-$C_6$)alkyl group, a ($C_3$-$C_6$)cycloalkyl group, an aryl group, a —$CH_2$-aryl group or a —$CH_2$-heteroaryl group, said alkyl, cycloalkyl, aryl and heteroaryl group being optionally substituted with one or more substituents chosen from a halogen atom, a hydroxyl group and a $NH_2$ group, $R^4$ is a hydrogen atom, a ($C_1$-$C_6$)alkyl group or a ($C_3$-$C_6$)cycloalkyl group, said alkyl and cycloalkyl being optionally substituted with one or more substituents chosen from a halogen atom, a hydroxyl group and a $NH_2$ group, $R^5$ is a hydrogen atom, a ($C_1$-$C_8$)alkyl group or a ($C_3$-$C_6$)cycloalkyl group, said alkyl and cycloalkyl being optionally substituted with one or more substituents independently chosen from a halogen atom, a hydroxyl group, an azido group and a $NR^6R^7$ group, one or more of the carbon atoms of said alkyl or cycloalkyl being optionally replaced by a nitrogen atom, or alternatively $R_4$ and $R_5$ may form with the nitrogen atom bearing them a ($C_3$-$C_6$)heterocylcoalkyl group, said ($C_3$-$C_6$)heterocylcoalkyl group being optionally substituted by one or more substituents independently chosen from a ($C_1$-$C_4$)alkyl group, a $NR^6R^7$ group and a halogen atom, wherein the heterobicyclic ring is selected from

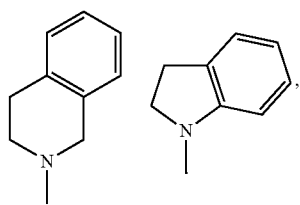

or a pharmaceutically acceptable salt thereof.

7. A method for treating a neurodegenerative disorder selected from Alzheimer's disease, Parkinson's disease, Huntington's disease, amyotrophic lateral sclerosis, and Down's syndrome and/or a neuro-inflammatory disorder being a central nervous system inflammatory disorder selected from Rasmussen inflammatory disorder, rheumatoid arthritis, multiple sclerosis, optic neuritis, osteoarthritis, atherosclerosis and ankylosing spondylitis and/or a viral induced neuro-inflammation, in an individual in need thereof, the method comprising administering to the individual an effective amount of a compound of formula (Ib)

in which

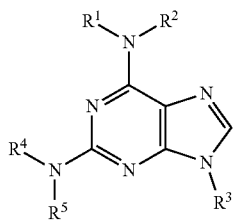
(Ib)

R¹ is an aryl group, a heteroaryl group, a —CH₂-aryl group or a —CH₂-heteroaryl group, said aryl and heteroaryl being optionally substituted with one or more substituents independently chosen from a halogen atom, a CF₃ group, a hydroxyl group, an OR⁶ group, a SR⁶ group, a NR⁶R⁷ group, a CN group, a CONR⁶R⁷ group, a SOR⁶ group, a SO₂R⁶ group, an azido group (—N), an aryl group, a heteroaryl group and a (C₁-C₆) alkyl group, R² is a (C₁-C₆)alkyl group or a (C₃-C₆)cycloalkyl group said alkyl and cycloalkyl being optionally substituted with one or more substituents independently chosen from a halogen atom, a hydroxyl group and a NH₂ group, or R¹ forms together with R² and with the nitrogen atom that bears R¹ and R² an heterobicyclic ring, R⁶ and R⁷ represent independently of each other a hydrogen atom or a (C₁-C₆)alkyl group, R³ is a (C₁-C₆)alkyl group, a (C₃-C₆)cycloalkyl group, an aryl group, a —CH₂-aryl group or a —CH₂-heteroaryl group, said alkyl, cycloalkyl, aryl and heteroaryl group being optionally substituted with one or more substituents chosen from a halogen atom, a hydroxyl group and a NH₂ group, R⁴ is a hydrogen atom, a (C₁-C₆)alkyl group or a (C₃-C₆)cycloalkyl group, said alkyl and cycloalkyl being optionally substituted with one or more substituents chosen from a halogen atom, a hydroxyl group and a NH₂ group, R⁵ is a hydrogen atom, a (C₁-C₈)alkyl group or a (C₃-C₆)cycloalkyl group, said alkyl and cycloalkyl being optionally substituted with one or more substituents independently chosen from a halogen atom, a hydroxyl group, an azido group and a NR⁶R⁷ group, one or more of the carbon atoms of said alkyl or cycloalkyl being optionally replaced by a nitrogen atom, or alternatively R₄ and R₅ may form with the nitrogen atom bearing them a (C₃-C₆)heterocylcoalkyl group, said (C₃-C₆)heterocylcoalkyl group being optionally substituted by one or more substituents independently chosen from a (C₁-C₄)alkyl group, a NR⁶R⁷ group and a halogen atom, wherein the heterobicyclic ring is selected from

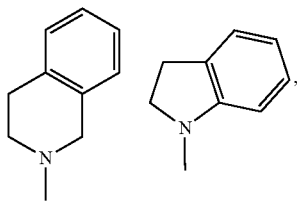

or a pharmaceutically acceptable salt thereof.

8. The method according to claim 7, wherein, in the compound of formula (Ib) or a pharmaceutically acceptable salt thereof, R¹ is an aryl group, a heteroaryl group, a —CH₂-aryl group or a —CH₂-heteroaryl group, said aryl and heteroaryl being optionally substituted with one or more substituents independently chosen from a halogen atom, a CF₃ group, a hydroxyl group, an OR⁶ group, a SR⁶ group, a NR⁶R⁷ group, a CN group, a CONR⁶R⁷ group, a SOR⁶ group, a SO₂R⁶ group, an azido group (—N₃), an aryl group, a heteroaryl group and a (C₁-C₆)alkyl group, a heteroaryl group, a —CH₂-aryl group or a —CH₂-heteroaryl group, said aryl and heteroaryl being optionally substituted with one halogen atom or a CF₃ group, R⁶ and R⁷ represent independently of each other a hydrogen atom or a (C₁-C₆)alkyl group, and R² is a (C₁-C₆)alkyl group or a (C₃-C₆)cycloalkyl group said alkyl and cycloalkyl being optionally substituted with one or more substituents independently chosen from a halogen atom, a hydroxyl group and a NH₂ group.

9. The method according to claim 7, wherein, in the compound of formula (Ib) or a pharmaceutically acceptable salt thereof, NR¹R² radical is chosen from the following radicals:

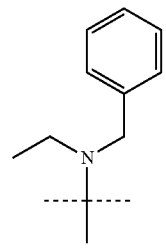
(1)

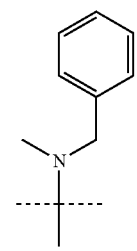
(2)

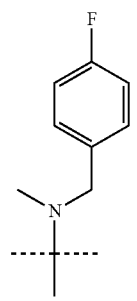
(15)

(17)

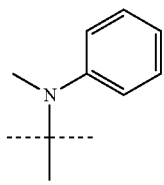

(25)

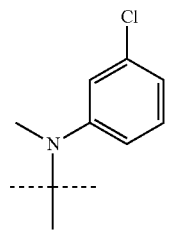

(43)

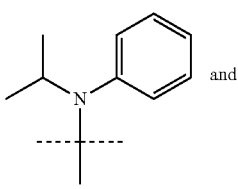 and (44)

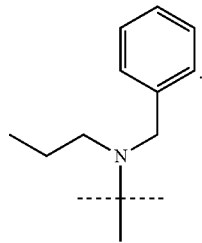

10. The method according to claim 7, wherein, in the compound of formula (Ib) or a pharmaceutically acceptable salt thereof, $R^4$ is a hydrogen atom, $R^5$ is a $(C_1-C_8)$ alkyl group, said alkyl being optionally substituted with one or more substituents independently chosen from a halogen atom, a hydroxyl group and a $NR^6R^7$ group, one or more of the carbon atoms of said alkyl being optionally replaced by a nitrogen atom, said alkyl being optionally substituted with one hydroxyl group, and one of the carbon atoms of said alkyl being optionally replaced by a nitrogen atom, or alternatively $R^4$ and $R^5$ may form with the nitrogen atom bearing them a $(C_3-C_6)$heterocylcoalkyl group, said $(C_3-C_6)$heterocylcoalkyl group being optionally substituted by one or more substituents independently chosen from a $(C_1-C_4)$alkyl group, a $NR^6R^7$ group and a halogen atom, and $R^6$ and $R^7$ represent independently of each other a hydrogen atom or a $(C_1-C_6)$alkyl group.

11. The method according to claim 7, wherein, in the compound of formula (Ib) or a pharmaceutically acceptable salt thereof, the $NR^4R^5$ group is selected from the following radicals

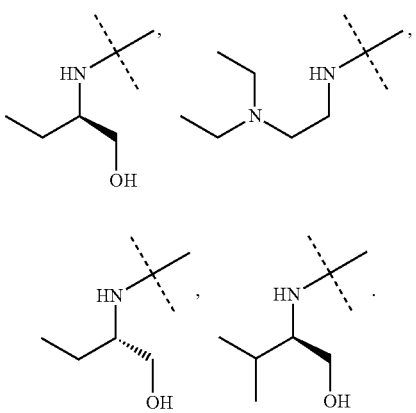

12. The method according to claim 7, wherein, in the compound of formula (Ib) or a pharmaceutically acceptable salt thereof, $R^3$ is a $(C_1-C_6)$alkyl group, a $(C_3-C_6)$cycloalkyl group, an aryl group or a —$CH_2$-aryl group, said alkyl, cycloalkyl and aryl group being optionally substituted with one or more substituents independently chosen from a halogen atom, a hydroxyl group and a $NH_2$ group, an isopropyl group or a benzyl group.

13. The method according to claim 7, wherein the compound of formula (Ib) or a pharmaceutically acceptable salt thereof, is selected from the group consisting of:

compound 13

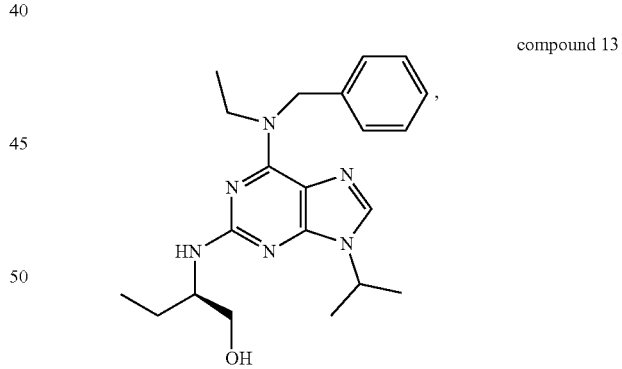

compound 14

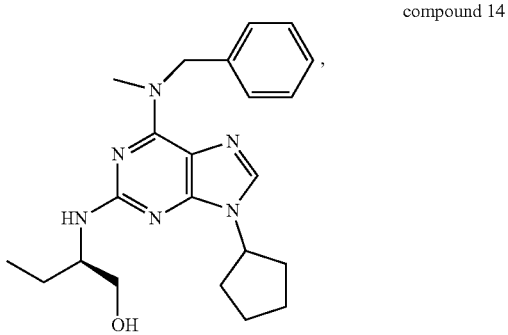

-continued compound 15

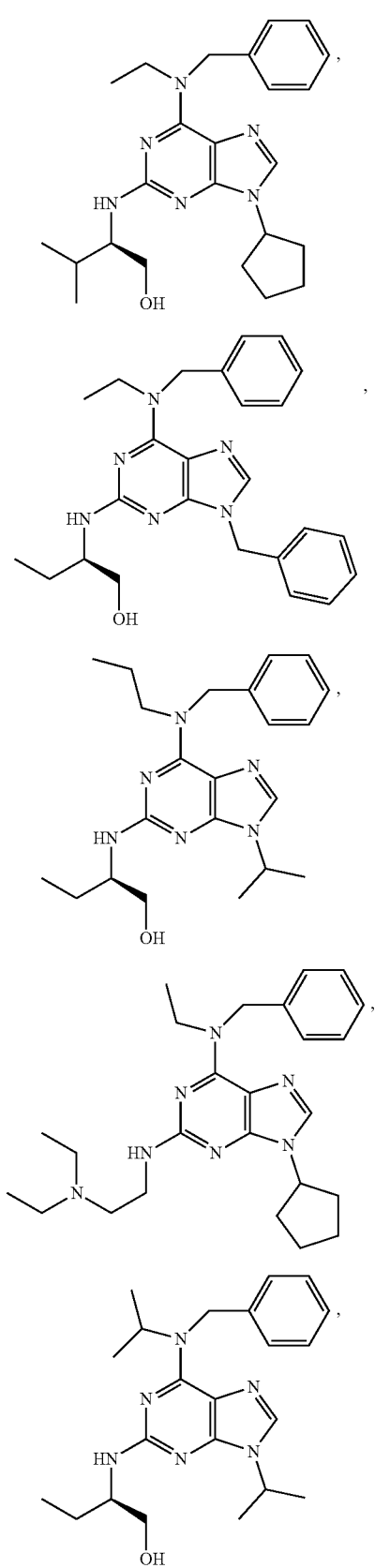

compound 18 compound 20 compound 22 compound 23

-continued compound 26

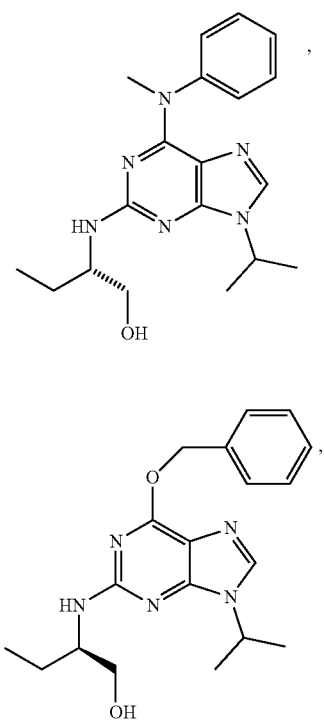

compound 31 compound 38 and compound Aftin-5

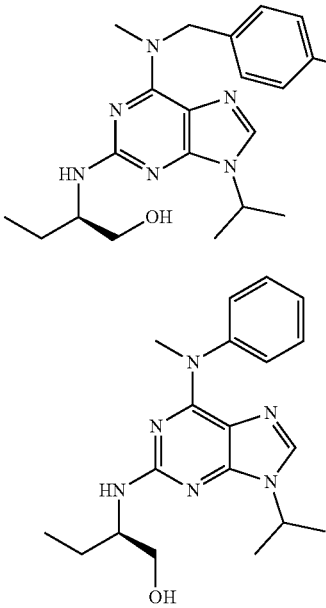

14. The method according to claim 7, wherein the effective amount of the compound of formula (Ib) is administered to the individual in need thereof as a pharmaceutical composition comprising the compound of formula (Ib), or a pharmaceutically acceptable salt thereof, and a pharmaceutically acceptable vehicle.

* * * * *